US008691982B2

(12) United States Patent
Meijer et al.

(10) Patent No.: US 8,691,982 B2
(45) Date of Patent: Apr. 8, 2014

(54) PYRAZOLO[1,5-A]-1,3,5-TRIAZINE DERIVATIVES, PREPARATION THEREOF, AND THERAPEUTIC USE THEREOF

(75) Inventors: Laurent Meijer, Roscoff (FR); Hervé Galons, Paris (FR); Benoit Joseph, Villeurbanne (FR); Florence Popowycz, Villeurbanne (FR); Nassima Oumata, Paris (FR)

(73) Assignees: Centre National de la Recherche Scientifique, Paris (FR); Universite Paris Descartes, Paris (FR); Universite Claude Bernard Lyon 1, Villeurbanne (FR); Institut National de la Sante et de la Recherche Medicale (INSERM), Paris (FR)

( * ) Notice: Subject to any disclaimer, the term of this patent is extended or adjusted under 35 U.S.C. 154(b) by 223 days.

(21) Appl. No.: 13/203,427

(22) PCT Filed: Mar. 11, 2010

(86) PCT No.: PCT/IB2010/051063
§ 371 (c)(1),
(2), (4) Date: Feb. 13, 2012

(87) PCT Pub. No.: WO2010/103486
PCT Pub. Date: Sep. 16, 2010

(65) Prior Publication Data
US 2012/0184557 A1 Jul. 19, 2012

Related U.S. Application Data

(60) Provisional application No. 61/159,246, filed on Mar. 11, 2009.

(30) Foreign Application Priority Data

Mar. 11, 2009 (FR) ...................................... 09 51521

(51) Int. Cl.
*C07D 487/04* (2006.01)
*A61K 31/53* (2006.01)
*A61P 35/00* (2006.01)

(52) U.S. Cl.
USPC .......................................... 544/204; 514/246

(58) Field of Classification Search
USPC .......................................... 544/204; 514/246
See application file for complete search history.

(56) References Cited

U.S. PATENT DOCUMENTS

2004/0048849 A1 3/2004 Prevost et al.
2005/0187219 A1 8/2005 Guzi et al.
2006/0106019 A1 5/2006 Bernard

FOREIGN PATENT DOCUMENTS

WO   WO 02/50079      6/2002
WO   WO 03/022805 A2  3/2003
WO   WO 2004/011464 A2 2/2004
WO   WO 2005/082908 A1 9/2005

OTHER PUBLICATIONS

Popowycz et al., "Pyrazolo[1,5-α]-1,3,5-triazine as a Purine Bioisostere: Access to Potent Cyclin-Dependent Kinase Inhibitor (R)-Roscovitine Analogue," J. Med. Chem., vol. 52, pp. 655-663, 2009.
K. Bettayeb et al., "N-&-N, A New Class of Cell Death-Inducing Kinase Inhibitors Derived from the Purine Roscovitine," Mol. Cancer Ther., vol. 7, No. 9, p. 2713-2724, 2008.
P. Leon et al., "Asymmetrical Bisintercalators as Potential Antitumor Agents," J. Med. Chem, vol. 31, No. 5, pp. 1021-1026, 1988.
Z. Nie et al., "Structure-based Design and Synthesis of Novel Macrocyclic Pyrazolo[1,5-α] [1,3,5]Triazine Compounds as Potent Inhibitors of Protein Kinase CK2 and their Anticancer Activities," Bioorganic & Medicinal Chemistry Letters, vol. 18, No. 2, pp. 619-623, 2008.
L. Meijer et al., "Biochemical and Cellular Effects of Roscovitine, A Potent and Selective Inhibitor of the Cyclin-dependent Kinases cdc2, cdk2 and cdk5," Eur. J. Biochem., vol. 243, pp. 527-536, 1997.
S. Bach et al., "Roscovitine Targets, Protein Kinases and Pyridoxal Kinase," J. Biol Chem., vol. 280, No. 35, Issue of Sep. 2, pp. 31208-31219, 2005.
J. Reinhardt et al., "Purification of CK I by Affinity Chromatography on Immobilised Axin," Protein Expression and Purification, vol. 54, pp. 101-109, 2007.
J. Ribas et al, "Cell Differentiation, Caspase Inhibition, and Macromolecular Synthesis Blockage, but not BCI-2 or BCL-XL Proteins, Protect SH-SY5Y Cells from Apoptosis Triggered by Two CDK Inhibitory Drugs," Experimental Cell Research, vol. 295, pp. 9-24, 2004.
May 21, 2010 International Search Report issued in International Application No. PCT/IB2010/051063 (with translation).
May 21, 2010 Written Opinion issued in International Application No. PCT/IB2010/051063 (with translation).
Oct. 1, 2009 Search Report issued in French Application No. FR 0951521 (with translation).

*Primary Examiner* — Venkataraman Balasubramanian
(74) *Attorney, Agent, or Firm* — Oliff PLC

(57) ABSTRACT

A compound of formula (I), or a pharmaceutically acceptable salt thereof, where $R_1$ is a $(C_1-C_6)$alkyl or $(C_3-C_6)$cycloalkyl group; $R_2$ is a $(C_1-C_6)$alkyl, $(C_3-C_6)$cycloalkyl, $(C_1-C_6)$alkenyl, $(C_1-C_6)$fluoroalkyl, $(C_1-C_3)$fluoroalkoxy, or $(C_1-C_6)$alkoxy$(C_1-C_6)$alkyl group, substituted: (i) with one to three hydroxyl groups, or (ii) with an $NR_aR_b$ group, where $R_a$ and $R_b$ are independently a hydrogen atom or a $(C_1-C_3)$alkyl group; or a pyrrolidinylmethyl group substituted with one to three hydroxyl groups; $R_9$ is the same as $R_2$ or hydrogen; the $R_2$ and $R_9$ groups independently being substitutable with an —$OCOR_3$ group, where $R_3$ is a natural or unnatural amino acid derivative or a piperidyl group; alternatively, $R_2$ and $R_9$ together form a heterocyclic compound; X and Y are independently a substitutable phenyl or heteroaryl group, the heteroaryl group being a thienyl, pyridyl, pyrimidinyl, thiazolyl, pyrrolyl, or furanyl group; and $R_6$ is a hydrogen or a $(C_1-C_3)$ alkyl group.

12 Claims, No Drawings

PYRAZOLO[1,5-A]-1,3,5-TRIAZINE DERIVATIVES, PREPARATION THEREOF, AND THERAPEUTIC USE THEREOF

The invention relates to pyrazolo[1,5-a]-1,3,5-triazine derivatives, to the preparation thereof and to the therapeutic use thereof.

A certain number of documents describe compounds derived from pyrazolo[1,5-a]-1,3,5-triazines.

Thus, pyrazolotriazine compounds as kinase inhibitors are known from document WO 2005/082908.

Compounds which are inhibitors of cyclin-dependent kinases (CDKs) and of glycogen synthase kinase-3 (GSK-3) are known from document WO 2002/50079.

Finally, document WO 2004/011464 describes, inter alia, compounds which are inhibitors of the phosphodiesterases PDE2 and PDE4.

Moreover, Bettayeb et al., "N-&-N, a new class of cell death-inducing kinase inhibitors derived from the purine roscovitine", *Mol. Cancer Ther.* 2008, 7, 2713 and "Pyrazolo[1,5-a]-1,3,5-triazine as a purine bioisostere: access to potent cyclin-dependent kinase inhibitor (R)-roscovitine analogue", *J. Med. Chem.* 2009, 52, 655, describe the antitumor potential of the compound called N-&-N1:

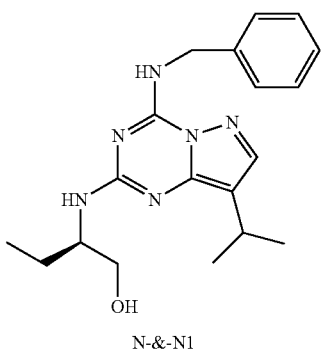 [SMILES: CC[C@H](CO)Nc1nc(NCc2ccccc2)n2ncc(C(C)C)c2n1]

N-&-N1

The subject of the invention is compounds corresponding to formula (I) hereinafter;

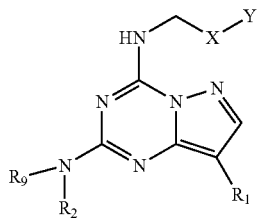

in which:
$R_1$ is a $(C_1\text{-}C_6)$alkyl group or a $(C_3\text{-}C_6)$cycloalkyl group,
$R_2$ is a $(C_1\text{-}C_6)$alkyl group, a $(C_3\text{-}C_6)$cycloalkyl group, a $(C_1\text{-}C_6)$alkenyl group, a $(C_1\text{-}C_6)$fluoroalkyl group, a $(C_1\text{-}C_3)$ fluoroalkoxy group or a $(C_1\text{-}C_6)$alkoxy$(C_1\text{-}C_6)$alkyl group, substituted (i) with one to three hydroxyl groups, or (ii) with an $NR_aR_b$ group, where $R_a$ and $R_b$ are independently a hydrogen atom or a $(C_1\text{-}C_3)$alkyl group,
or else $R_2$ is a pyrrolidinylmethyl group substituted with one to three hydroxyl groups,
said $R_2$ group being optionally substituted with an —OCOR$_3$ group, in which $R_3$ is a natural or unnatural amino acid derivative or a piperidyl group of formula (B)

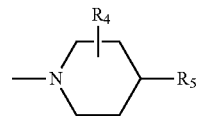

in which:
$R_4$ is a hydrogen, a halogen atom, a $(C_1\text{-}C_3)$alkyl group, a hydroxy$(C_1\text{-}C_3)$alkyl group or an —NR$_a$R$_b$ group, where R$_a$ and R$_b$ are as defined above, and $R_5$ is a hydrogen, a $(C_1\text{-}C_3)$ alkyl group, an —N(Me)$_2$ group, a piperidyl group or a morpholinyl group,
$R_9$ has the same meaning as $R_2$ and may also be a hydrogen atom,
alternatively, $R_2$ and $R_9$ together form, with the nitrogen atom which bears them, a heterocycle chosen from pyrrolidinyl, piperidinyl, piperazinyl and piperidinylpiperidinyl groups, it being possible for these heterocycles to be substituted with one to three groups chosen from hydroxyl, $(C_1\text{-}C_6)$alkyl or $(C_1\text{-}C_6)$alkoxy$(C_1\text{-}C_6)$alkyl, these last two groups being substituted (i) with one to three hydroxyl groups, or (ii) with an $NR_aR_b$ group, where $R_a$ and $R_b$ are independently a hydrogen atom or a $(C_1\text{-}C_3)$alkyl group,
X and Y are independently a phenyl group or a heteroaryl group, it being possible for said heteroaryl and phenyl groups to be substituted with one or two groups independently chosen from a $(C_1\text{-}C_2)$alkyl group, a $(C_1\text{-}C_2)$alkoxy group, a halogen atom, a $(C_1\text{-}C_2)$fluoroalkyl group, a $(C_1\text{-}C_2)$fluoroalkoxy group, a hydroxyl group, a —COOH group, a —CONHR$_6$ group and an —NR$_a$R$_b$ group, where R$_a$ and R$_b$ are as defined above,
$R_6$ is a hydrogen or a $(C_1\text{-}C_3)$alkyl group,
said heteroaryl group being chosen from a thienyl group, a pyridyl group, a pyrimidinyl group, a thiazolyl group, a pyrrolyl group and a (uranyl group,
and also the pharmaceutically acceptable salts thereof.

Said group derived from a natural or unnatural amino acid may be derived from the 20 natural amino acids. Among said natural amino acids, mention may in particular be made of L-valine, L-leucine, L-serine, L-threonine, L-asparagine and aspartic acid.

Among the unnatural amino acid derivatives, mention may be made of the acyl derivatives of the natural amino acids, namely comprising, in place of the terminal —COOH group, a $(C_1\text{-}C_3)$alkylcarbonyl group or a $(C_1\text{-}C_4)$alkoxycarbonyl group, in particular a methylcarbonyl group giving an acetylated derivative or else a tert-butoxycarbonyl group giving a Boc derivative.

D-configuration amino acid derivatives may also be used.

According to one aspect of the invention, the heteroaryl group is chosen from a thienyl group, a (uranyl group and a pyridyl group.

According to one particular aspect of the invention, $R_3$ is one of the following formulae (a-1) to (a-5):

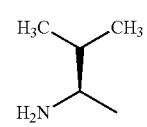

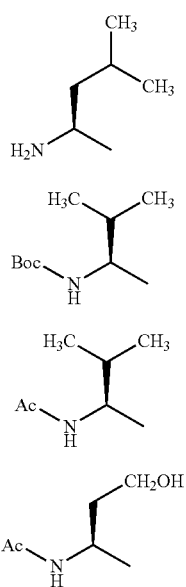

where Boc is a tert-butoxycarbonyl group and Ac an acetyl group, and also the enantiomers thereof.

The compounds of formula (I) may comprise one or more asymmetric carbon atoms. It may therefore exist in the form of enantiomers or of diastereoisomers. These enantiomers and diastereoisomers, and also mixtures thereof, including racemic mixtures, are part of the invention.

The compounds of formula (I) may exist in the form of bases or of addition salts with acids. Such addition salts are part of the invention.

These salts are advantageously prepared with pharmaceutically acceptable acids, but the salts of other acids that are useful, for example, for purifying or isolating the compounds of formula (I) are also part of the invention.

Among the pharmaceutically acceptable acids, mention may in particular be made of hydrochloric acid, hydrobromic acid, trifluoroacetic acid, fumaric acid, tartaric acid, citric acid, ascorbic acid and maleic acid.

The compounds of formula (I) may also exist in the form of hydrates or of solvates, that is to say in the form of associations or combinations with one or more molecules of water or with a solvent. Such hydrates and solvates are also part of the invention.

In the context of the present invention:

"$(C_t—C_z)$ where t and z can have the values of from 1 to 6" is intended to mean a carbon-based chain that can have from t to z carbon atoms, for example "$(C_1-C_3)$" a carbon-based chain that can have from 1 to 3 carbon atoms;

"halogen" is intended to mean an atom chosen from fluorine, chlorine, bromine and iodine, in particular from fluorine, chlorine and bromine;

"an alkyl group" is intended to mean a linear or branched saturated aliphatic group. By way of examples, mention may be made of methyl, ethyl, propyl, isopropyl, butyl, isobutyl, tert-butyl, pentyl, etc., groups;

"an alkenyl group" is intended to mean a linear or branched aliphatic group comprising one or two unsaturations. By way of example, mention may be made of ethenyl, propenyl, isopropenyl, butenyl, isobutenyl, tert-butenyl, pentenyl, etc. groups;

"a cycloalkyl group" is intended to mean a cyclic alkyl group. By way of examples, mention may be made of cyclopropyl, cyclobutyl, cyclopentyl, cyclohexyl, etc., groups;

"an alkoxy group" is intended to mean an O-alkyl group where the alkyl group is as defined above;

"a phenyl group" is intended to mean both the (monovalent) phenyl group and the corresponding divalent group phenylene;

"a heteroaryl group" is intended to mean both the (monovalent) heteroaryl group and the corresponding divalent group heteroarylene, said heteroaryl group being an aromatic or nonaromatic, monocyclic or bicyclic group comprising one or two heteroatoms such as nitrogen, oxygen or sulphur;

"a fluoroalkyl group" and "a fluoroalkoxy group" are intended to mean, respectively, an alkyl group and an alkoxy group, as defined above, substituted with at least one fluorine atom. By way of examples, mention may be made of perfluoroalkyl groups such as trifluoromethyl or perfluoropropyl.

According to one particular embodiment, the $R_1$ group is an ethyl group or an isopropyl group.

According to one particular embodiment, the X and Y groups are not substituted.

According to another particular embodiment, when at least one of the X and Y groups is substituted, it comprises one or two substitution groups and said substitution group is advantageously independently chosen from a $(C_1-C_2)$alkyl group, a $(C_1-C_2)$fluoroalkyl group, a $(C_1-C_2)$alkoxy group, a $(C_1-C_2)$ fluoroalkoxy group, a halogen atom, a hydroxyl group and a —COOH group.

Still according to this other embodiment, when Y is a heteroaryl group and is monosubstituted, the substitution is advantageously in position 3 or 5.

According to another particular embodiment, the $R_2$ group is one of the following formulae, the $R_9$ group then being a hydrogen atom:

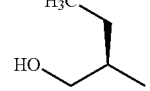

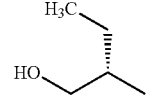

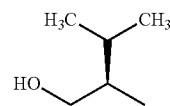

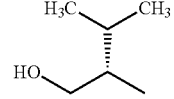

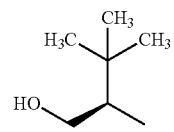

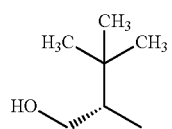 (b-6)
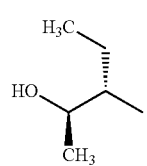 (b-7)
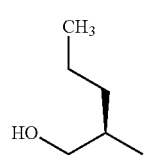 (b-8)
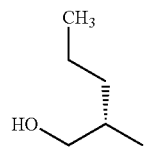 (b-9)
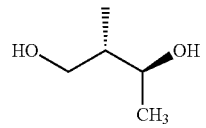 (b-10)
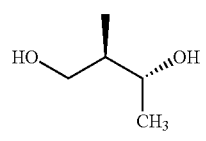 (b-11)
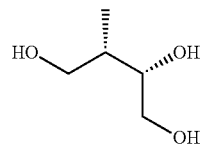 (b-12)
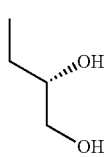 (b-13)
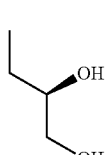 (b-14)
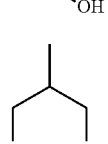 (b-15)
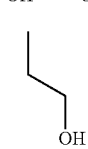 (b-16)
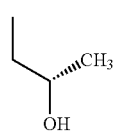 (b-17)
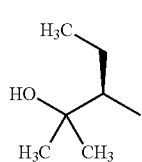 (b-18)
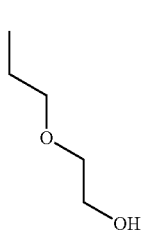 (b-19)
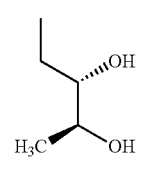 (b-20)
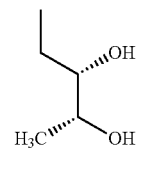 (b-21)
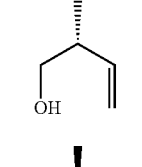 (b-22)
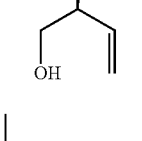 (b-23)
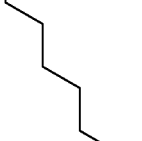 (b-24)
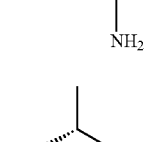 (b-25)
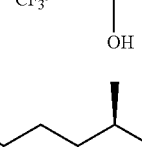 (b-26)

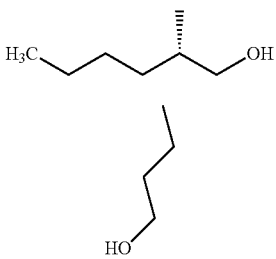 (b-27)

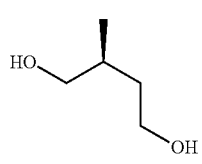 (b-28)

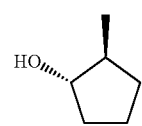 (b-29)

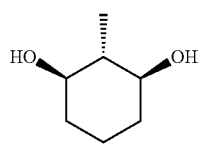 (b-30)

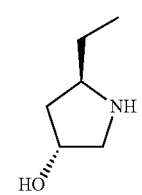 (b-31)

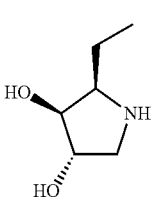 (b-32)

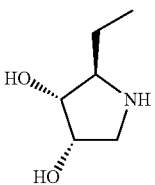 (b-33)

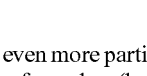 (b-34)

According to one even more particular embodiment, the $R_2$ group is one of the formulae (b-1), (b-2), (b-10), (b-11), (b-13), (b-14) or (b-15) as defined above.

According to one particular embodiment, when $R_2$ and $R_9$ together form a heterocycle, the pyrrolidinyl group is advantageously a pyrrolidin-1-yl group, the piperidinyl group is advantageously a piperidin-1-yl group, the piperazinyl group is advantageously a piperazin-1-yl group and the piperidinylpiperidinyl group is advantageously a piperidin-4-ylpiperidin-1-yl group.

According to yet another particular embodiment, the $NR_2R_9$ group is one of the following formulae:

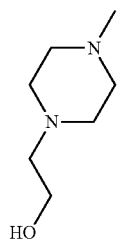 (b-35)

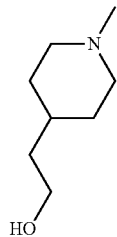 (b-36)

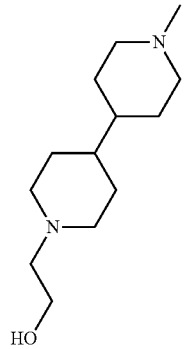 (b-37)

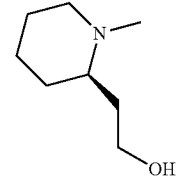 (b-38)

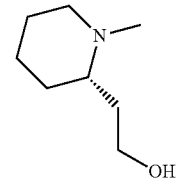 (b-39)

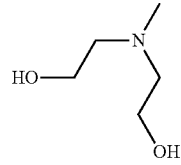 (b-40)

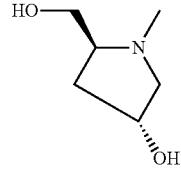 (b-41)

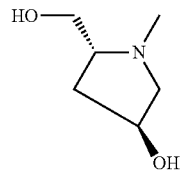
(b-42)

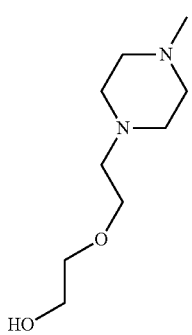
(b-43)

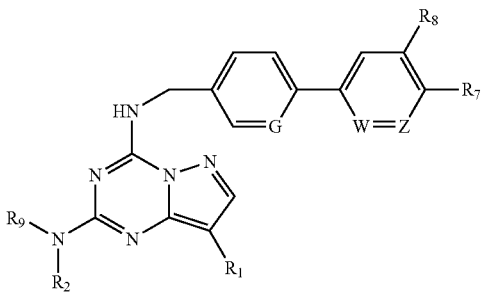
(Ia)

in which:

R₁ is as defined above and is advantageously an isopropyl group,

R₂ and R₉ are independently a (C₁-C₆)alkyl group, a (C₁-C₆)fluoroalkyl group, a (C₁-C₃)fluoroalkoxy group or a (C₁-C₆)alkoxy(C₁-C₆)alkyl group, said group being substituted with one to three hydroxyl groups, with it being possible for R₉ to be a hydrogen atom, and R₂ advantageously is one of the formulae (b-1), (b-2), (b-10), (b-11), (b-13), (b-14) or (b-15) as defined above, while R₉ is a hydrogen atom, or else R₂ and R₉ together form, with the nitrogen atom which bears them, a piperidin-1-yl or piperidin-4-ylpiperidin-1-yl group, said group being substituted with one to three (C₁-C₆)alkyl groups substituted with a hydroxyl group, and R₂ and R₉ taken together are advantageously one of the formulae (b-37), (b-38), (b-39) or (b-40) as defined above, R₇ and R₈ are independently a hydrogen atom, a (C₁-C₂)alkyl group, a (C₁-C₂)fluoroalkyl group, a (C₁-C₂)alkoxy group, a (C₁-C₂)fluoroalkoxy group, a halogen atom, a hydroxyl group or a —COOH group, G is —CH═, or —N═, and when G is —CH═, the W and Z groups are either simultaneously —CH═, or one is —N═ and the other is —CH═, when G is —N═, then W and Z are —CH═.

Among the compounds which are subjects of the invention, mention may be made of a second group of compounds of formula (Ib), which are covered by formula (I):

According to yet another particular embodiment, the NR₂R₉ group has one of the formulae (b-35) to (b-43), with the exclusion of the (b-38) and (b-39) groups.

According to another even more particular embodiment, the invention relates to compounds of formula (I) as defined above, in which R₁ is an isopropyl group; R₂ is a (C₁-C₆)alkyl group, a (C₁-C₆)fluoroalkyl group, a (C₁-C₃)fluoroalkoxy group or a (C₁-C₆)alkoxy(C₁-C₆)alkyl group, said group being substituted with one to three hydroxyl groups and is advantageously one of the formulae (b-1), (b-2), (b-10), (b-11), (b-13), (b-14) or (b-15) as defined above; and X and Y are as defined above and are not substituted and are advantageously independently a phenyl group, a pyridyl group or a thienyl group, it being understood that X and Y are not simultaneously a thienyl group or a pyridyl group.

According to yet another particular embodiment, the piperidyl group of formula (B) is one of the following groups:

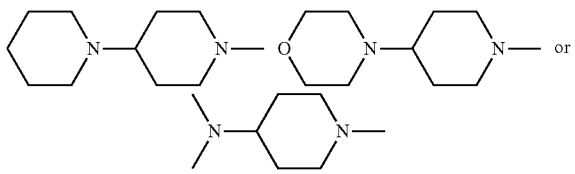

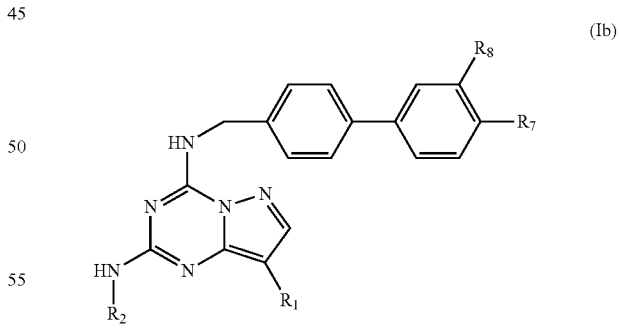
(Ib)

in which:

R₁ is as defined above and is advantageously an isopropyl group,

R₂ is a (C₁-C₆)alkyl group, a (C₁-C₆)fluoroalkyl group, a (C₁-C₃)fluoroalkoxy group or a (C₁-C₆)alkoxy(C₁-C₆)alkyl group, said group being substituted with one to three hydroxyl groups, and advantageously is one of the formulae (b-1), (b-2), (b-10), (b-11), (b-13), (b-14) or (b-15) as defined above, and Among the compounds which are subjects of the invention, mention may be made of a first group of compounds of formula (Ia), which are covered by formula (I):

$R_7$ and $R_8$ are independently a hydrogen atom, a $(C_1-C_2)$alkyl group, a $(C_1-C_2)$fluoroalkyl group, a $(C_1-C_2)$alkoxy group, a $(C_1-C_2)$fluoroalkoxy group, a halogen atom, a hydroxyl group or a —COOH group.

Among the compounds which are subjects of the invention, mention may be made of a third group of compounds of formula (Ic), which are covered by formula (I):

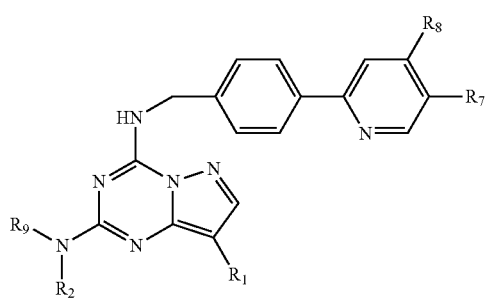

in which:

$R_1$ is as defined above and is advantageously an ethyl or isopropyl group, either $R_9$ is a hydrogen atom and $R_2$ is a $(C_1-C_6)$alkyl group, a $(C_1-C_6)$fluoroalkyl group, a $(C_1-C_3)$fluoroalkoxy group or a $(C_1-C_6)$alkoxy$(C_1-C_6)$alkyl group, said group being substituted with one to three hydroxyl groups, and advantageously is one of the formulae (b-1), (b-2), (b-10), (b-11), (b-13), (b-14) or (b-15) as defined above, or $R_2$ and $R_9$ together form, with the nitrogen atom which bears them, a piperidin-1-yl or piperidin-4-ylpiperidin-1-yl group, said group being substituted with one to three $(C_1-C_6)$ alkyl groups substituted with a hydroxyl group, and $R_2$ and $R_9$ taken together are advantageously one of the formulae (b-37), (b-38), (b-39) or (b-40) as defined above, and $R_7$ and $R_8$ are independently a hydrogen atom, a $(C_1-C_2)$alkyl group, a $(C_1-C_2)$fluoroalkyl group, a $(C_1-C_2)$alkoxy group, a $(C_1-C_2)$fluoroalkoxy group, a halogen atom, a hydroxyl group or a —COOH group.

Among the compounds which are subjects of the invention, mention may be made of a third group of compounds of formula (Id), which are covered by formula (I):

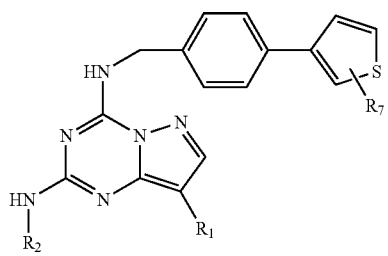

in which:

$R_1$ is as defined above and is advantageously an isopropyl group, $R_2$ is a $(C_1-C_6)$alkyl group, a $(C_1-C_6)$fluoroalkyl group, a $(C_1-C_3)$fluoroalkoxy group or a $(C_1-C_6)$alkoxy$(C_1-C_6)$alkyl group, said group being substituted with one to three hydroxyl groups, and advantageously is one of the formulae (b-1), (b-2), (b-10), (b-11), (b-13), (b-14) or (b-15) as defined above, and $R_7$ is a hydrogen atom, a $(C_1-C_2)$alkyl group, a $(C_1-C_2)$fluoroalkyl group, a $(C_1-C_2)$alkoxy group, a $(C_1-C_2)$fluoroalkoxy group, a halogen atom, a hydroxyl group or a —COOH group.

Among the compounds which are subjects of the invention, mention may be made of a fourth group of compounds of formula (Ie), which are covered by formula (I):

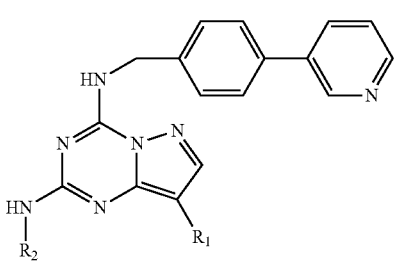

in which:

$R_1$ is as defined above and advantageously an isopropyl group, $R_2$ is a $(C_1-C_6)$alkyl group, a $(C_1-C_6)$fluoroalkyl group, a $(C_1-C_3)$fluoroalkoxy group or a $(C_1-C_6)$alkoxy$(C_1-C_6)$alkyl group, said group being substituted with one to three hydroxyl groups, and advantageously is one of the formulae (b-1), (b-2), (b-10), (b-11), (b-13), (b-14) or (b-15) as defined above.

Among the compounds which are subjects of the invention, mention may be made of a fifth group of compounds of formula (If), which are covered by formula (I):

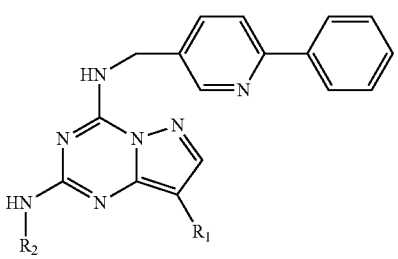

in which:

$R_1$ is as defined above and advantageously an isopropyl group, $R_2$ is a $(C_1-C_6)$alkyl group, a $(C_1-C_6)$fluoroalkyl group, a $(C_1-C_3)$fluoroalkoxy group or a $(C_1-C_6)$alkoxy$(C_1-C_6)$alkyl group, said group being substituted with one to three hydroxyl groups, and advantageously is one of the formulae (b-1), (b-2), (b-10), (b-11), (b-13), (b-14) or (b-15) as defined above.

The pharmaceutically acceptable salts of the compounds of formulae (Ia), (Ib), (Ic), (Id), (Ie) and (If) are also part of the invention.

Among the compounds of formula (I) of the invention, mention may in particular be made of the following compounds:

(R)-2-(1-hydroxybut-2-ylamino)-8-isopropyl-4-(4-phenylbenzylamino)pyrazolo[1,5-a]-1,3,5-triazine (1)

(R)-2-(1-hydroxybut-2-ylamino)-8-isopropyl-4-[4-(pyridin-2-yl)benzylamino]pyrazolo[1,5-a]-1,3,5-triazine (2)

Fumarate salt of (R)-2-(1-hydroxybut-2-ylamino)-8-isopropyl-4-[4-(pyridin-2-yl)benzylamino]pyrazolo[1,5-a]-1,3,5-triazine (3)

(S)-2-(1-hydroxybut-2-ylamino)-8-isopropyl-4-[4-(pyridin-2-yl)benzylamino]pyrazolo[1,5-a]-1,3,5-triazine (4)

Fumarate salt of (S)-2-(1-hydroxybut-2-ylamino)-8-isopropyl-4-[4-(pyridin-2-yl)benzylamino]pyrazolo[1,5-a]-1,3,5-triazine (5)

(R)-2-(1-hydroxybut-2-ylamino)-8-isopropyl-4-[4-(thiophen-3-yl)benzylamino]pyrazolo[1,5-a]-1,3,5-triazine (6)

(S)-2-(1-hydroxybut-2-ylamino)-8-isopropyl-4-[4-(thiophen-3-yl)benzylamino]pyrazolo[1,5-a]-1,3,5-triazine (7)

(S)-2-(1,2-dihydroxypropan-3-ylamino)-8-isopropyl-4-[4-(pyridin-2-yl)benzylamino]pyrazolo[1,5-a]-1,3,5-triazine (8)

Fumarate salt of (S)-2-(1,2-dihydroxypropan-3-ylamino)-8-isopropyl-4-[4-(pyridin-2-yl)benzylamino]pyrazolo[1,5-a]-1,3,5-triazine (9)

(R)-2-(1,2-dihydroxypropan-3-ylamino)-8-isopropyl-4-[4-(pyridin-2-yl)benzylamino]pyrazolo[1,5-a]-1,3,5-triazine (10)

Fumarate salt of (R)-2-(1,2-dihydroxypropan-3-ylamino)-8-isopropyl-4-[4-(pyridin-2-yl)benzylamino]pyrazolo[1,5-a]-1,3,5-triazine (11)

(2R,3R)-2-(1,3-dihydroxybut-2-ylamino)-8-isopropyl-4-[4-(pyridin-2-yl)benzylamino]pyrazolo[1,5-a]-1,3,5-triazine (12)

Fumarate salt of (2R,3R)-2-(1,3-dihydroxybut-2-ylamino)-8-isopropyl-4-[4-(pyridin-2-yl)benzylamino]pyrazolo[1,5-a]-1,3,5-triazine (13)

(2S,3S)-2-(1,3-dihydroxybut-2-ylamino)-8-isopropyl-4-[4-(pyridin-2-yl)benzylamino]pyrazolo[1,5-a]-1,3,5-triazine (14)

Fumarate salt of (2S,3S)-2-(1,3-dihydroxybut-2-ylamino)-8-isopropyl-4-[4-(pyridin-2-yl)benzylamino]pyrazolo[1,5-a]-1,3,5-triazine (15)

(2R,3R)-2-(1,3-dihydroxybut-2-ylamino)-8-isopropyl-4-[4-(thiophen-3-yl)benzylamino]pyrazolo[1,5-a]-1,3,5-triazine (16)

2-(1,3-dihydroxyprop-2-ylamino)-8-isopropyl-4-[4-(pyridin-2-yl)benzylamino]pyrazolo[1,5-a]-1,3,5-triazine (17)

Fumarate salt of 2-(1,3-dihydroxyprop-2-ylamino)-8-isopropyl-4-[4-(pyridin-2-yl)benzylamino]pyrazolo[1,5-a]-1,3,5-triazine (18)

2-(1,3-dihydroxyprop-2-ylamino)-8-isopropyl-4-[4-(pyridin-3-yl)benzylamino]pyrazolo[1,5-a]-1,3,5-triazine (19)

(S)-2-(1-hydroxybut-2-ylamino)-8-isopropyl-4-[4-(pyridin-3-yl)benzylamino]pyrazolo[1,5-a]-1,3,5-triazine (20)

(2S,3S)-2-(1,3-dihydroxybut-2-ylamino)-8-isopropyl-4-[4-phenyl(pyridin-3-yl)methylamino]pyrazolo[1,5-a]-1,3,5-triazine (21)

(S)-2-(1-hydroxybut-2-ylamino)-8-isopropyl-4-[4-phenyl(pyridin-3-yl)methylamino]pyrazolo[1,5-a]-1,3,5-triazine (22)

(2R,3R)-2-(1,3-dihydroxybut-2-ylamino)-8-isopropyl-4-[4-phenyl(pyridin-3-yl)methylamino]pyrazolo[1,5-a]-1,3,5-triazine (23)

2-(1,3-dihydroxyprop-2-ylamino)-8-isopropyl-4-[4-phenyl(pyridin-3-yl)methylamino]pyrazolo[1,5-a]-1,3,5-triazine (24)

(R)-2-(1-hydroxy-4-methylpent-2-ylamino)-8-isopropyl-4-[4-phenyl(pyridin-3-yl)methylamino]pyrazolo[1,5-a]-1,3,5-triazine (25)

(S)-2-(1-hydroxy-4-methylpent-2-ylamino)-8-isopropyl-4-[4-phenyl(pyridin-3-yl)methylamino]pyrazolo[1,5-a]-1,3,5-triazine (26)

(S)-2-(1-hydroxy-3,3-dimethylbut-2-ylamino)-8-isopropyl-4-[4-(pyridin-2-yl)benzylamino]pyrazolo[1,5-a]-1,3,5-triazine (27)

(S)-2-(1-hydroxy-3-methylbut-2-ylamino)-8-isopropyl-4-[4-(pyridin-2-yl)benzylamino]pyrazolo[1,5-a]-1,3,5-triazine (28)

2-[4-[1-[8-isopropyl-4-[[4-(pyridin-2-yl)phenyl]methylamino]pyrazolo[1,5-a]-1,3,5-triazin-2-yl]piperidin-4-yl]piperidin-1-yl]ethanol (29)

2-[4-[8-isopropyl-4-[[4-(pyridin-2-yl)phenyl]methylamino]pyrazolo[1,5-a]-1,3,5-triazin-2-yl]piperazin-1-yl]ethanol (30)

(R)-2-(1,2-dihydroxypropan-3-ylamino)-8-ethyl-4-[4-(pyridin-2-yl)benzylamino]pyrazolo[1,5-a]-1,3,5-triazine (31)

[(2R)-3-[[8-ethyl-4-[[4-(2-pyridyl)phenyl]methylamino]pyrazolo[1,5-a][1,3,5]-triazin-2-yl]amino]-2-hydroxypropyl] (2R)-2-Bocamino-3-methylbutanoate (32)

[(2R)-3-[[8-ethyl-4-[[4-(2-pyridyl)phenyl]methylamino]pyrazolo[1,5-a][1,3,5]triazin-2-yl]amino]-2-hydroxypropyl] (2R)-2-amino-3-methylbutanoate (33) in the form of a base or of a salt, in particular dihydrochloride (S)-2-(1,2-dihydroxypropan-3-ylamino)-8-ethyl-4-[4-(pyridin-2-yl)benzylamino]pyrazolo[1,5-a]-1,3,5-triazine (34)

(S)-8-ethyl-2-(1-hydroxybut-2-ylamino)-4-[4-(pyridin-2-yl)benzylamino]pyrazolo[1,5-a]-1,3,5-triazine (35)

(R)-8-ethyl-2-(1-hydroxybut-2-ylamino)-4-[4-(pyridin-2-yl)benzylamino]pyrazolo[1,5-a]-1,3,5-triazine (36)

2-(1,3-dihydroxyprop-2-ylamino)-8-ethyl-4-[4-(pyridin-2-yl)benzylamino]pyrazolo[1,5-a]-1,3,5-triazine (37)

2-[(2S)-1-[8-ethyl-4-[[4-(2-pyridyl)phenyl]methylamino]pyrazolo[1,5-a][1,3,5]triazin-2-yl]-2-piperidyl]ethanol (38)

2-[[8-ethyl-4-[[4-(2-pyridyl)phenyl]methylamino]pyrazolo[1,5-a][1,3,5]triazin-2-yl]-(2-hydroxyethyl)amino]ethanol (39)

(2R,3R)-2-[[8-ethyl-4-[[4-(2-pyridyl)phenyl]methylamino]pyrazolo[1,5-a][1,3,5]triazin-2-yl]amino]butane-1,3-diol (40)

(2S,3S)-2-[[8-ethyl-4-[[4-(2-pyridyl)phenyl]methylamino]pyrazolo[1,5-a][1,3,5]triazin-2-yl]amino]butane-1,3-diol (41)

and also their optional salts of pharmaceutically acceptable acids.

The following compounds are also part of the invention.
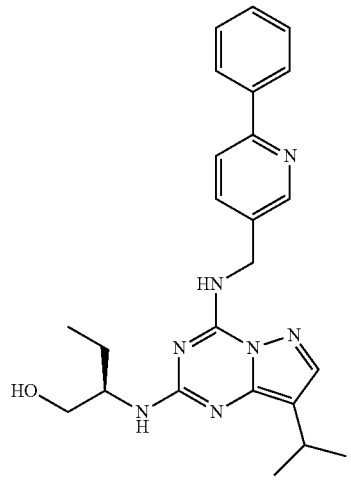
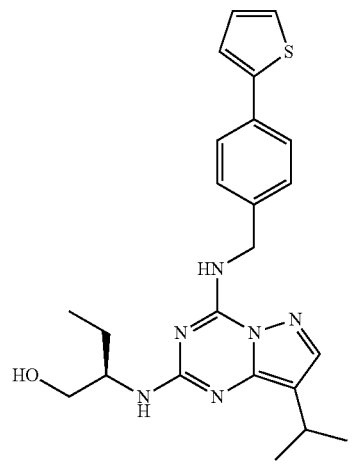
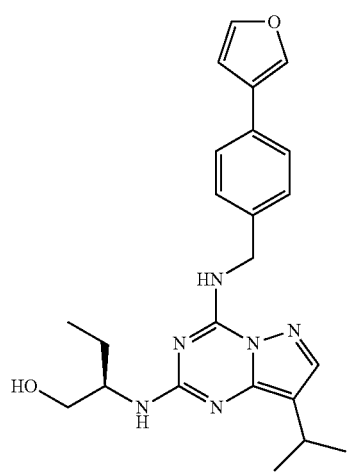
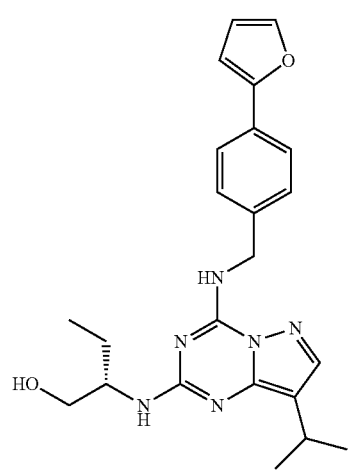
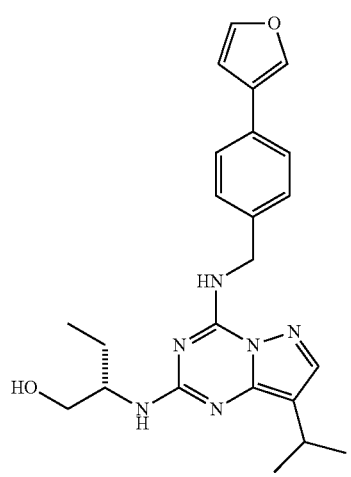
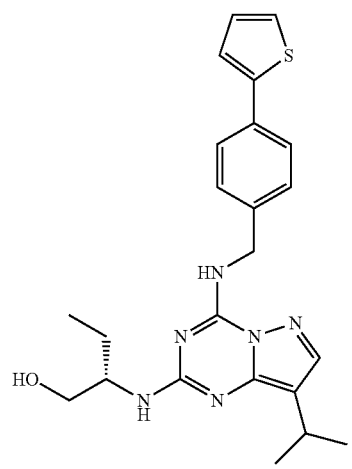

-continued
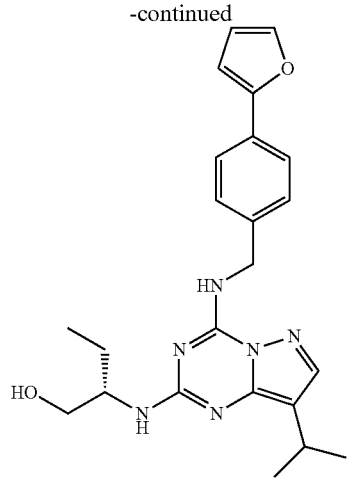
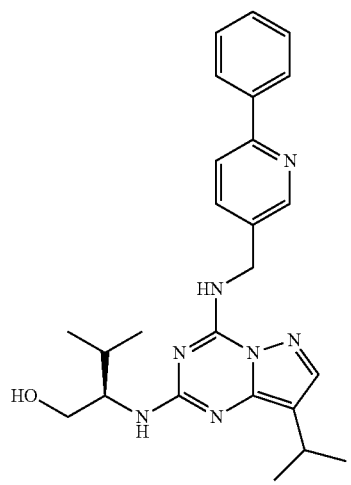
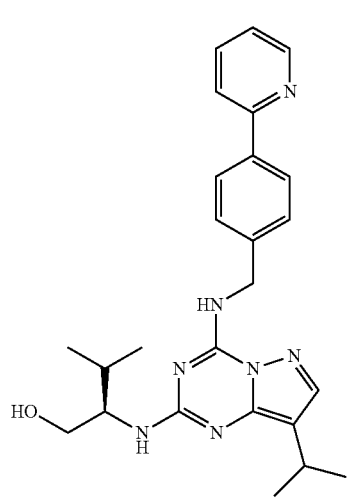
-continued
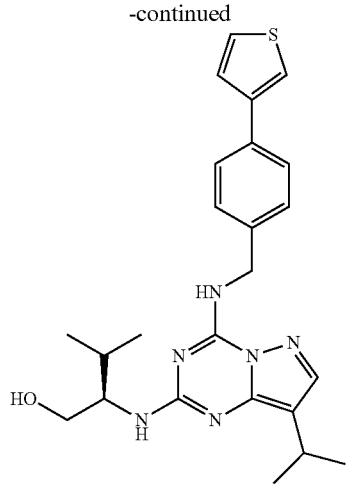
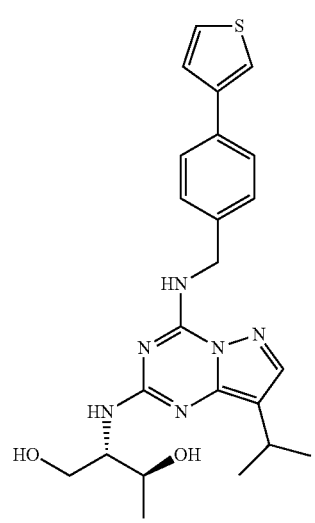
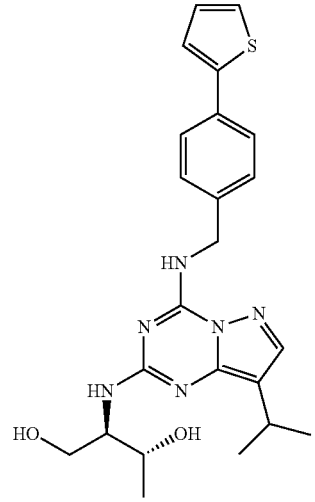

19
-continued
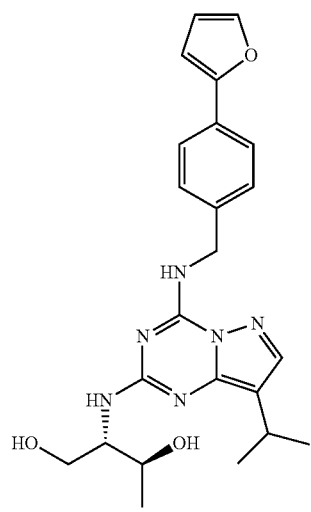
20
-continued
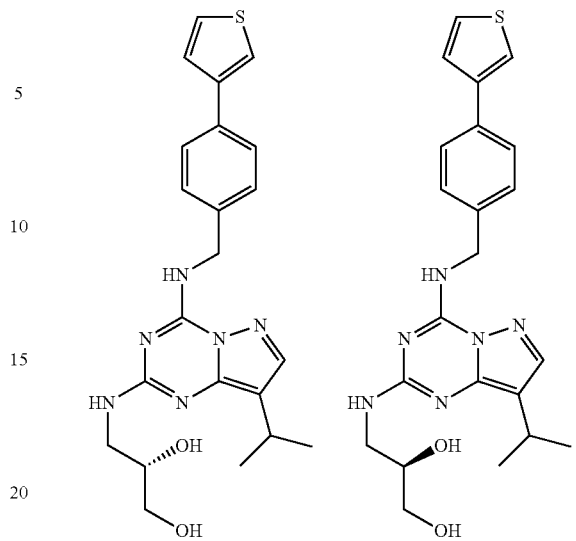
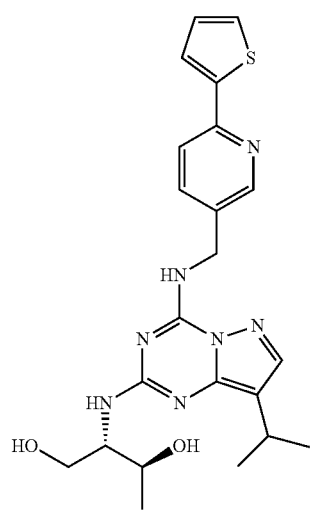
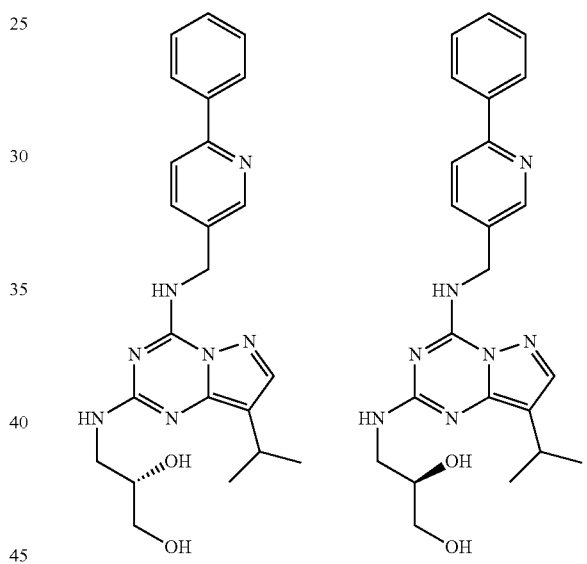
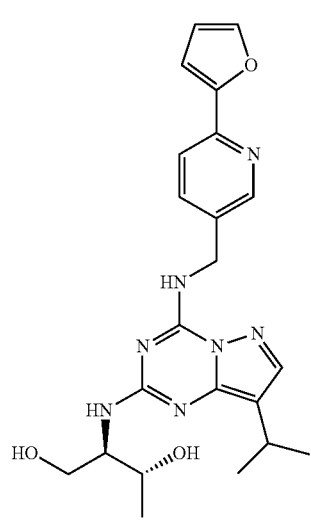
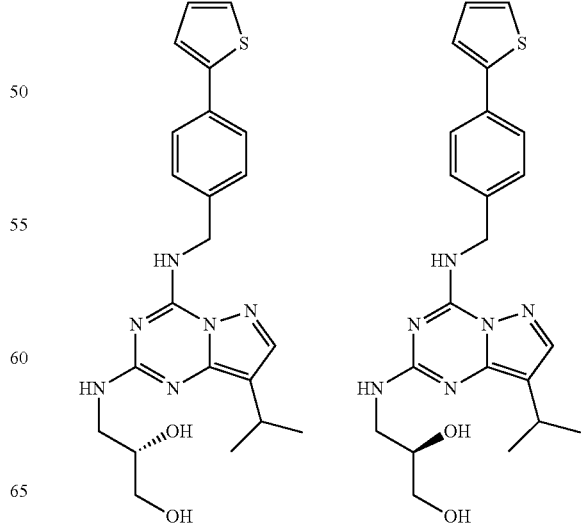

21
-continued
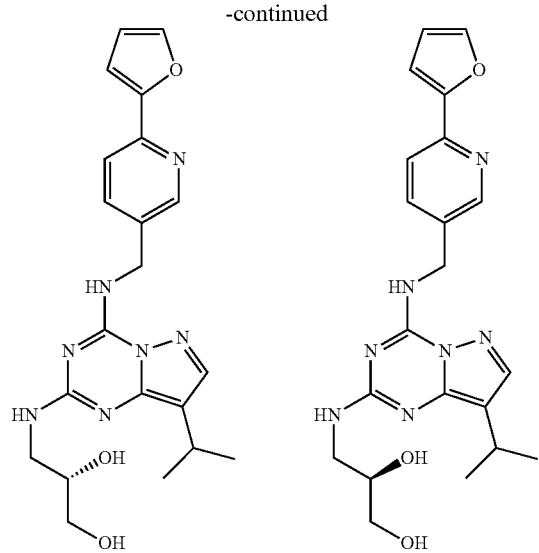
22
-continued
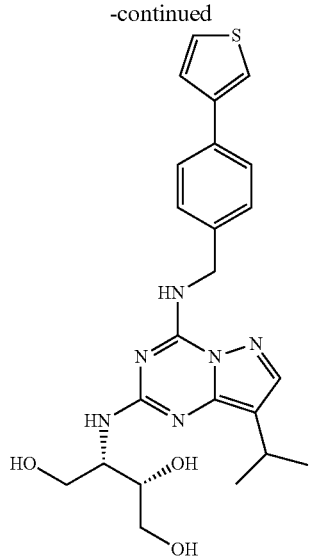
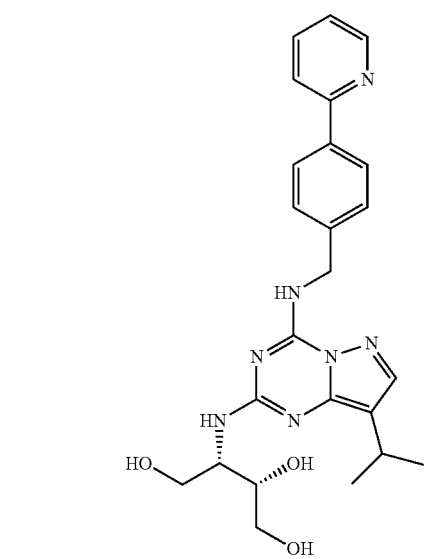
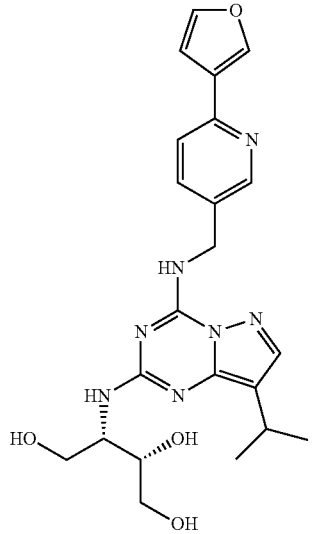
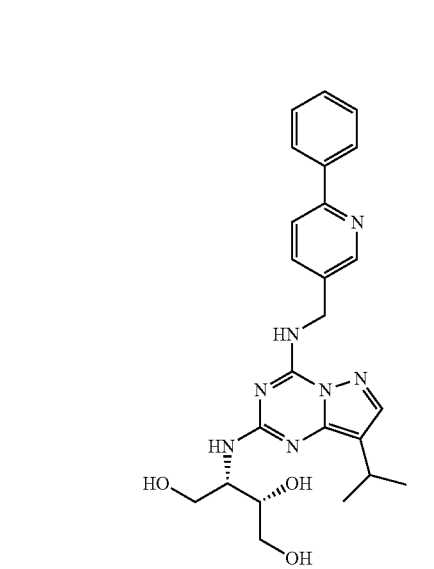
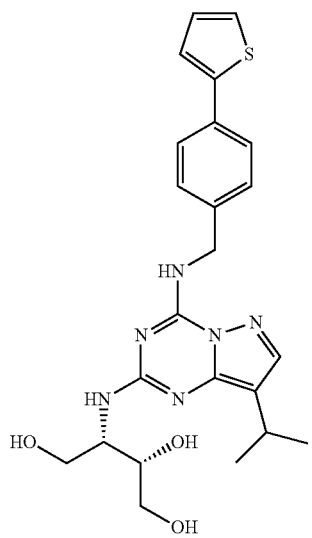

23
-continued
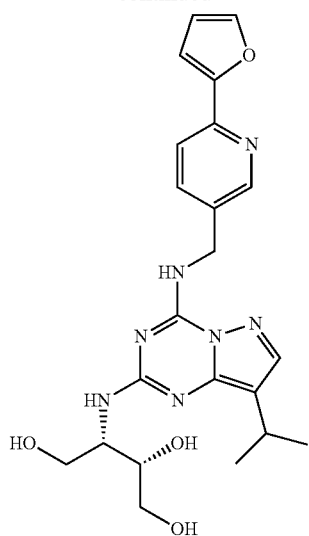
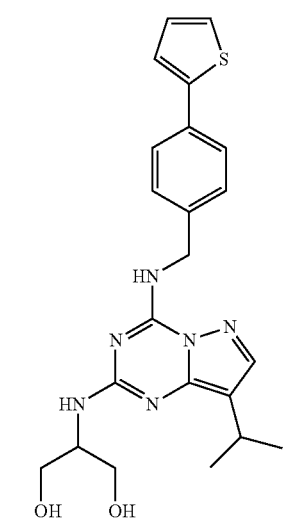
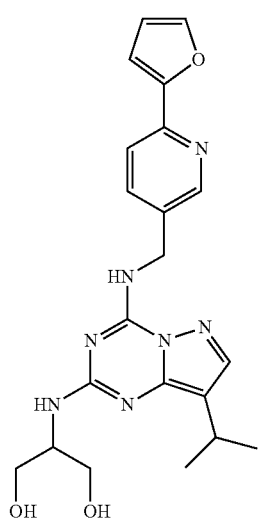
24
-continued
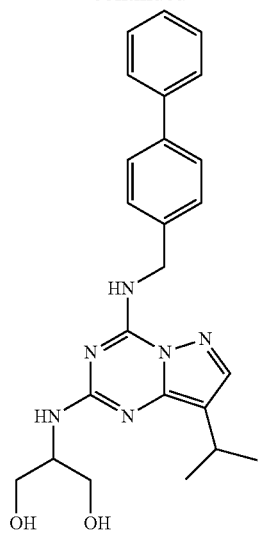
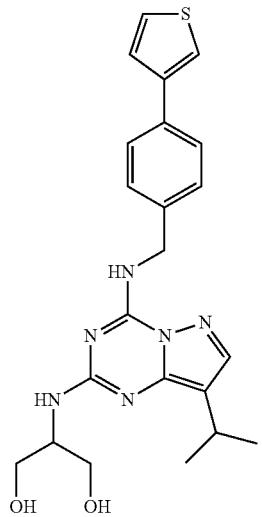
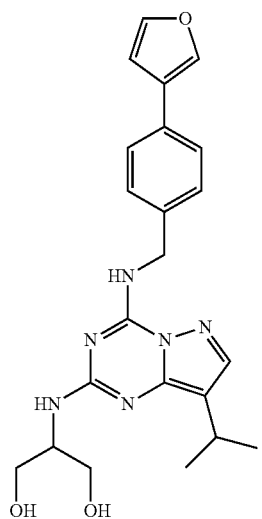

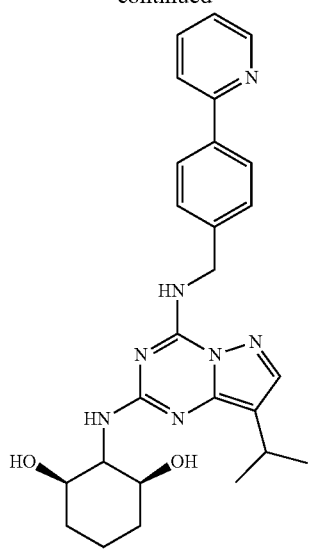
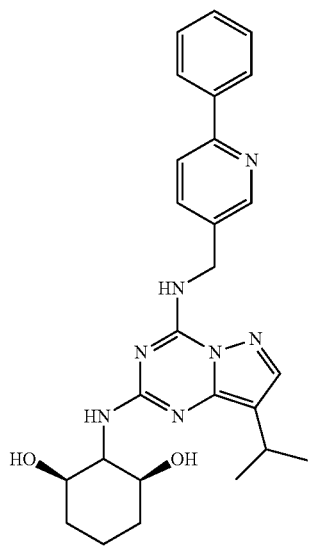
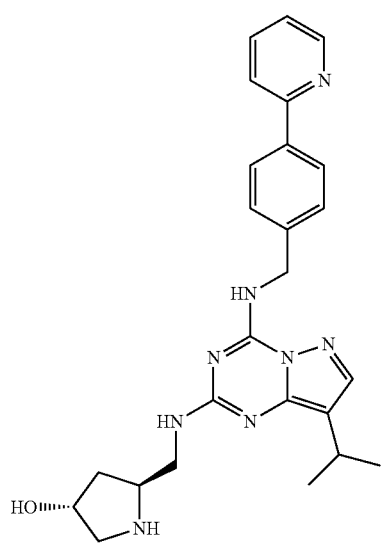
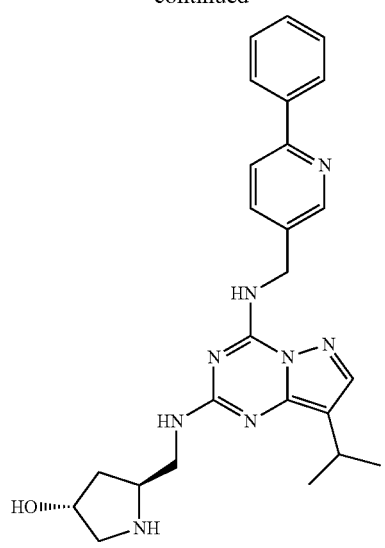

27
-continued
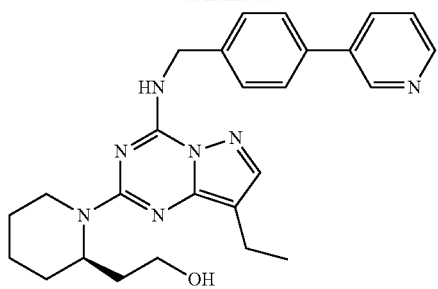
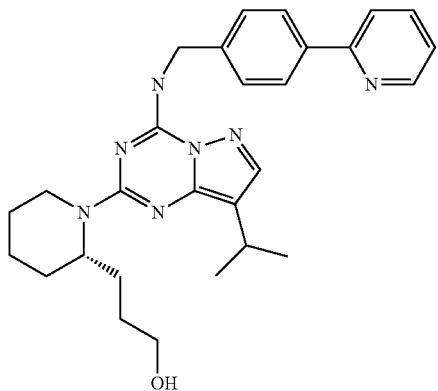
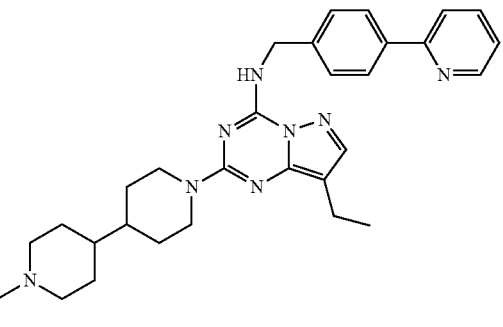
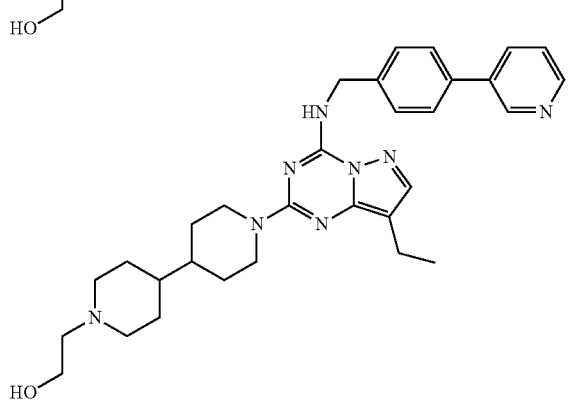
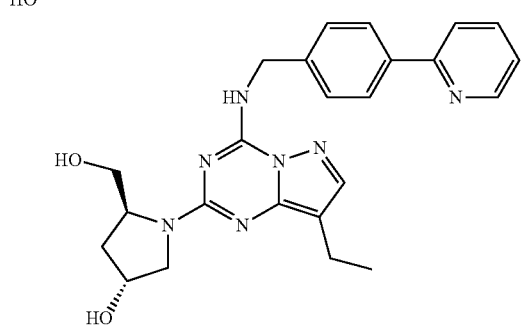
28
-continued
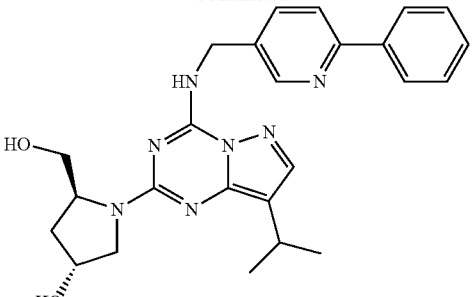
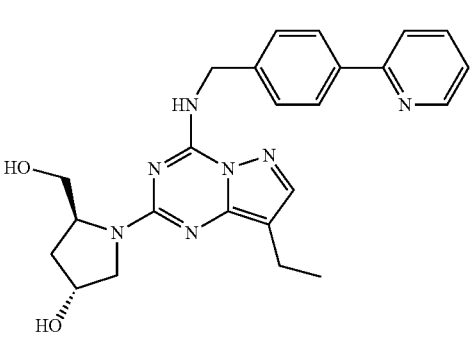
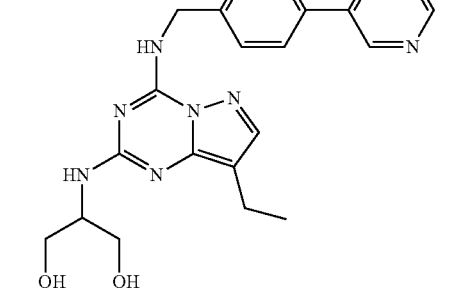
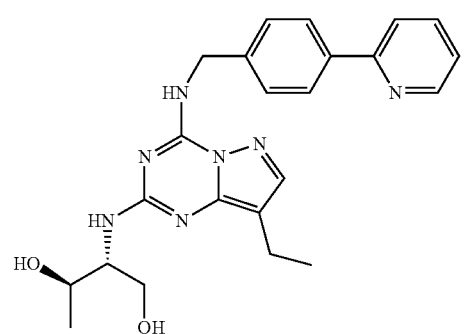
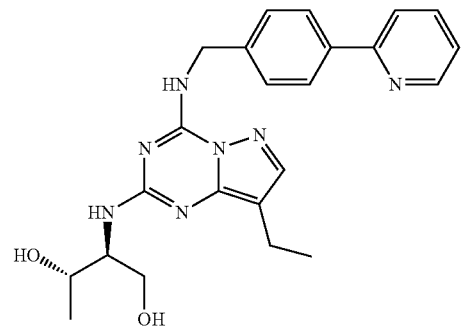

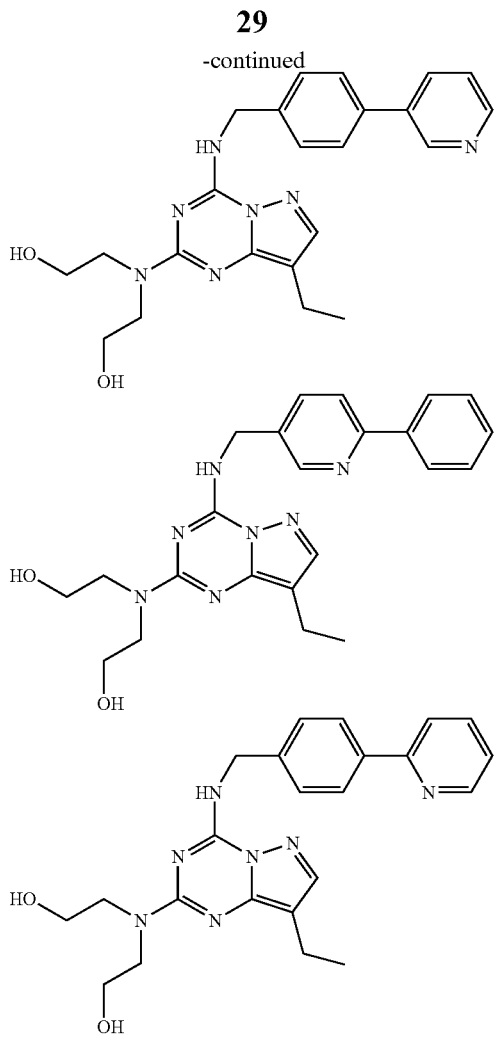

and their salts of pharmaceutically acceptable acids.

The subject of the invention is also a process for preparing the compounds of formula (I).

The compounds of the invention can be prepared according to various methods described according to scheme 1 described below:

Scheme 1

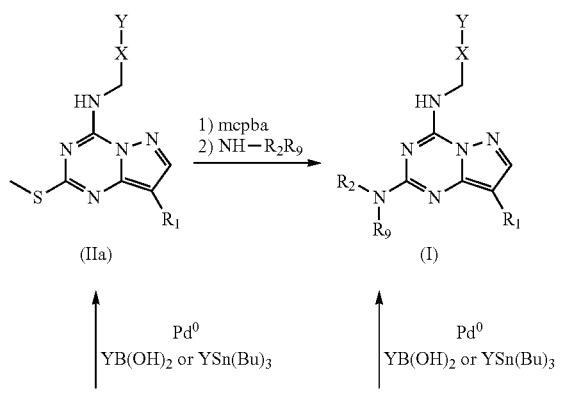

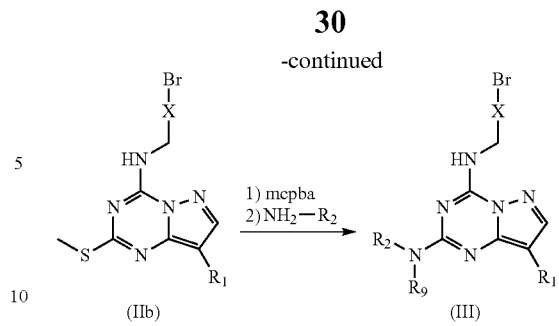

According to scheme 1, the compound of formula (IIa), where X, Y and $R_1$ are as defined above, is subjected to an oxidation reaction in the presence of meta-chloroperbenzoic acid (mcpba) for example in dichloromethane at 0° C., so as to produce the corresponding sulfone. The latter is used directly in an aromatic nucleophilic substitution reaction ($NS_{AR}$) in the presence of a primary amine of formula $NH—R_2R_9$, where $R_2$ and $R_9$ are as defined above, at a temperature ranging from 100 to 180° C., for example at 140° C., so as to produce the compound of formula (I). Alternatively, the compounds of type (I) can also be prepared from the compounds of formula (IIb). These compounds (IIb), where X and $R_1$ are as defined above, are initially used in a coupling reaction catalyzed by a metal, for instance palladium (Suzuki-Miyaura reaction or Stille reaction) or nickel, so as to give intermediates (IIa). These same compounds (IIb) can be oxidized in the presence of meta-chloroperbenzoic acid in dichloromethane at 0° C. so as to produce the sulfone which is displaced by a primary amine ($NS_{AR}$) so as to give the compounds of formula (III). The latter, subjected to a coupling reaction catalyzed by a metal, for instance palladium or nickel, produce the compounds of formula (I).

Thus, according to one of its aspects, the present invention relates to a process for preparing a compound of formula (I) in accordance with the invention, characterized in that a compound of formula (IIa) which follows:

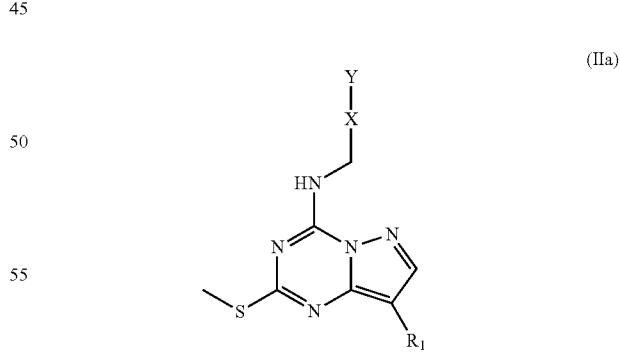

in which X, Y and $R_1$ are as defined above, is reacted with meta-chloroperbenzoic acid in an oxidation reaction, and in that the sulfone obtained is used directly in a nucleophilic substitution reaction in the presence of a primary amine of formula $NH_2R_2$, where $R_2$ is as defined above, at a temperature ranging from 100 to 180° C., for example at 140° C., so as to produce the compound of formula (I), or else in that a compound of formula (IIb)

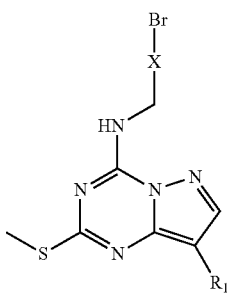

(IIb)

Scheme 2

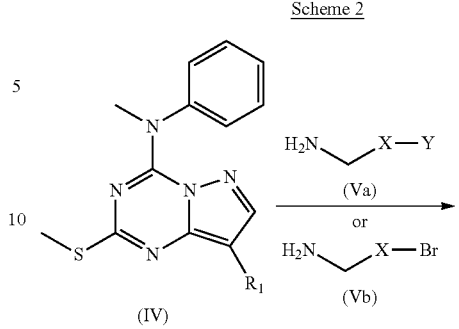

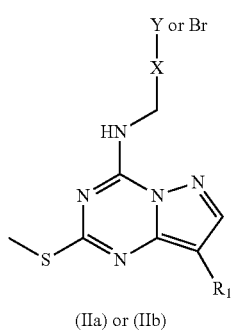

(IIa) or (IIb)

in which X and $R_1$ are as defined above, is reacted with a metal, for instance palladium or nickel, so as to give a compound of formula (IIa) as defined above, or alternatively in that a compound of formula (IIb) as defined above is reacted with meta-chloroperbenzoic acid in an oxidation reaction, the sulfone obtained being directly used in a nucleophilic substitution reaction in the presence of a primary amine of formula NH—$R_2R_9$, where $R_2$ and $R_9$ are as defined above, so as to give a compound of formula (III):

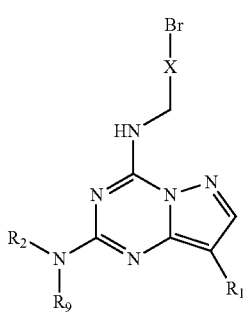

(III)

in which $X_1$, $R_1$ and $R_2$ are as defined above, which is subjected to a coupling reaction catalyzed by a metal, for instance palladium or nickel, so as to produce a compound of formula (I).

The methods for preparing the derivatives of formula (IIa) or (IIb) which are used to prepare the compounds of formula (I) of the invention are described hereinafter.

The derivatives of formula (IIa) or (IIb) can be prepared from the compounds (IV) by the method described in the document "pyrazolo[1,5-a]-1,3,5-triazine as a purine bioisostere: access to potent cyclin-dependent kinase inhibitor (R)-roscovitine analogue", *J. Med. Chem.* 2009, 52, 655.

Generally, the 4-(N-methyl-N-phenylamino)-2-thiomethylpyrazolo[1,5-a]-1,3,5-triazines substituted in position 8 (IV), where $R_1$ is as defined above, are reacted with the aryl- or heteroarylmethyleneamines (V), where X and Y are as defined above, at a temperature ranging from 100 to 180° C., for example at 140° C., so as to produce the compounds of formula (IIa) or (IIb) according to scheme 2 described below:

The compounds of formula (IV), when they are not commercially available, can be prepared using the processes described in the literature, for example in the publication "pyrazolo[1,5-a]-1,3,5-triazine as a purine bioisostere: access to potent cyclin-dependent kinase inhibitor (R)-roscovitine analogue", mentioned above.

The compounds of formula (V), when they are not commercially available, can be prepared using the processes described in the literature, for example in the publication WO 2003/022805.

In the general synthesis schemes 1 and 2, the starting compounds and the reactants, when the method for preparing them is not described, are commercially available or described in the literature, or else can be prepared according to methods which are described therein or which are known to those skilled in the art.

The subject of the invention, according to another of its aspects, is also the compounds of formula (II)

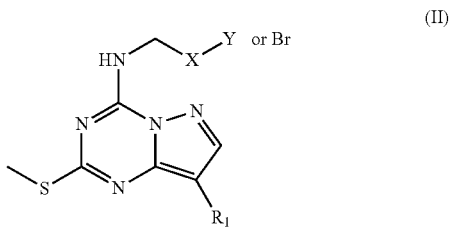

(II)

in which:
X, Y and $R_1$ are as defined above.
These compounds are of use as intermediates for the synthesis of the compounds of formula (I). Examples of compounds of formula (II) are given in table 1 hereinafter.

The examples which follow also describe the preparation of compounds of formula (I) in accordance with the invention. These examples are not limiting and merely illustrate the invention. The numbers of the compounds exemplified refer

I. PREPARATION OF INTERMEDIATES

Preparation I.1

8-isopropyl-2-(methylsulfanyl)-4-(4-phenylbenzylamino)pyrazolo[1,5-a]-1,3,5-triazine (IIa.1)

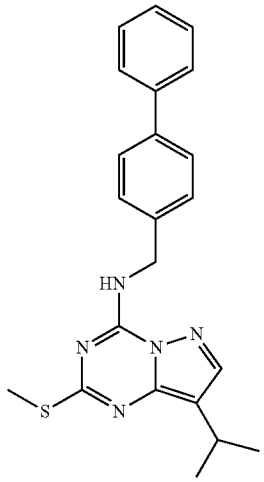 [SMILES: CSc1nc(NCc2ccc(-c3ccccc3)cc2)n2ncc(C(C)C)c2n1]

In a sealed tube, a solution of 8-isopropyl-4-(N-methyl-N-phenylamino)-2-(methylsulfanyl)pyrazolo[1,5-a]-1,3,5-triazine (114 mg, 0.36 mmol) and of 4-phenylbenzylamine (100 mg, 0.55 mmol) is heated at 140° C. for 24 h. After cooling, the solvent is evaporated off. The crude compound collected is purified by flash chromatography (EP/Et$_2$O 9:1) so as to give IIa.1 (95 mg, 67%). Mp=134-135° C. (MeOH). $^1$H NMR (300 MHz, CDCl$_3$): δ 7.75 (s, 1H, H$_{arom}$), 7.59-7.56 (m, 4H, H$_{arom}$), 7.45-7.34 (m, 5H, H$_{arom}$), 6.93 (bs, 1H, NH), 4.85 (d, 2H, J=5.7 Hz, CH$_2$), 3.18 (hept, 1H, J=7.2 Hz, CH), 2.58, (s, 3H, CH$_3$), 1.33 (d, 6H, J=7.2 Hz, 2 CH$_3$). MS (EST): m/z 390 (MH').

Preparation I.2

8-isopropyl-2-(methylsulfanyl)-4-[4-(pyridin-2-yl)benzylamino]pyrazolo[1,5-a]-1,3,5-triazine (IIa.2)

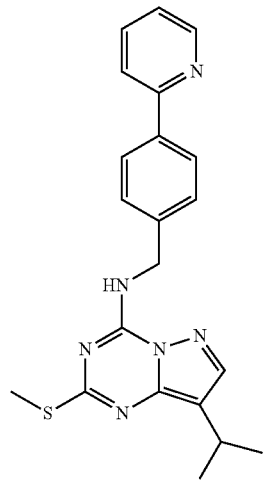 [SMILES: CSc1nc(NCc2ccc(-c3ccccn3)cc2)n2ncc(C(C)C)c2n1]

According to the same conditions resulting in the preparation of the compound IIa.1, the compound IIa.2 is prepared from 8-isopropyl-4-(N-methyl-N-phenylamino)-2-(methylsulfanyl)pyrazolo[1,5-a]-1,3,5-triazine and from 4-(pyridin-2-yl)benzylamine. Yield=60%. Mp=136-138° C. (EtOH). $^1$H NMR (300 MHz, CDCl$_3$): δ 8.71 (d, 1H, J=4.7 Hz, H$_{arom}$), 8.00 (d, 2H, J=8.1 Hz, H$_{arom}$), 7.82-7.72 (m, 3H, H$_{arom}$), 7.49 (d, 2H, J=8.1 Hz, H$_{arom}$), 7.26 (dd, 1H, J=4.7 Hz, 7.2 Hz, H$_{arom}$), 6.76 (bs, 1H, NH), 4.86 (d 2H, J=6.0 Hz, CH$_2$), 3.16 (hept, 1H, J=7.0 Hz, CH), 2.57 (s, 3H, CH$_3$), 1.33 (d, 6H, J=7.0 Hz, 2 CH$_3$). MS (ESI): m/z 391 (MH$^+$).

Preparation I.3

8-isopropyl-2-(methylsulfanyl)-4-[4-(thiophen-3-yl)benzylamino]pyrazolo[1,5-a]-1,3,5-triazine

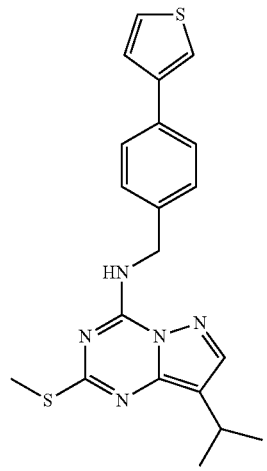 [SMILES: CSc1nc(NCc2ccc(-c3ccsc3)cc2)n2ncc(C(C)C)c2n1]

According to the same conditions resulting in the preparation of the compound IIa.1, the compound IIa.3 is prepared from 8-isopropyl-4-(N-methyl-N-phenylamino)-2-(methylsulfanyl)pyrazolo[1,5-a]-1,3,5-triazine and from 4-(thiophen-3-yl)benzylamine. Yield=74%. Mp=141-143° C. (EtOH). $^1$H NMR (300 MHz, CDCl$_3$): δ 7.73 (s, 1H, H$_{arom}$), 7.57 (d, 2H, J=8.3 Hz, H$_{arom}$), 7.45-7.36 (m, 5H, H$_{arom}$), 6.78 (bs, 1H, NH), 4.81 (d, 2H, J=6.0 Hz, CH$_2$), 3.16 (hept, 1H, J=7.0 Hz, CH), 2.58 (s, 3H, CH$_3$), 1.33 (d, 6H, J=7.0 Hz, 2 CH$_3$). MS (ESI): m/z 396 (MH$^+$).

Preparation I.4

4-(4-bromobenzylamino)-8-isopropyl-2-(methylsulfanyl)pyrazolo[1,5-a]-1,3,5-triazine (IIb.4)

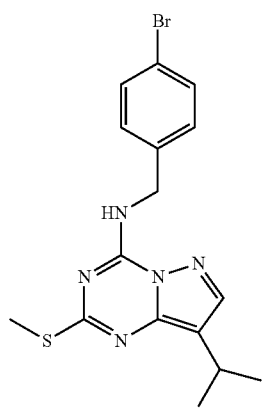 [SMILES: CSc1nc(NCc2ccc(Br)cc2)n2ncc(C(C)C)c2n1]

According to the same conditions resulting in the preparation of the compound IIa.2, the compound IIb.4 is prepared from 8-isopropyl-4-(N-methyl-N-phenylamino)-2-(methylsulfanyl)pyrazolo[1,5-a]-1,3,5-triazine and from 4-bromobenzylamine. Yield=75%. Mp=171-172° C. (EtOH). $^1$H NMR (300 MHz, CDCl$_3$): δ 7.74 (s, 1H, H$_{arom}$), 7.47 (d, 2H, J=8.3 Hz, H$_{arom}$), 7.24 (d, 2H, J=8.3 Hz, H$_{arom}$), 6.76 (bs, 1H, NH), 4.75 (d, 2H, J=6.0 Hz, CH$_2$), 3.15 (hept, 1H, J=6.8 Hz, CH), 2.56 (s, 3H, CH$_3$), 1.33 (d, 6H, J=6.8 Hz, 2 CH$_3$). MS (ESI): m/z 394 (Br$^{81}$, MH$^+$), 392 (Br$^{79}$, MH$^+$).

Preparation I.5

(R)-2-(1-hydroxybut-2-ylamino)-4-(4-bromobenzylamino)-8-isopropylpyrazolo[1,5-a]-1,3,5-triazine (III.5)

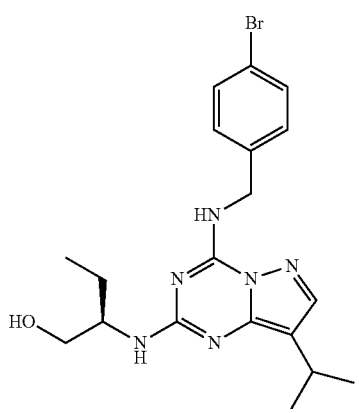 [SMILES: CC[C@H](CO)Nc1nc(NCc2ccc(Br)cc2)n2ncc(C(C)C)c2n1]

A solution of IIb.4 (200 mg, 0.51 mmol) in dichloromethane (CH$_2$Cl$_2$) (6 ml) is stirred at 0° C. 70-75% metachloroperbenzoïc acid (126 mg, 0.51 mmol) is added, and then the solution is stirred for 1 h. The same amount of acid is added a second time. The final solution is stirred for 2 h at 0° C. After the addition of a solution of NaHCO$_3$, liquid-liquid extraction is carried out. The isolated organic phase is washed with a solution of NaCl, dried over MgSO$_4$, and then evaporated under reduced pressure. The sulfone is obtained with a quantitative yield, and then used in the following step without further purification. A solution of sulfone (216 mg, 0.51 mmol) and of commercial (R)-(−)-2-aminobutanol (247 μl, 2.62 mmol) is heated at 140° C. for 24 h. After cooling, the solvent is evaporated off. The crude compound collected is purified by flash chromatography (EP/EtOAc 9:1 to 6:4) so as to give III.5 (103 mg, 47%). Oil. $^1$H NMR (300 MHz, CDCl$_3$): δ 7.57 (s, 1H, H$_{arom}$), 7.42 (d, 2H, J=8.3 Hz, H$_{arom}$), 7.15 (d, 2H, J=8.3 Hz, H$_{arom}$), 7.10 (bs, 1H, NH), 5.15 (bs, 1H, NH), 4.61 (d, 2H, J=6.0 Hz, CH$_2$), 3.93-3.61 (m, 3H, CH+CH$_2$), 3.00 (hept, 1H, J=6.8 Hz, CH), 1.70-1.52 (m, 2H, CH$_3$), 1.25 (d, 6H, J=6.8 Hz, 2 CH$_3$), 1.00 (t, 3H, J=7.4 Hz, CH$_3$). MS (ESI): m/z 435 (Br$^{81}$, MH$^+$), 433 (Br$^{79}$, MH$^+$).

Preparation I.6

8-isopropyl-2-methylsulfanyl-4-[4-(pyridin-3-yl)benzylamino]pyrazolo[1,5-a]-1,3,5-triazine (IIa.4)

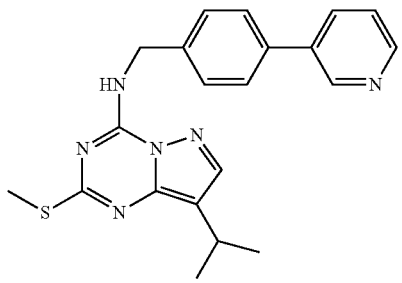 [SMILES: CSc1nc(NCc2ccc(-c3cccnc3)cc2)n2ncc(C(C)C)c2n1]

According to the same conditions resulting in the production of the compound IIa.2, the compound IIa.4 is obtained from 8-isopropyl-4-(N-methyl-N-phenylamino)-2-(methylsulfanyl)pyrazolo[1,5-a]-1,3,5-triazine and from 4-(pyridin-3-yl)benzylamine. Yield=65%. $^1$H NMR (400 MHz, CDCl$_3$): δ 8.83 (s, 1H, H$_{arom}$), 8.60 (d, 1H, H$_{arom}$), 7.88 (d, 1H, H$_{arom}$), 7.76 (s, 1H, H$_{arom}$) 7.58 (d, 2H, H$_{arom}$) 7.51 (d, 2H, H$_{arom}$), 7.42 (m, 1H, H$_{arom}$), 6.78 (t, 1H, NH); 4.87 (d, 2H, J=6.0 Hz, CH$_2$), 3.17 (hept, 1H, J=6.8 Hz, CH), 2.55 (s, 3H, CH$_3$), 1.35 (d, 6H, J=6.8 Hz, 2 CH$_3$). MS (ESI): m/z 391 (MH$^+$).

Preparation I.7

8-isopropyl-2-methylsulfanyl-4-[4-phenyl(pyridin-3-yl)methylamino]pyrazolo[1,5-a]-1,3,5-triazin-4-amine (IIa.5)

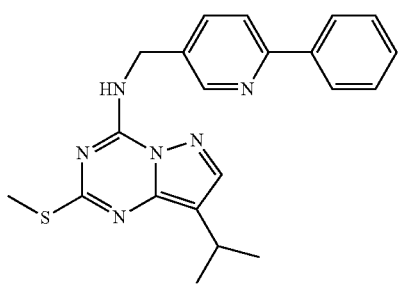 [SMILES: CSc1nc(NCc2ccc(-c3ccccc3)nc2)n2ncc(C(C)C)c2n1]

According to the same conditions resulting in the production of the compound IIa.2, the compound IIa.5 is obtained from 8-isopropyl-4-(N-methyl-N-phenylamino)-2-(methylsulfanyl)pyrazolo[1,5-a]-1,3,5-triazine and from (6-phenylpyridin-3-yl)methanamine. ¹H NMR (400 MHz, CDCl₃): δ 8.71 (s, 1H, H$_{arom}$), 7.98 (m, 3H, H$_{arom}$), 7.75 (m, 3H, H$_{arom}$), 7.45 (m, 2H, H$_{arom}$), 6.85 (t, 1H, NH), 4.85 (d, 2H, J=6.0 Hz, CH₂), 3.15 (hept, 1H, J=6.8 Hz, CH), 1.70 (s, 3H, CH₃), (d, 6H, J=6.8 Hz, 2 CH₃). MS (ESI): m/z 391 (MH⁺).

TABLE I

| Preparation No. | R₁ | R₂ | X | Y | Mp (° C.) and/or mass (m/z) |
|---|---|---|---|---|---|
| IIa.1 | isoPr | —SMe | 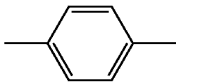 | 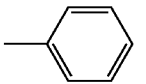 | Mp = 134-135<br>MH⁺ = 390 |
| IIa.2 | isoPr | —SMe | 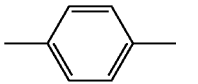 | 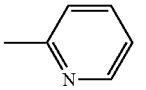 | Mp = 136-138<br>MH⁺ = 391 |
| IIa.3 | isoPr | —SMe | 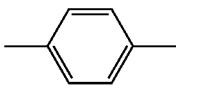 | 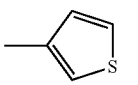 | Mp = 141-143<br>MH⁺ = 396 |
| IIb.4 | isoPr | —SMe | 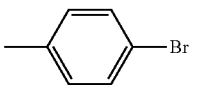 | / | Mp = 171-172<br>MH⁺ = 394 |
| III.5 | isoPr | 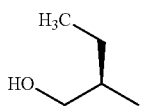 | 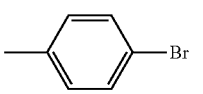 | / | MH⁺ = 435 |
| IIIa.4 | isoPr | —SMe | 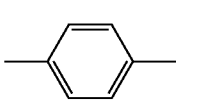 | 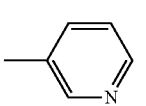 | MH⁺ = 391 |
| IIIa.5 | isoPr | —SMe | 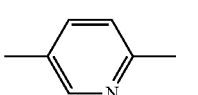 | 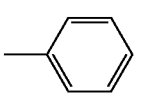 | MH⁺ = 391 |

The examples which follow illustrate the invention without limiting it.

II. PREPARATION OF THE COMPOUNDS OF FORMULA (I)

Example 1

(R)-2-(1-hydroxybut-2-ylamino)-8-isopropyl-4-phenylbenzylamino)pyrazolo[1,5-a]-1,3,5-triazine (1)

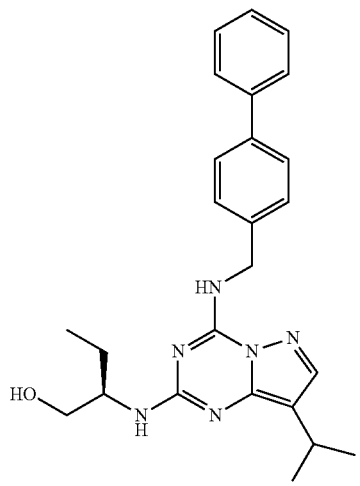 [SMILES: CC[C@H](CO)Nc1nc(NCc2ccc(-c3ccccc3)cc2)n2ncc(C(C)C)c2n1]

A solution of IIa.1 (160 mg, 0.41 mmol) in $CH_2Cl_2$ (4 ml) is stirred at 0° C. 70-75% meta-chloroperbenzoic acid (100 mg, 0.41 mmol) is added, and then the solution is stirred for 1 h. The same amount of acid is added a second time. The final solution is stirred for 2 h at 0° C. After the addition of a solution of $NaHCO_3$, liquid-liquid extraction is carried out. The isolated organic phase is washed with a solution of NaCl, dried over $MgSO_4$, and then evaporated under reduced pressure. The sulfone is obtained with a quantitative yield, and is then used in the following step without further purification. A solution of 8-isopropyl-2-(methylsulfonyl)-4-[N-(4-phenyl)benzylamino]pyrazolo[1,5-a]-1,3,5-triazine (173 mg, 0.41 mmol) and of commercial (R)-(−)-2-aminobutanol (193 µl, 2.03 mmol) is heated at 140° C. for 24 h. After cooling, the solvent is evaporated off. The crude compound collected is purified by flash chromatography (EP/EtOAc 8:2, then 1:1) so as to give 1 (75 mg, 43%). Oil. $^1H$ NMR (300 MHz, $CDCl_3$): δ 7.63 (s, 1H, $H_{arom}$) 7.59-7.56 (m, 4H, $H_{arom}$), 7.47-7.33 (m, 5H, $H_{arom}$), 6.74 (bs, 1H, NH), 4.78-4.75 (m, 2H, $CH_2$), 3.94-3.96 (bs, 1H, CH), 3.82 (d, 1H, J=10.8 Hz, $CH_2$), 3.68 (dd, 1H, J=7.3, 10.8 Hz, $CH_2$), 3.02 (hept, 1H, J=6.6 Hz, CH), 1.70-1.52 (m, 2H, $CH_2$), 1.28 (d, 6H, J=6.8 Hz, 2 $CH_3$), 1.03 (t, 3H, J=7.4 Hz, $CH_3$). MS (ESI): m/z 431 (MH$^+$).

Example 2

(R)-2-(1-hydroxybut-2-ylamino)-8-isopropyl-4-[4-(pyridin-2-yl)benzylamino]pyrazolo[1,5-a]-1,3,5-triazine (2)

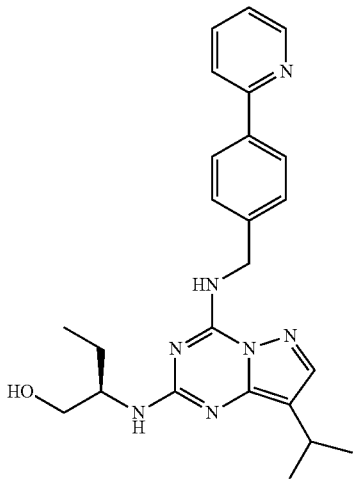 [SMILES: CC[C@H](CO)Nc1nc(NCc2ccc(-c3ccccn3)cc2)n2ncc(C(C)C)c2n1]

A solution of IIa.2 (400 mg, 1.02 mmol) in $CH_2Cl_2$ (12 ml) is stirred at 0° C. 70-75% meta-chloroperbenzoic acid (250 mg, 1.02 mmol) is added, and then the solution is stirred for 1 h. The same amount of acid is added a second time. The final solution is stirred for 2 h at 0° C. After the addition of a solution of $NaHCO_3$, liquid-liquid extraction is carried out. The isolated organic phase is washed with a solution of NaCl, dried over $MgSO_4$, and then evaporated under reduced pressure. The sulfone is obtained with a quantitative yield, and is then used in the following step without further purification. A solution of sulfone (430 mg, 1.02 mmol) and of commercial (R)-(−)-2-aminobutanol (482 µl, 5.09 mmol) is heated at 140° C. for 12 h. After cooling, the solvent is evaporated off. The crude compound collected is purified by flash chromatography (EP/EtOAc 9:1 to 6:4) so as to give 2 (200 mg, 45%). Foam. $^1H$ NMR (300 MHz, $CDCl_3$): δ 8.69 (d, 1H, J=4.1 Hz, $H_{arom}$), 7.96 (d, 2H, J=7.9 Hz, $H_{arom}$), 7.78-7.69 (m, 2H, $H_{arom}$), 7.62 (s, 1H, $H_{arom}$) 7.42 (d, 2H, J=7.9 Hz, $H_{arom}$), 7.26-7.21 (m, 1H, $H_{arom}$), 6.91 (bs, 1H, NH), 5.10 (s, 1H, H exchangeable), 4.75 (d, 2H, J=6.0 Hz, $CH_2$), 3.93 (bs, 1H, CH), 3.83-3.62 (m, 2H, $CH_2$), 3.02 (hept, 1H, J=6.8 Hz, CH), 1.70-1.52 (m, 2H, $CH_2$), 1.27 (d, 6H, J=6.8 Hz, 2 $CH_3$), 1.02 (t, 3H, J=7.4 Hz, $CH_3$). MS (ESI): m/z 432 (MH$^+$).

Example 3

(R)-2-(1-hydroxybut-2-ylamino)-8-isopropyl-4-[4-(pyridin-2-yl)benzylamino]pyrazolo[1,5-a]-1,3,5-triazine (2)

In a sealed tube, the compound III.5 (103 mg, 0.24 mmol) is added to a degassed solution of tri-n-butyl(pyridin-2-yl)stannane (177 mg, 0.48 mmol) and of Pd(PPh$_3$)$_4$ (23 mg, 0.02 mmol) in toluene (10 ml). The degassed final solution is heated at 110° C. overnight. After cooling and dilution with a solution of $NaHCO_3$, the solution is extracted with $CH_2Cl_2$ (3×12 ml). The isolated organic phase is washed with a solution of NaCl. After drying over $MgSO_4$, the solvent is evaporated off under reduced pressure. The residue is purified by flash chromatography (EP/EtOAc 9:1 to 6:4) so as to give 2 (35 mg, 34%). Foam, $^1$H NMR (300 MHz, CDCl$_3$): δ 8.69 (d, 1H, J=4.1 Hz, H$_{arom}$), 7.96 (d, 2H, J=7.9 Hz, H$_{arom}$), 7.78-7.69 (m, 2H, H$_{arom}$), 7.62 (5, 1H, H$_{arom}$), 7.42 (d, 2H, J=7.9 Hz, H$_{arom}$), 7.26-7.21 (m, 1H, H$_{arom}$), 6.91 (bs, 1H, NH), 5.10 (s, 1H, H exchangeable), 4.75 (d, 2H, J=6.0 Hz, CH$_2$), 3.93 (bs, 1H, CH), 3.83-3.62 (m, 2H, CH$_2$), 3.02 (hept, 1H, J=6.8 Hz, CH), 1.70-1.52 (m, 2H, CH$_2$), 1.27 (d, 6H, J=6.8 Hz, 2 CH$_3$), 1.02 (t, 3H, J=7.4 Hz, CH$_3$). MS (ESI): m/z 432 (MH$^+$).

Example 4

(R)-2-(1-hydroxybut-2-ylamino)-8-isopropyl-4-[4-(pyridin-2-yl)benzylamino]pyrazolo[1,5-a]-1,3,5-triazine fumarate (3)

The product 2 is treated with fumaric acid in an EtOH/Et$_2$O solution. The fumaric acid salt 3 crystallizes from the reaction medium at 0° C. Mp=175-177° C. $^1$H NMR (300 MHz, DMSO-d$_6$): δ 13.12 (bs, 2H, OH), 8.70 (bs, 1H, NH), 8.64 (d, 1H, J=4.1 Hz, H$_{arom}$), 8.03 (d, 2H, J=8.3 Hz, H$_{arom}$), 7.92 (d, 1H, J=8.0 Hz, H$_{arom}$), 7.86 (t, 1H, J=8.0 Hz, H$_{arom}$), 7.70 (s, 1H, H$_{arom}$), 7.48 (broad d, 2H, J=8.3 Hz, H$_{arom}$) 7.35-7.31 (m, 1H, H$_{arom}$) 6.62 (s, 2H, =CH), 6.51 (bs, 1H, NH), 4.67 (bs, 2H, CH$_2$), 4.51 (bs, 1H, OH), 3.82 (bs, 1H, CH), 3.45-3.32 (m, 2H, CH$_2$), 2.90 (hept, 1H, J=6.8 Hz, CH), 1.65-1.35 (m, 2H, CH$_2$), 1.23 (d, 6H, J=6.8 Hz, 2 CH$_3$), 0.84 (t, 3H, J=7.4 Hz, CH$_3$).

Example 5

(S)-2-(1-hydroxybut-2-ylamino)-8-isopropyl-4-[4-(pyridin-2-yl)benzylamino]pyrazolo[1,5-a]-1,3,5-triazine (4)

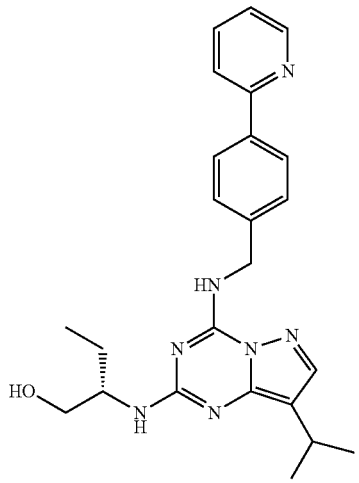 [SMILES: CC[C@@H](CO)Nc1nc(NCc2ccc(-c3ccccn3)cc2)n2ncc(C(C)C)c2n1]

According to the same conditions resulting in the preparation of the compound 2, the compound 4 is prepared from IIa.2 by oxidation reaction of the sulfur atom and then introduction of commercial (S)-(+)-2-aminobutanol. Yield=48%. Foam. $^1$H NMR (300 MHz, CDCl$_3$): δ 8.69 (d, 1H, J=4.1 Hz, H$_{arom}$), 7.96 (d, 2H, J=7.9 Hz, H$_{arom}$), 7.78-7.69 (m, 2H, H$_{arom}$), 7.62 (s, 1H, H$_{arom}$), 7.42 (d, 2H, J=7.9 Hz, H$_{arom}$), 7.26-7.21 (m, 1H, H$_{arom}$), 6.91 (bs, 1H, NH), 5.10 (s, 1H, H exchangeable), 4.75 (d, 2H, J=6.0 Hz, CH$_2$), 3.93 (bs, 1H, CH), 3.83-3.62 (m, 2H, CH$_2$), 3.02 (hept, 1H, J=6.8 Hz, CH), 1.70-1.52 (m, 2H, CH$_2$), 1.27 (d, 6H, J=6.8 Hz, 2 CH$_3$), 1.02 (t, 3H, J=7.4 Hz, CH$_3$). MS (ESI): m/z 432 (MH$^+$).

Example 6

(S)-2-(1-hydroxybut-2-ylamino)-8-isopropyl-4-[4-(pyridin-2-yl)benzylamino]pyrazolo[1,5-a]-1,3,5-triazine fumarate (5)

The product 4 is treated with fumaric acid in an EtOH/Et$_2$O solution. The fumaric acid salt 5 crystallizes from the reaction medium. Mp=175-177° C. $^1$H NMR (300 MHz, DMSO-d$_6$): δ 13.12 (bs, 2H, OH), 8.71 (bs, 1H, NH), 8.64 (d, 1H, J=4.1 Hz, H$_{arom}$), 8.03 (d, 2H, J=8.3 Hz, H$_{arom}$), 7.92 (d, 1H, J=8.0 Hz, H$_{arom}$), 7.86 (t, 1H, J=8.0 Hz, H$_{arom}$) 7.70 (s, 1H, H$_{arom}$), 7.48 (d, 2H, J=8.3 Hz, H$_{arom}$), 7.35-7.31 (m, 1H, H$_{arom}$), 6.62 (s, 2H, =CH), 6.51 (bs, 1H, NH), 4.67 (bs, 2H, CH$_2$), 4.51 (bs, 1H, OH), 3.82 (bs, 1H, CH), 3.45-3.32 (m, 2H, CH$_2$), 2.90 (hept, 1H, J=6.8 Hz, CH), 1.65-1.35 (m, 2H, CH$_2$), 1.23 (d, 6H, J=6.8 Hz, 2 CH$_3$), 0.84 (t, 3H, J=7.4 Hz, CH$_3$).

Example 7

(R)-2-(1-hydroxybut-2-ylamino)-8-isopropyl-4-[4-(thiophen-3-yl)benzylamino]pyrazolo[1,5-a]-1,3,5-triazine (6)

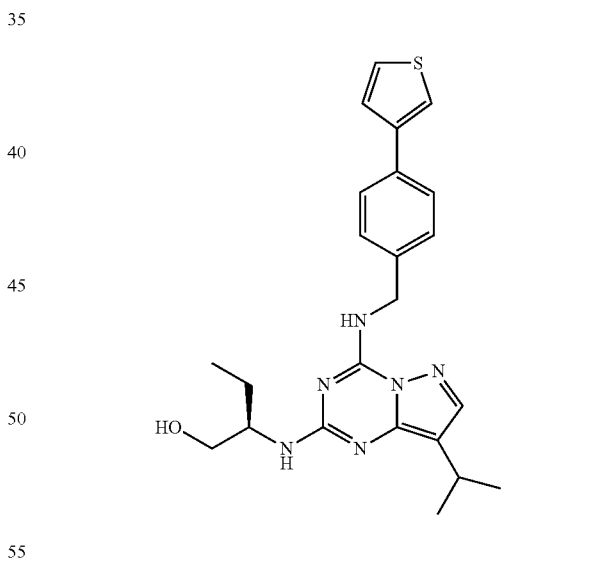

According to the same conditions resulting in the preparation of the compound 2, the compound 6 is prepared from IIa.3 by oxidation reaction of the sulfur atom and then introduction of commercial (R)-(−)-2-aminobutanol. Yield=50%. Oil. $^1$H NMR (300 MHz, CDCl$_3$): δ 7.61 (s, 1H, H$_{arom}$), 7.57 (d, 2H, J=8.3 Hz, H$_{arom}$), 7.44 (bs, 1H, H$_{arom}$), 7.40-7.34 (m, 4H, H$_{arom}$), 6.83 (bs, 1H, NH), 5.10 (bs, 1H, H exchangeable), 4.72 (d, 2H, J=6.0 Hz, CH$_2$), 4.00-3.92 (m, 1H, CH), 3.83 (d, 1H, J=10.7 Hz, CH$_2$), 3.66 (dd, 1H, J=7.3, 10.7 Hz, CH$_2$), 3.02 (hept, 1H, J=6.8 Hz, CH), 1.70-1.52 (m, 2H, CH$_2$), 1.27 (d, 6H, J=6.8 Hz, 2 CH$_3$), 1.03 (t, 3H, J=7.4 Hz, CH$_3$). MS (ESI): m/z 437 (MH$^+$).

Example 8

(R)-2-(1-hydroxybut-2-ylamino)-8-isopropyl-4-[4-(thiophen-3-yl)benzylamino]pyrazolo[1,5-a]-1,3,5-triazine (6)

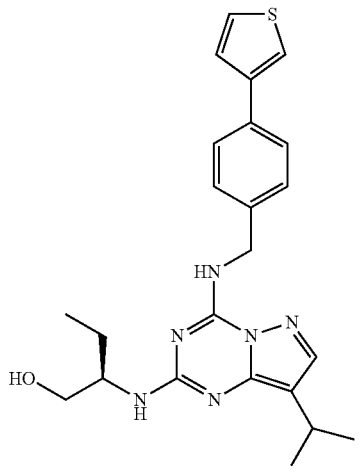 [SMILES: CC[C@H](CO)Nc1nc(NCc2ccc(-c3ccsc3)cc2)n2ncc(C(C)C)c2n1]

In a sealed tube, the compound III.5 (180 mg, 0.41 mmol) is added to a degassed solution of thiophen-3-ylboronic acid (79 mg, 0.62 mmol), of Pd(PPh$_3$)$_4$ (47 mg, 0.04 mmol) and of 2 μM NaHCO$_3$ (2 ml) in toluene (10 ml). The final solution is heated at 140° C. overnight. After cooling and dilution with H$_2$O, the solution is extracted with CH$_2$Cl$_2$ (3×12 ml). The isolated organic phase is washed with a solution of NaCl. After drying over MgSO$_4$, the solvent is evaporated off under reduced pressure. The residue is purified by flash chromatography (EP/EtOAc 9:1 to 6:4) so as to give 6 (90 mg, 50%). Oil. $^1$H NMR (300 MHz, CDCl$_3$): δ 7.61 (s, 1H, H$_{arom}$), 7.57 (d, 2H, J=8.3 Hz, H$_{arom}$) 7.44 (bs, 1H, H$_{arom}$), 7.40-7.34 (m, 4H, H$_{arom}$), 6.80 (bs, 1H, NH), 5.11 (bs, 1H, H exchangeable), 4.72 (d, 2H, J=6.0 Hz, CH$_2$), 4.00-3.92 (m, 1H, CH), 3.83 (d, 1H, J=10.7 Hz, CH$_2$), 3.66 (dd, 1H, J=7.3, 10.7 Hz, CH$_2$) 3.02 (hept, 1H, J=6.8 Hz, CH), 1.70-1.52 (m, 2H, CH$_2$), 1.27 (d, 6H, J=6.8 Hz, 2 CH$_3$), 1.03 (t, 3H, J=7.4 Hz, CH$_3$). MS (EST): m/z 437 (MH$^+$).

Example 9

(S)-2-(1-hydroxybut-2-ylamino)-8-isopropyl-4-[4-(thiophen-3-yl)benzylamino]pyrazolo[1,5-a]-1,3,5

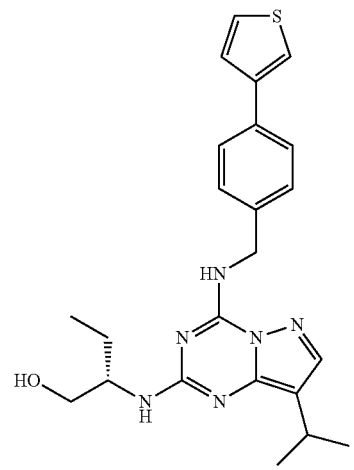 [SMILES: CC[C@@H](CO)Nc1nc(NCc2ccc(-c3ccsc3)cc2)n2ncc(C(C)C)c2n1]

According to the same conditions resulting in the preparation of the compound 2, the compound 6 is prepared from IIa.3 by oxidation reaction of the sulfur atom and then introduction of commercial (S)-(+)-2-aminobutanol. Yield=49%. Oil. $^1$H NMR (300 MHz, CDCl$_3$): δ 7.61 (s, 1H, 7.57 (d, 2H, J=8.3 Hz, H$_{arom}$), 7.44 (bs, 1H, H$_{arom}$), 7.40-7.34 (m, 4H, H$_{arom}$) 6.81 (bs, 1H, NH), 5.08 (bs, 1H, NH), 4.72 (d, 2H, J=6.0 Hz, CH$_2$), 4.00-3.92 (m, 1H, CH), 3.83 (d, 1H, J=10.7 Hz, CH$_2$), 3.66 (dd, 1H, J=7.3, 10.7 Hz, CH$_2$), 3.02 (hept, 1H, J=6.8 Hz, CH), 1.70-1.52 (m, 2H, CH$_2$), 1.27 (d, 6H, J=6.8 Hz, 2 CH$_3$), 1.03 (t, 3H, J=7.4 Hz, CH$_3$).
MS (ESI): m/z 437 (MH$^+$).

Example 10

(S)-2-(1,2-dihydroxypropan-3-ylamino)-8-isopropyl-4-[4-(thiophen-3-yl)benzylamino]pyrazolo[1,5-a]-1,3,5-triazine (8)

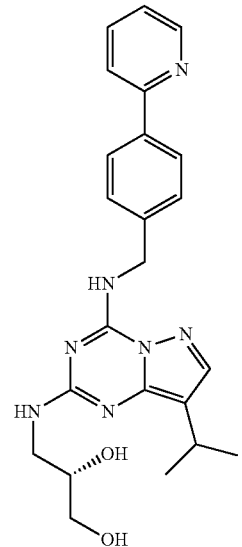 [SMILES: CC(C)c1cnn2c(NCc3ccc(-c4ccccn4)cc3)nc(NC[C@H](O)CO)nc12]

According to the same conditions resulting in the preparation of the compound 2, the compound 8 is prepared from IIa.2 by oxidation reaction of the sulfur atom and then introduction of commercial (S)-3-amino-1,2-propanediol. Yield=20%. Oil. $^1$H NMR (300 MHz, CDCl$_3$): δ 8.69 (d, 1H, J=4.5 Hz, H$_{arom}$), 7.98 (d, 2H, J=8.3 Hz, H$_{arom}$), 7.79-7.70 (m, 2H, H$_{arom}$), 7.66 (s, 1H, H$_{arom}$), 7.45 (d, 2H, J=8.3 Hz, H$_{arom}$), 7.27-7.22 (m, 1H, H$_{arom}$), 6.81 (bs, 1H, NH), 4.78 (d, 2H, J=5.8 Hz, CH$_2$), 3.83-3.79 (m, 1H, CH), 3.65-3.55 (m, 4H, 2 CH$_2$), 3.03 (hept, 1H, J=7.0 Hz, CH), 1.28 (d, 6H, J=7.0 Hz, 2 CH$_3$). MS (ESI): m/z 434 (MH$^+$).

Example 11

(S)-2-(1,2-dihydroxypropan-3-ylamino)-8-isopropyl-4-[4-(pyridin-2-yl)benzylamino]pyrazolo[1,5-a]-1,3,5-triazine fumarate (9)

The product 8 is treated with fumaric acid in an EtOH/Et$_2$O solution. The fumaric acid salt 9 crystallizes from the reaction medium. Mp=168-170° C. $^1$H NMR (300 MHz, CDCl$_3$+1 drop DMSO-d$_6$): δ 8.64 (d, 1H, J=3.8 Hz, H$_{arom}$), 7.93 (d, 2H, J=8.1 Hz, H$_{arom}$), 7.74-7.65 (m, 2H, H$_{arom}$), 7.60 (s, 1H, H$_{arom}$), 7.42 (d, 2H, J=8.1 Hz, H$_{arom}$) 7.26-7.18 (m, 1H, H$_{arom}$), 6.76 (s, 2H, =CH), 4.74 (d, 2H, J=5.9 Hz, CH$_2$), 3.80-3.75 (m, 1H, CH), 3.56-3.45 (m, 4H, 2

CH$_2$), 2.99 (hept, 1H, J=6.8 Hz, CH), 1.23 (d, 6H, J=6.8 Hz, 2 CH$_3$).

Example 12

(R)-2-(1,2-dihydroxypropan-3-ylamino)-8-isopropyl-4-[4-(pyridin-2-yl)benzylamino]pyrazolo[1,5-a]-1,3,5-triazine (10)

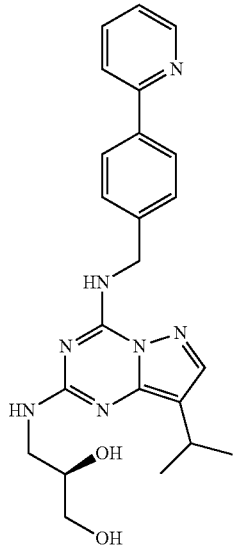

According to the same conditions resulting in the preparation of the compound 2, the compound 10 is prepared from IIa.2 by oxidation reaction of the sulfur atom and then introduction of commercial (R)-3-amino-1,2-propanediol. Yield=35%. Oil. $^1$H NMR (300 MHz, CDCl$_3$): δ 8.69 (d, 1H, J=4.5 Hz, H$_{arom}$), 7.98 (d, 2H, J=8.3 Hz, H$_{arom}$), 7.79-7.70 (m, 2H, H$_{arom}$) 7.66 (s, 1H, H$_{arom}$), 7.45 (d, 2H, J=8.3 Hz, H$_{arom}$), 7.27.28-7.22 (m, 1H, H$_{arom}$), 6.80 (bs, 1H, NB), 4.78 (d, 2H, J=5.8 Hz, CH$_2$), 3.83-3.79 (m, 1H, CH), 3.65-3-3.55 (m, 4H, 2 CH$_2$), 3.03 (hept, 1H, J=7.0 Hz, CH), 1.28 (d, 6H, J=7.0 Hz, 2 CH$_3$). MS (BSI): m/z 434 (MH$^+$).

Example 13

(R)-2-(1,2-dihydroxypropan-3-ylamino)-8-isopropyl-4-[4-(pyridin-2-yl)benzylamino]pyrazolo[1,5-a]-1,3,5-triazine fumarate (11)

The product 10 is treated with fumaric acid in an EtOH/Et$_2$O solution. The fumaric acid salt 11 crystallizes from the reaction medium. Mp=168-170° C. $^1$H NMR (300 MHz, CDCl$_3$ 1 drop DMSO-d$_6$): δ 8.64 (d, 1H, J=3.8 Hz, H$_{arom}$), 7.93 (d, 2H, J=8.1 Hz, H$_{arom}$), 7.74-7.65 (m, 2H, H$_{arom}$), 7.60 (s, 1H, H$_{arom}$), 7.42 (d, 2H, J=8.1 Hz, H$_{arom}$), 7.26-7.18 (m, 1H, H$_{arom}$), 6.76 (s, 2H, =CH), 4.74 (d, 2H, J=5.9 Hz, CH$_2$), 3.80-3.75 (m, 1H, CH), 3.56-3.45 (m, 4H, 2 CH$_2$), 2.99 (hept, 1H, J=6.8 Hz, CH), 1.23 (d, 6H, J=6.8 Hz, 2 CH$_3$).

Example 14

(2R,3R)-2-(1,3-dihydroxybut-2-ylamino)-8-isopropyl-4-[4-(pyridin-2-yl)benzylamino]pyrazolo[1,5-a]-1,3,5-triazine (12)

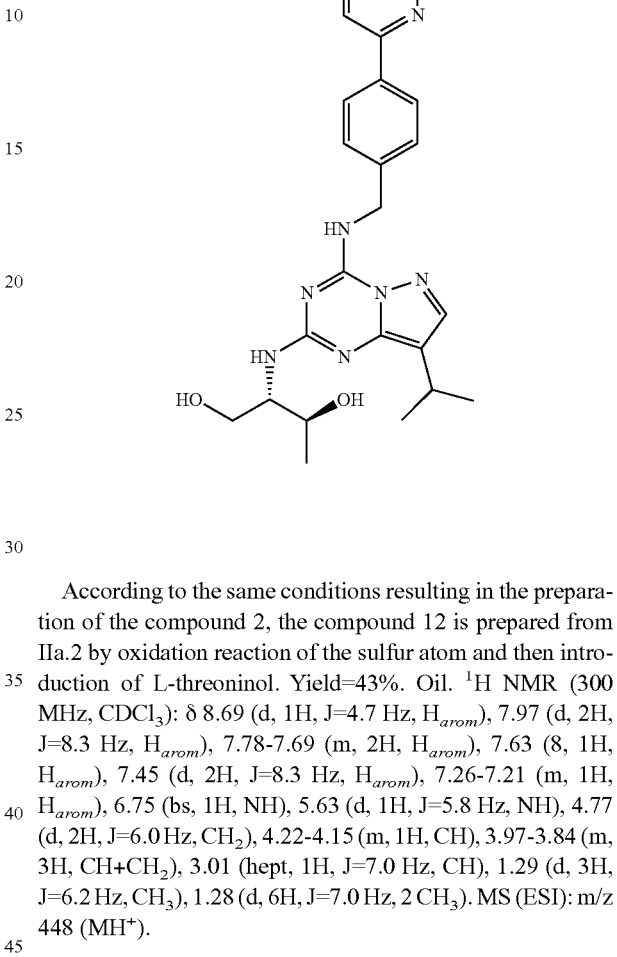

According to the same conditions resulting in the preparation of the compound 2, the compound 12 is prepared from IIa.2 by oxidation reaction of the sulfur atom and then introduction of L-threoninol. Yield=43%. Oil. $^1$H NMR (300 MHz, CDCl$_3$): δ 8.69 (d, 1H, J=4.7 Hz, H$_{arom}$), 7.97 (d, 2H, J=8.3 Hz, H$_{arom}$), 7.78-7.69 (m, 2H, H$_{arom}$), 7.63 (8, 1H, H$_{arom}$), 7.45 (d, 2H, J=8.3 Hz, H$_{arom}$), 7.26-7.21 (m, 1H, H$_{arom}$), 6.75 (bs, 1H, NH), 5.63 (d, 1H, J=5.8 Hz, NH), 4.77 (d, 2H, J=6.0 Hz, CH$_2$), 4.22-4.15 (m, 1H, CH), 3.97-3.84 (m, 3H, CH+CH$_2$), 3.01 (hept, 1H, J=7.0 Hz, CH), 1.29 (d, 3H, J=6.2 Hz, CH$_3$), 1.28 (d, 6H, J=7.0 Hz, 2 CH$_3$). MS (ESI): m/z 448 (MH$^+$).

Example 15

(2R,3R)-2-(1,3-dihydroxybut-2-ylamino)-8-isopropyl-4-[4-(pyridin-2-yl)benzylamino]pyrazolo[1,5-a]-1,3,5-triazine fumarate (13)

The product 12 is treated with fumaric acid in an EtOH/Et$_2$O solution. The fumaric acid salt 13 crystallizes from the reaction medium. Mp=187-189° C. $^1$H NMR (300 MHz, DMSO-d$_6$): δ 13.12 (bs, 2H, OH), 8.77 (bs, 1H, NH), 8.64 (d, 1H, J=4.5 Hz, H$_{arom}$), 8.03 (d, 2H, J=8.1 Hz, H$_{arom}$), 7.94-7.82 (m, 2H, H$_{arom}$), 7.72 (s, 1H, H$_{arom}$) 7.49 (bs, 2H, H$_{arom}$) r 7.35-7.31 (m, 1H, H$_{arom}$), 6.62 (s, 2H, 2 =CH), 6.06 (d, 1H, J=8.7 Hz, NH), 4.73 (bs, 2H, CH$_2$), 4.00-3.89 (bs, 1H, CH), 3.89-3.76 (bs, 1H, CH), 3.58-3.40 (m, 2H, CH$_2$), 2.90 (hept, 1H, J=7.0 Hz, CH), 1.22 (d, 6H, J=5.8 Hz, 2 CH$_3$), 1.04 (bs, 3H, CH$_3$).

Example 16

(2S,3S)-2-(1,3-dihydroxybut-2-ylamino)-8-isopropyl-4-[4-(pyridin-2-yl)benzylamino]pyrazolo[1,5-a]-1,3,5-triazine (14)

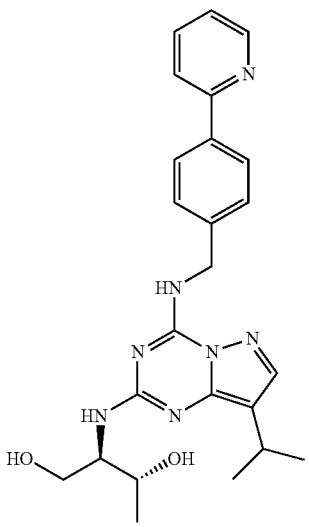 [SMILES: CC(C)c1cnn2c(NCc3ccc(-c4ccccn4)cc3)nc(N[C@H](CO)[C@@H](C)O)nc12]

According to the same conditions resulting in the preparation of the compound 2, the compound 12 is prepared from IIa.2 by oxidation reaction of the sulfur atom and then introduction of D-threoninol. Yield=42%, Oil. $^1$H NMR (300 MHz, CDCl$_3$): δ 8.69 (d, 1H, J=4.7 Hz, H$_{arom}$), 7.97 (d, 2H, J=8.3 Hz, H$_{arom}$), 7.78-7.69 (m, 2H, H$_{arom}$) 7.63 (s, 1H, 1H, H$_{arom}$), 7.45 (d, 2H, J=8.3 Hz, H$_{arom}$), 7.26-7.21 (m, 1H, H$_{arom}$), 6.71 (bs, 1H, NH), 5.62 (d, 1H, J=6.6 Hz, NH), 4.77 (d, 2H, J=6.0 Hz, CH$_2$), 4.22-4.15 (m, 1H, CH), 3.97-3.84 (m, 3H, CH 4-CH$_2$), 3.01 (hept, 1H, J=7.0 Hz, CH), 1.29 (d, 3H, J=6.2 Hz, CH$_3$), 1.28 (d, 6H, J=7.0 Hz, 2 CH$_3$). MS (ESI): m/z 448 (MH$^+$).

Example 17

(2S,3S)-2-(1,3-dihydroxybut-2-ylamino)-8-isopropyl-4-[4-(pyridin-2-yl)benzylamino]pyrazolo[1,5-a]-1,3,5-triazine fumarate (15)

The product 14 is treated with fumaric acid in an EtOH/Et$_2$O solution. The fumaric acid salt 15 crystallizes from the reaction medium. Mp=187-189° C. $^1$H NMR (300 MHz, DMSO-d$_6$): δ 13.12 (bs, 2H, OH), 8.75 (bs, 1H, NH), 8.64 (d, 1H, J=4.5 Hz, H$_{arom}$), 8.03 (d, 2H, J=8.1 Hz, H$_{arom}$), 7.94-7.82 (m, 2H, H$_{arom}$), 7.72 (s, 1H, H$_{arom}$), 7.49 (bs, 2H, H$_{arom}$) 7.35-7.31 (m, 1H, H$_{arom}$), 6.62 (s, 2H, 2 =CH), 6.05 (d, 1H, J=8.7 Hz, NH), 4.67 (bs, 2H, CH$_2$), 4.00-3.89 (bs, 1H, CH), 3.89-3.76 (bs, 1H, CH), 3.58-3.40 (m, 2H, CH$_2$), 2.90 (hept, 1H, J=7.0 Hz, CH), 1.22 (d, 6H, J=5.8 Hz, 2 CH$_3$), 1.04 (bs, 3H, CH$_3$).

Example 18

(2R,3R)-2-(1,3-dihydroxybut-2-ylamino)-8-isopropyl-4-[4-(thiophen-3-yl)benzylamino]pyrazolo[1,5-a]-1,3,5-triazine (16)

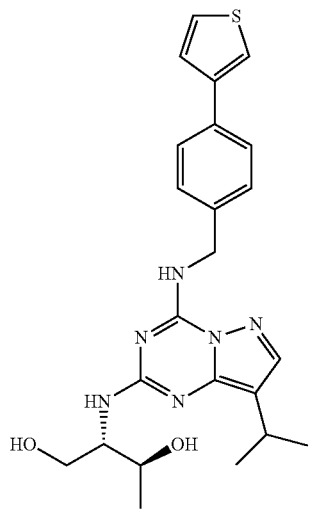 [SMILES: CC(C)c1cnn2c(NCc3ccc(-c4ccsc4)cc3)nc(N[C@@H](CO)[C@H](C)O)nc12]

According to the same conditions resulting in the preparation of the compound 2, the compound 6 is prepared from IIa.3 by oxidation reaction of the sulfur atom and then introduction of commercial L-threoninol.

Yield=40%. Oil. NMR (300 MHz, CDCl$_2$): δ 7.62 (s, 1H, H$_{arom}$), 7.56 (d, 2H, J=8.3 Hz, H$_{arom}$), 7.45-7.43 (m, 1H, H$_{arom}$), 7.40-7.33 (m, 4H, H$_{arom}$), 6.83 (bs, 1H, NH), 5.83 (bs, 1H, NH), 4.71 (d, 2H, J=5.7 Hz, CH$_2$), 4.22-4.15 (m, 1H, CH), 3.97-3.87 (m, 3H, CH+CH$_2$), 3.00 (hept, 1H, J=6.8 Hz, CH), 1.28 (d, 3H, J=6.2 Hz, CH$_3$), 1.27 (d, 6H, J=6.8 Hz, 2 CH$_2$). MS (ESI): m/z 453 (MH$^+$).

Example 19

2-(1,3-dihydroxyprop-2-ylamino)-8-isopropyl-4-[4-(pyridin-2-yl)benzylamino]pyrazolo[1,5-a]-1,3,5-triazine (17)

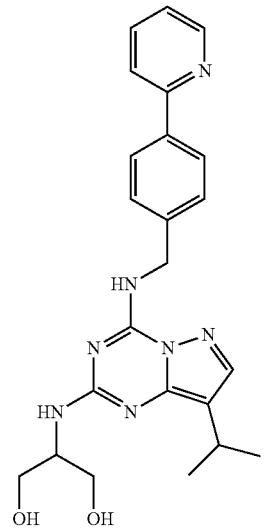 [SMILES: CC(C)c1cnn2c(NCc3ccc(-c4ccccn4)cc3)nc(NC(CO)CO)nc12]

According to the same conditions resulting in the preparation of the compound 2, the compound 17 is prepared from IIa.2 by oxidation reaction of the sulfur atom and then introduction of serinol. Yield=30%. Oil. $^1$H NMR (300 MHz, CDCl$_2$): δ 8.68 (d, 1H, J=4.4 Hz, H$_{arom}$), 7.96 (d, 2H, J=8.3 Hz, H$_{arom}$), 7.79-7.69 (m, 2H, H$_{arom}$) 7.64 (s, 1H, H$_{arom}$) 7.45 (d, 2H, J=8.3 Hz, H$_{arom}$) 7.26-7.21 (m, 1H, H$_{arom}$), 6.80 (bs, 1H, NH), 5.71 (bs, 1H, NH), 4.77 (d, 2H, J=5.9 Hz, CH$_2$), 4.08-4.95 (m, 1H, CH), 3.92-3.80 (m, 4H, 2 CH$_2$), 3.02 (hept, 1H, J=7.0 Hz, CH), 1.28 (d, 6H, J=7.0 Hz, 2 CH$_3$). MS (ESI): m/z 434 (MH$^+$).

Example 20

2-(1,3-dihydroxyprop-2-ylamino)-8-isopropyl-4-[4-(pyridin-2-yl)benzylamino]pyrazolo[1,5-a]-1,3,5-triazine fumarate (18)

The product 17 is treated with fumaric acid in an EtOH/Et$_2$O solution. The fumaric acid salt 18 crystallizes from the reaction medium. Mp=179-181° C. $^1$H NMR (300 MHz, DMSO-d$_6$): δ 13.11 (bs, 2H, OH), 8.76 (bs, 1H, NH), 8.64 (d, 1H, J=4.5 Hz, H$_{arom}$), 8.03 (d, 2H, J=8.1 Hz, H$_{arom}$), 7.94-7.82 (m, 2H, H$_{arom}$), 7.72 (s, 1H, H$_{arom}$) 7.49 (bs, 2H, H$_{arom}$) 7.35-7.31 (m, 1H, H$_{arom}$), 6.63 (s, 2H, 2 =CH), 6.33 (d, 1H, J=6.0 Hz, NH), 4.67 (d, 2H, J=6.0 Hz, CH$_2$), 3.98-3.83 (m, 1H, CH), 3.58-3.42 (m, 4H, 2 CH$_2$), 2.91 (hept, 1H, J=7.0 Hz, CH), 1.23 (d, 6H, J=7.0 Hz, 2 CH$_3$).

Example 21

2-(1,3-dihydroxyprop-2-ylamino)-8-isopropyl-4-[4-(pyridin-3-yl)benzylamino]pyrazolo[1,5-a]-1,3,5-triazine (19)

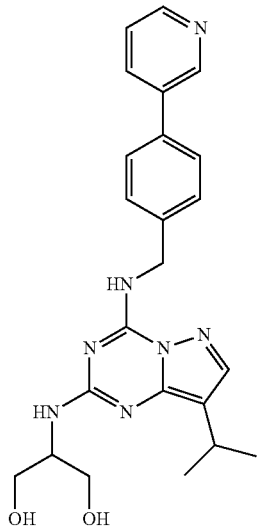 [SMILES: CC(C)c1cnn2c(NCc3ccc(-c4cccnc4)cc3)nc(NC(CO)CO)nc12]

a. 8-isopropyl-2-(methylsulfoxyl)-4-[4-(pyridin-3-yl)benzylamino]pyrazolo[1,5-a]-1,3,5-triazine (IVa)

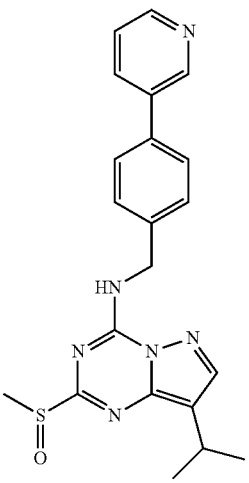

IVa

This compound is oxidized with meta-chloroperbenzoic acid according to the following protocol. A solution of IIa.4 (5.22 g, 13.3 mmol) dissolved in 277 ml of dichloromethane is cooled to 0° C. and then 3.46 g of 80% meta-chloroperbenzoic acid are added thereto. After stirring for 1 h, the mixture is washed with a sodium carbonate solution. The product crystallizes by concentration. The precipitate (IVa) is washed with a small amount of ether. Yield=84%. $^1$H NMR (400 MHz, DMSO-d$_6$): δ 8.85 (d, 1H, H$_{arom}$) 8.60 (d, 1H, H$_{arom}$), 7.95 (s, 1H, H$_{arom}$), 7.85 (d, 1H, H$_{arom}$), 7.60 (d, 2H, H$_{arom}$) 7.50 (d, 2H, H$_{arom}$) 7.40 (m, 1H, H$_{arom}$), 7.10 (m, 1H, H$_{arom}$), 4.98 (d, 2H, CH$_2$), 3.32 (hept, 1H, CH); 2.95 (s, 3H, CH$_3$), 1.35 (d, 6H, 2 CH$_3$).

b. Obtaining 2-(1,3-dihydroxyprop-2-ylamino)-8-isopropyl-4-[4-(pyridin-3-yl)benzylamino]pyrazolo[1,5-a]-1,3,5-triazine (19)

0.2 g of the sulfoxide. (IVa) is heated at 140° C. for 4 h in the presence of serinol (2-aminopropan-1,3-diol) in an amount of 0.36 g (3.9 mmol) for 12 h at 140° C. so as to form the product 19, which is isolated by crystallization from a mixture of ethyl acetate and ethyl ether. Yield=75%. $^1$H NMR (400 MHz, CDCl$_3$): δ 8.70 (d, 1H, H$_{arom}$) 8.55 (d, 1H, H$_{arom}$), 7.82 (d, 1H, H$_{arom}$), 7.68 (s, 1H, H$_{arom}$), 7.35 (m, 3H, H$_{arom}$), 7.58 (t, 1H, NH), 7.10 (d, 2H, H$_{arom}$), 5.80 (d, 1H, NH), 4.35 (d, 2H, CH$_2$), 3.85 (m, 1H); 3.75 (m, 1H), 2.98 (hept, 1H, CH); 1.28 (d, 6H, 2CH$_3$). MS (ESI): m/z 434 (MH$^+$).

Example 22

(S)-2-(1-hydroxybut-2-ylamino)-8-isopropyl-4-[4-(pyridin-3-yl)benzylamino]pyrazolo[1,5-a]-1,3,5-triazine (20)

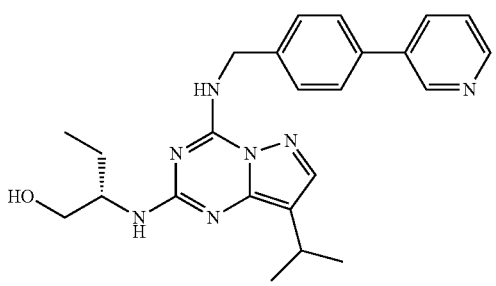 [SMILES: CC[C@@H](CO)Nc1nc(NCc2ccc(-c3cccnc3)cc2)n2ncc(C(C)C)c2n1]

The product 20 is prepared under the same conditions as 19 by heating 0.2 g of sulfoxide IVa with 0.368 ml of commercial (S)-(+)-2-aminobutanol. Yield=91%. $^1$H NMR (400 MHz, CDCl$_3$): δ 8.85 (d, 1H, H$_{arom}$), 8.60 (d, 1H, H$_{arom}$), 7.85 (dd, 1H, H$_{arom}$), 7.65 (s, 1H, H$_{arom}$ H), 7.55 (d, 2H, H$_{arom}$), 7.45 (d, 2H, H$_{arom}$), 7.40 (M, 1H, H$_{arom}$), 6.75 (t, 1H, NH), 5.00 (d, 1H, NH), 4.75 (d, 2H, CH$_2$), 3.95 (m, 1H), 3.85 (m, 1H), 3.65 (m, 1H), 3.04 (hept, 1H, CH), 1.65 (2H, CH$_2$), 1.25 (d, 6H, 2 CH$_3$), 1.03 (t, 3H, CH$_3$). MS (ESI): m/z 432 (MH$^+$).

Example 23

(2S,3S)-2-(1,3-dihydroxybut-2-ylamino)-8-isopropyl-4-[4-phenyl(pyridin-3-yl)methylamino]pyrazolo[1,5-a]-1,3,5-triazine (21)

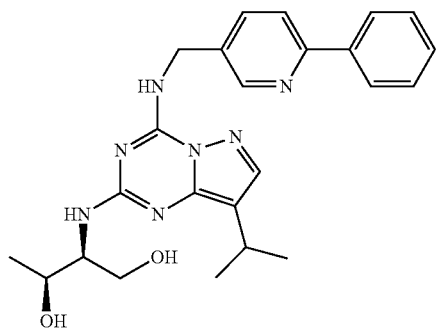 [SMILES: CC(C)c1cnn2c(NCc3ccc(-c4ccccc4)nc3)nc(N[C@@H](CO)[C@H](C)O)nc12]

a) 2-(methylsulfoxyl)-8-isopropyl-4-[4-phenyl(pyridin-3-yl)methylamino]pyrazolo[1,5-a]-1,3,5-triazine (IVb)

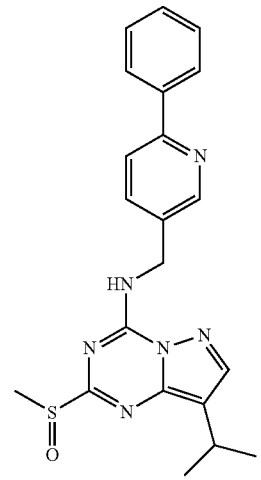

The oxidation is carried out as for the preparation of IVa by stirring, at 0° C., 4.76 g of IIa.5 in 259.8 ml of CH$_2$Cl$_2$ with 2 g of meta-chloroperbenzoic acid. The sulfoxide IVb is obtained with a yield of 87%. $^1$H NMR (400 MHz, CDCl$_3$): δ 8.78 (s, 1H, H$_{arom}$), 8.00 (d, 2H, H$_{arom}$), 7.95 (s, 1H, H$_{arom}$), 7.85 (d, 1H, H$_{arom}$), 7.75 (d, 1H, H$_{arom}$), 7.45 (m, 3H, H$_{arom}$), 4.95 (d, 2H, CH$_2$), 3.42 (hept, 1H, CH), 2.95 (s, 3H, CH$_3$), 1.3 (d, 6H, 2 CH$_3$).

b) Preparation of (2S,3S)-2-(1,3-dihydroxybut-2-ylamino)-8-isopropyl-4-[4-phenyl(pyridin-3-yl)methylamino]pyrazolo[1,5-a]-1,3,5-triazine (21)

The product 21 is prepared like the product 20 by heating, at 140°, 0.2 g of IVb with 0.413 g of (2S,3S)-threoninol. After cooling, the product 21 is extracted with ethyl acetate and purified on a silica column with 100% ethyl acetate as eluent. Yield=82%. $^1$H NMR (400 MHz, CDCl$_3$): δ 8.72 (s, 1H, H$_{arom}$), 7.95 (d, 2H, H$_{arom}$), 7.70 (m, 2H), 7.62 (s, 1H, H$_{arom}$), 7.45 (m, 3H, H$_{arom}$), 6.85 (bs, 1H, NH), 6.56 (d, 1H), 4.72 (d, 2H, CH$_2$), 4.20 (m, 1H, CH), 3.80 (m, 3H, CH$_2$OH), 2.99 (hept, 1H, CH), 1.30 (m, 9H, 3 CH$_3$). MS (ESI): m/z 448 (MH$^+$).

Example 24

(S)-2-(1-hydroxybut-2-ylamino)-8-isopropyl-4-[4-phenyl(pyridin-3-yl)methylamino]pyrazolo[1,5-a]-1,3,5-triazine (22)

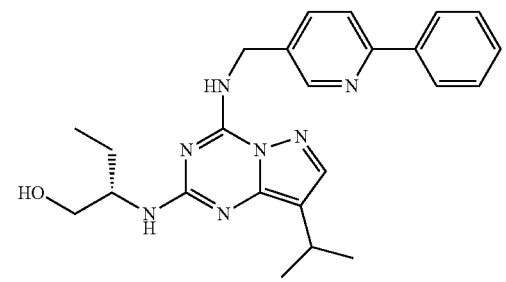 [SMILES: CC[C@@H](CO)Nc1nc(NCc2ccc(-c3ccccc3)nc2)n2ncc(C(C)C)c2n1]

This product is obtained by heating 0.3 g of sulfoxide IVb with 0.553 ml of commercial (S)-(+)-2-aminobutanol at 140° C. for 4 h. After 4 h, the product is isolated by extraction with ethyl acetate and purified on a silica column (eluent: EtOAc/CH$_2$Cl$_2$ 1:1). Yield=80%. $^1$H NMR (400 MHz, CDCl$_3$): δ 8.70 (d, 1H, H$_{arom}$), 8.00 (d, 2H, H$_{arom}$), 7.70 (m, 2H, H$_{arom}$), 7.62 (s, 1H, H$_{arom}$), 7.50 (m, 3H, H$_{arom}$), 6.90 (br, s, 1H), 5.05 (d, 1H, NH), 4.75 (d, 2H, CH$_2$), 3.90 (m, 1H, CH), 3.80 (m, 1H, CH$_2$), 3.60 (m, 1H, CH$_2$OH), 3.00 (hept, CH), 1.60 (m, 2H, CH$_2$), 1.25 (d, 6H, 2 CH$_3$), 1.00 (t, 3H, CH$_3$). MS (ESI): m/z 432 (MH$^+$).

Example 25

(2R,3R)-2-(1,3-dihydroxybut-2-ylamino)-8-isopropyl-4-[4-phenyl(pyridin-3-yl)methylamino]pyrazolo[1,5-a]-1,3,5-triazine (23)

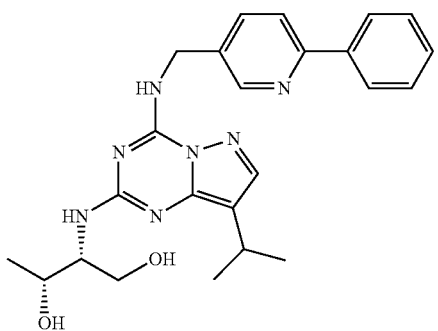 [SMILES: CC(C)c1cnn2c(NCc3ccc(-c4ccccc4)nc3)nc(N[C@H](CO)[C@@H](C)O)nc12]

This compound is obtained from the sulfoxide IVb using (2R,3R)-threoninol according to a protocol identical to that used in the previous examples. The product 23 is purified by silica column chromatography (eluent: EtOAc/CH$_2$Cl$_2$ 8:2). Yield=91%. $^1$H NMR (400 MHz, CDCl$_3$): δ 8.72 (5, 1H, H$_{arom}$), 7.95 (d, 2H, H$_{arom}$), 7.62 (s, 1H, H$_{arom}$), 7.70 (m, 2H, H$_{arom}$), 7.45 (m, 3H, H$_{arom}$) 6.85 (broad s, 1H, NH), 6.56 (d, 1H), 4.72 (d, 2H, CH$_2$), 4.20 (m, 1H, CH), 3.80 (m, 3H, CH$_2$) 2.99 (hept, 1H, CH), 1.30 (m, 9H, 3 CH$_3$). MS (ESI) m/z 448 (MH$^+$)

Example 26

2-(1,3-dihydroxyprop-2-ylamino)-8-isopropyl-4-[4-phenyl(pyridin-3-yl)methylamino]pyrazolo[1,5-a]-1,3,5-triazine (24)

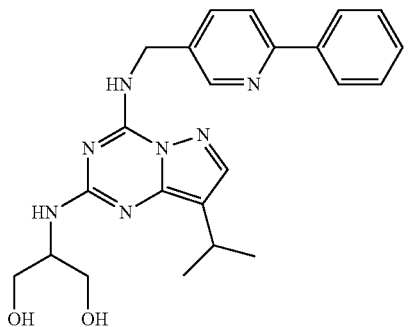 [SMILES: CC(C)c1cnn2c(NCc3ccc(-c4ccccc4)nc3)nc(NC(CO)CO)nc12]

This product is prepared by heating the sulfoxide IVb with serinol according to the conditions described in example 23. The product is purified on a silica column (eluent: EtOAc). Yield=78%. $^1$H NMR (400 MHz, CDCl$_3$): δ 8.71 (s, 1H, H$_{arom}$), 7.95 (d, 2H, H$_{arom}$) 7.73 (m, 2H, H$_{arom}$), 7.64 (s, 1H, H$_{arom}$) 7.47 (m, 3H, H$_{arom}$) 6.98 (bs, 1H), 5.71 (d, 1H, NH), 4.75 (d, 2H, CH$_2$), 4.06 (m, 1H, CH), 3.84 (m, 4H, CH$_2$), 2.99 (hept, 1H), 1.26 (d, 6H, 2 CH$_3$).

Example 27

(R)-2-[[8-isopropyl-4-[[4-(2-pyridyl)phenyl]methylamino]pyrazolo[1,5-a][1,3,5]triazin-2-yl]amino]-4-methylpentan-1-ol or (R)-2-(1-hydroxy-4-methylpent-2-ylamino)-8-isopropyl-4-[4-phenyl(pyridin-3-yl)methylamino]pyrazolo[1,5-a]-1,3,5-triazine (25)

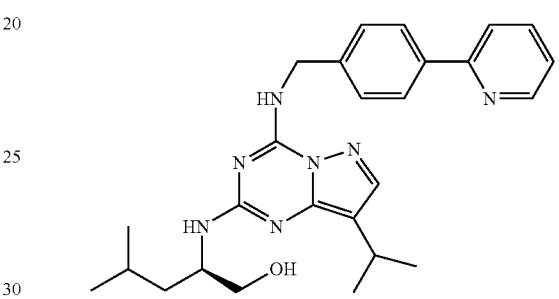

This product is prepared by heating the sulfoxide IVa (0.2 g) with D-valinol (0.406 g) according to the conditions described in example 23. The product is purified on a silica column (eluent: EtOAc/cyclohexane 1:1). Yield=76%. $^1$H NMR (400 MHz, CDCl$_3$): δ 8.71 (s, 1H, H$_{arom}$), 7.99 (d, 2H, H$_{arom}$), 7.75 (m, 2H, H$_{arom}$), 7.63 (s, 1H, H$_{arom}$), 7.47 (d, 2H, H$_{arom}$), 6.72 (bs, 1H), 4.95 (d, 1H, NH), 4.75 (m, 2H, CH$_2$), 4.10 (m, 1H), 3.80 (m, 1H), 3.60 (m, 2H), 3.03 (hept, 1H, CH), 1.40-1.80 (m, 3H) 1.30 (d 6H, 2 CH$_3$), 0.93 (m, 6H, 2CH$_3$).

Example 28

(S)-2-[[8-isopropyl-4-[[4-(2-pyridyl)phenyl]methylamino]pyrazolo[1,5-a][1,3,5]triazin-2-yl]amino]-4-methylpentan-1-ol or (S)-2-(1-hydroxy-4-methylpent-2-ylamino)-8-isopropyl-4-[4-phenyl(pyridin-3-yl)methylamino]pyrazolo[1,5-a]-1,3,5-triazine (26)

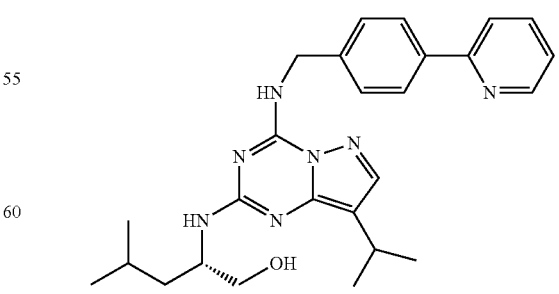

This product is prepared by heating the sulfoxide IVa (0.2 g) with L-valinol (0.406 g) according to the conditions described in example 23. The product is purified on a silica column (eluent: EtOAc/cyclohexane 1:1). Yield=76%. ¹H NMR (400 MHz, CDCl₃): δ 8.71 (d, 1H, H$_{arom}$), 7.99 (d, 2H, H$_{arom}$), 7.75 (m, 2H, H$_{arom}$), 7.63 (s, 1H, H$_{arom}$), 7.47 (d, 2H, H$_{arom}$), 6.72 (bs, 1H), 4.95 (d, 1H, NH), 4.75 (m, 2H, CH₂), 4.10 (m, 1H), 3.80 (m, 1H), 3.60 (m, 2H), 3.03 (hept, 1H, CH), 1.40-1.80 (m, 3H) 1.31 (d 6H, 2 CH₃), 0.93 (m, 6H, 2CH₃).

Example 29

(S)-2-(1-hydroxy-3,3-dimethylbut-2-ylamino)-8-isopropyl-4-[4-(pyridin-2-yl)benzylamino]pyrazolo[1,5-a]-1,3,5-triazine (27)

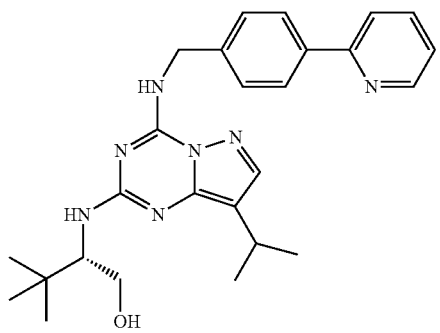 [SMILES: CC(C)c1cnn2c(NCc3ccc(-c4ccccn4)cc3)nc(N[C@H](CO)C(C)(C)C)nc12]

a) 2-(methylsulfoxyl)-8-isopropyl-4-[4-(pyridin-2-yl)benzylamino]pyrazolo[1,5-a]-1,3,5-triazine (IVc)

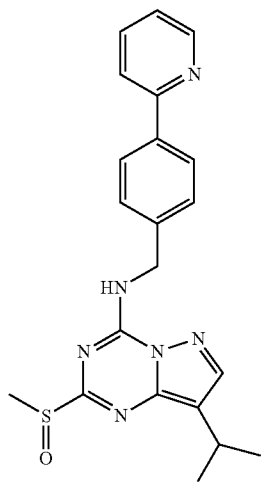

IVc

The oxidation is carried out as for the preparation of IVb by stirring, at 0° C., 4.76 g of IIa2 in 259.8 ml of CH₂Cl₂ with 2 g of meta-chloroperbenzoic acid. Yield=90%. ¹H NMR (400 MHz, CDCl₃): δ 8.70 (d, 1H, H$_{arom}$), 8.05 (d, 2H, H$_{arom}$), 7.95 (s, 1H, H$_{arom}$), 7.75 (m, 2H, H$_{arom}$), 7.50 (d, 2H, H$_{arom}$), 7.22 (m, 1H, H$_{arom}$), 7.10 (t, 1H, NH), 4.92 (d, 2H, CH₂), 3.32 (hept, 1H, CH), 2.92 (s, 3H, CH₃), 1.3 (d, 6H, 2 CH₃).

b) 2-(1-hydroxy-3,3-dimethylbut-2-ylamino)-8-isopropyl-4-[4-(pyridin-2-yl)benzylamino]pyrazolo[1,5-a]-1,3,5-triazine (27)

The derivative 27 is prepared by heating the product IVc 0.2 g with the 0.512 g of (S)-tert-leucinol after 4 h of heating at 140° C. After extraction with EtOAc and washing with water, the product formed crystallizes by concentration of the solvent. ¹H NMR (400 MHz, CDCl₃): δ 8.00 (d, 2H, H$_{arom}$), 7.75 (m, 2H, H$_{arom}$), 7.62 (s, 1H, H$_{arom}$), 7.45 (d, 2H, H$_{arom}$), 7.25 (1H, H$_{arom}$), 6.75 (s, 1H), 5.10 (m, 1H), 4.70 (m, 2H), 4.04 (m, 1H), 3.92 (m, 1H), 3.62 (m, 1H), 3.03 (hept, CH), 1.30 (d, 6H, 2 CH₃), 1.00 (s, 9H, 3 CH₃).

Example 30

(S)-2-(1-hydroxy-3-methylbut-2-ylamino)-8-isopropyl-4-[4-(pyridin-2-yl)benzylamino]pyrazolo[1,5-a]-1,3,5-triazine (28)

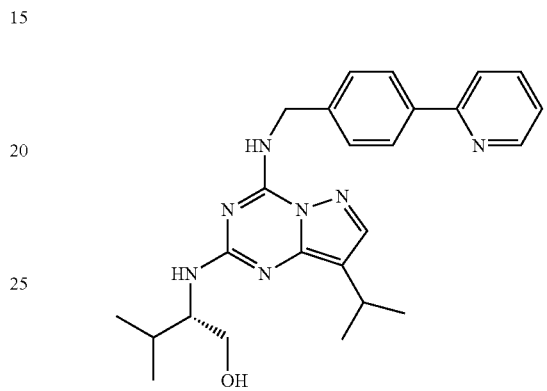

The derivative 28 is prepared as in example 29 by heating the product IVc with (S)-(L)-valinol. Yield=72%. ¹H NMR (400 MHz, CDCl₃): δ 8.70 (d, 1H, H$_{arom}$), 7.98 (d, 2H, H$_{arom}$) 7.75 (m, 2H, H$_{arom}$), 7.62 (s, 1H, H$_{arom}$) 7.45 (d, 2H, H$_{arom}$), 7.25 (m, 1H, H$_{arom}$), 6.80 (s, 1H, NH), 5.10 (d, 1H, NH), 4.80 (d, 2H, CH₂), 3.80 (m, 2H, CH₂), 3.0X (CH, 1H), 1.80 (m, 1H, CH), 1.25 (d, 6H, 2 CH₃), 1.0X (d, 6H, 2 CH₃).

Example 31

2-[4-[1-[8-isopropyl-4-[[4-(pyridin-2-yl)phenyl]methylamino]pyrazolo[1,5-a]-1,3,5-triazin-2-yl]piperidin-4-yl]piperidin-1-yl]ethanol (29)

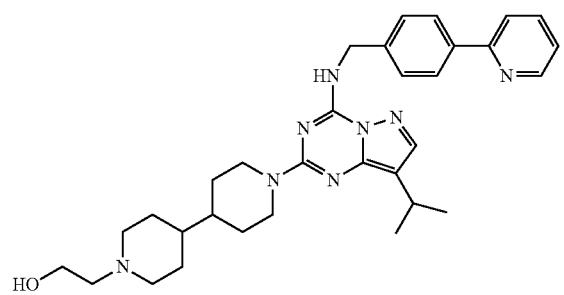 [SMILES: CC(C)c1cnn2c(NCc3ccc(-c4ccccn4)cc3)nc(N3CCC(C4CCN(CCO)CC4)CC3)nc12]

The derivative 29 is prepared as in example 29 by heating the product IVc with the bispiperidine-ethanol described by P. Leon, C. Garbay-Jaureguiberry, B. Lambert, J. B. Le Pecq, B. P. Rogues. Asymmetrical bisintercalators as potential antitumor agents *J. Med. Chem.*, 1988, 31 (5), pp 1021-1026.

Yield=78%. ¹H NMR (400 MHz, CDCl₃): δ 8.68 (d, 1H, H$_{arom}$), 7.98 (d, 2H, H$_{arom}$), 7.75 (m, 2H, H$_{arom}$), 7.60 (s, 1H, H$_{arom}$), 7.48 (d, 2H, H$_{arom}$), 7.22 (m, 1H, H$_{arom}$), 6.64 (t, 1H, NH), 4.85 (s, 1H), 4.8 (s, 1H), 4.70 (d, 2H, CH₂), 3.80 (m, 2H, CH$_2$), 3.60 (m, 2H, CH$_2$), 3.00 (d, 2H, CH$_2$), 2.74 (t, 2H, CH$_2$), 2.55 (m, 1H), 2 (t, 2H, CH$_2$), 1.70 (m, 4H, CH$_2$), 1.40 (m, 2H, CH$_2$), 1.30 (d, 6H, 2 CH$_3$), 1.15 (m, 2H).

Example 32

2-[4-[8-isopropyl-4-[[4-(Pyridin-2-yl)phenyl]methylamino]pyrazolo[1,5-a]-1,3,5-triazin-2-yl]piperidin-1-yl]ethanol (30)

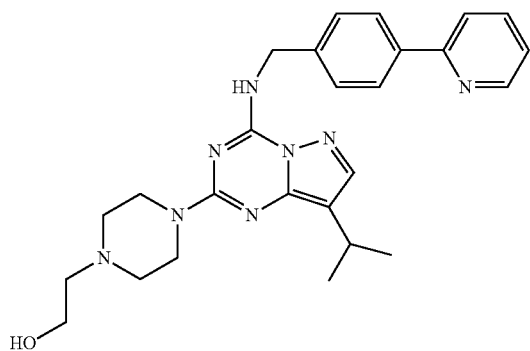 [SMILES: CC(C)c1cnn2c(NCc3ccc(-c4ccccn4)cc3)nc(N3CCN(CCO)CC3)nc12]

The product 30 is prepared as in example 29 by heating the product IVc with 2-piperazinylethanol. Yield=65%. $^1$H NMR (400 MHz, CDCl$_3$): δ 8.70 (d, 1H, H$_{arom}$), 7.98 (d, 2H, H$_{arom}$) 7.72 (m, 2H, H$_{arom}$) 7.65 (s, 1H, H$_{arom}$), 7.48 (d, 2H, H$_{arom}$), 7.25 (m, 1H, H$_{arom}$), 6.70 (t, 1H, NH), 4.78 (d, 2H, CH$_2$), 3.83 (m, 4H, CH$_2$), 3.65 (m, 2H, CH$_2$), 3.05 (hept, 1H, CH), 2.52 (m, 2H, CH$_2$), 2.48 (m, 4H, CH$_2$), 1.30 (d, 6H, 2 CH$_3$).

Example 33

(R)-2-(1,2-dihydroxypropan-3-ylamino)-8-ethyl-4-[4-(pyridin-2-yl)benzylamino]pyrazolo[1,5-a]-1,3,5-triazine (31)

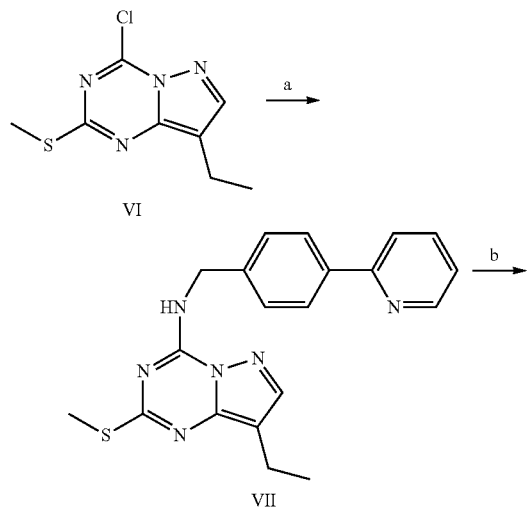

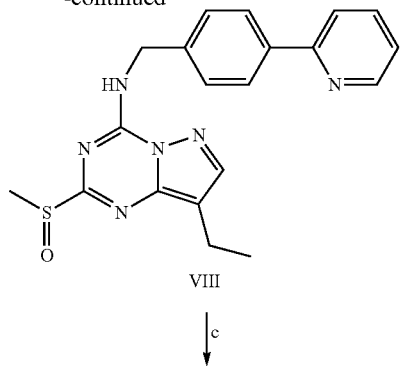

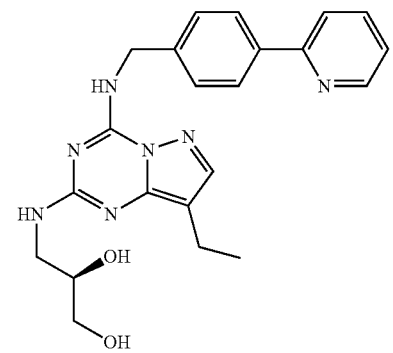

The product 31 is prepared from the intermediate VI obtained as described by Z Nie, C Perretta, Ph Erickson, S Margosiak, Ji Lu, A Averill, Rt Almassy, Shaosong hu. Structure-based design and synthesis of novel macrocyclic pyrazolo[1,5-a][1,3,5]triazine compounds as potent inhibitors of protein kinase CK2 and their anticancer activities *Bioorganic & Medicinal Chemistry Letters*, Volume 18, Issue 2, 15 Jan. 2008, Pages 619-623.

The intermediate VIII is characterized by NMR. $^1$H NMR (400 MHz, CDCl$_3$): δ 8.70 (d, 1H, H$_{arom}$), 8.00 (d, 2H, H$_{arom}$), 7.75 (m, 2H, H$_{arom}$), 7.50 (d, 2H, H$_{arom}$) 7.26 (s, 1H, H$_{arom}$) 6.80 (t, 1H, NH), 4.85 (d, 2H, CH$_2$), 2.68 (q, 2H, CH$_2$), 2.55 (s, 3H, CH$_3$), 1.25 (t, 3H, CH$_3$).

The product 31 is prepared by heating the intermediate VIII, at 140° C., under the conditions of example 23, with commercial (R)-3-amino-1,2-propanediol. Yield=76%. $^1$H NMR (400 MHz, CDCl$_3$): δ 8.70 (d, 1H, H$_{arom}$), 8.00 (d, 2H, H$_{arom}$) 7.75 (m, 2H, H$_{arom}$), 7.66 (5, 1H, H$_{arom}$) 7.48 (d, 2H, H$_{arom}$), 7.82 (bs, 1H, NH), 7.25 (m, 1H), 5.32 (bs, 1H), 4.75 (d, 2H, CH$_2$), 3.80 (m, 1H, CH), 3.60 (m, 4H, 2 CH$_2$), 2.55 (q, 2H, CH$_2$), 1.21 (t, 3H, CH$_3$).

Example 34

Preparation of the Ester 33 from the Product 31

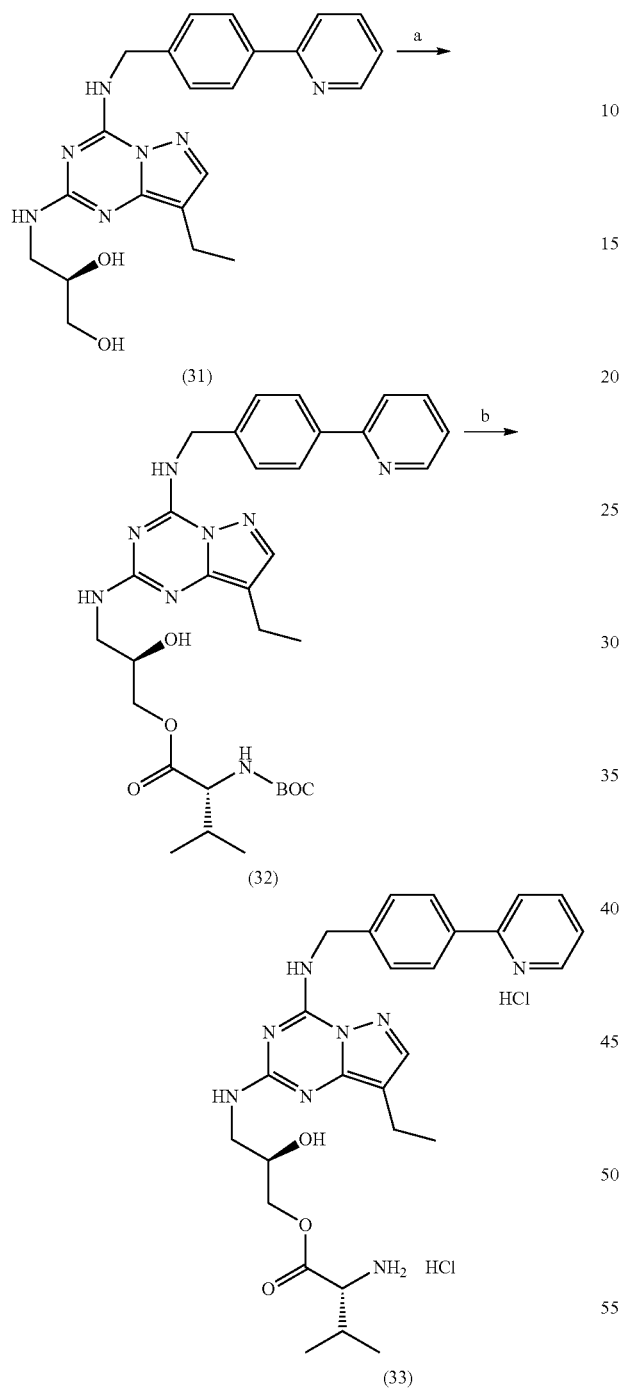

a) Esterification by Boc-D-Valine

A solution of 0.7 g of Boc-D-Valine and of 0.49 g of hydroxybenzotriazole (HOBt) in 10 ml of EtOAc is cooled with stirring to 0° C. 0.763 g of dicyclohexylcarbodiimide (DCC) is added to this solution. The mixture is then stirred for 2 h at ambient temperature and then filtered. The precipitate (dicyclohexylurea) is rinsed with 3 ml of EtOAc. The filtrate is immediately added to a solution of 0.73 g of 31 and of triethylamine (1.5 ml) in tetrahydrofuran (THF, 15 ml). The mixture is stirred for 24 h at ambient temperature and then concentrated under vacuum, and taken up with EtOAc. The organic phase is washed with a citric acid solution and then with a sodium carbonate solution and with water. The organic phase is dried and then evaporated under vacuum. The residue contains the virtually pure ester, which can be purified on a silica column (eluent: EtOAc/cyclohexane/THF/Et$_3$N 45:50:4:1). The ester 32 is obtained with a yield of 75%. In this esterification reaction, although the secondary alcohols can also be esterified under similar conditions, the exclusive formation of the ester of the primary alcohol is unexpectedly observed.

b) Obtaining the Salt 33

A solution of anhydrous hydrochloric acid (2 μM) in ethyl ether is added to the ester 32 in solution in ethyl ether. After 30 min at ambient temperature, the precipitate (33) is filtered off, washed with ether and dried under vacuum. Yield=90%. $^1$H NMR (400 MHz, DMSO-d$_6$): δ 10.05 (t, 1H), 8.60 (d, 1H), 8.55 (bs, 1H), 8.20 (m, 2H, H$_{arom}$), 8.05 (d, 1H, H$_{arom}$), 7.85 (m, 2H, H$_{arom}$), 7.60 (t, 1H, H$_{arom}$), 7.40 (m, 3H, H$_{arom}$), 4.50 (d, 2H), 3.95 (m, 1H), 3.80 (m, 1H), 3.70 (m, 1H), 3.40 (m, 1H), 2.00 (m, 2H), 0.90 (t, 3H, CH$_3$), 0.65 and 0.70 (2 d, 6H, 2 CH$_3$).

Example 35

(S)-2-(1,2-dihydroxypropan-3-ylamino)-8-ethyl-4-[4-(pyridin-2-yl)benzylamino]pyrazolo[1,5-a]-1,3,5-triazine (34)

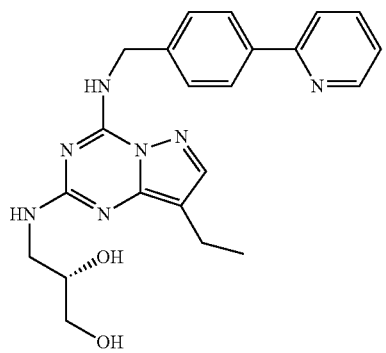 [SMILES: CCc1cnn2c(NCc3ccc(-c4ccccn4)cc3)nc(NC[C@H](O)CO)nc12]

This product is prepared like its enantiomer 31 (example 34). In the tests on the four kinases assayed, the derivative 34 is shown to be more active than the derivative 31.

Example 36

(S)-8-ethyl-2-(1-hydroxybut-2-ylamino)-4-[4-(pyridin-2-yl)benzylamino]pyrazolo[1,5-a]-1,3,5-triazine (35)

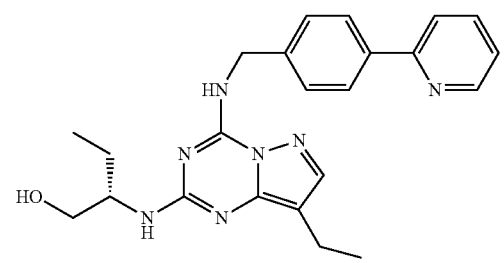 [SMILES: CCc1cnn2c(NCc3ccc(-c4ccccn4)cc3)nc(N[C@@H](CC)CO)nc12]

The product 31 is prepared by heating the intermediate VIII at 140° C., under the conditions of example 23, with commercial (S)-(+)-2-aminobutanol.

¹H NMR (400 MHz, CDCl₃): δ 8.70 (d, 1H); 8.00 (d, 2H); 7.75 (m, 2H); 7.64 (s, 1H); 7.48 (m, 2H); 7.25 (m, 1H); 4.80 (m, 2H); 3.95 (m, 1H); 3.80 (m, 1H); 3.63 (m, 1H); 1.60 (m, 1H); 1.22 (m, 5H).

Example 37

(R)-8-ethyl-2-(1-hydroxybut-2-ylamino)-4-[4-(pyridin-2-yl)benzylamino]pyrazolo[1,5-a]-1,3,5-triazine (36)

The product 36 is prepared by heating the intermediate VIII at 140° C., under the conditions of example 23, with commercial (R)-(-)-2-aminobutanol.

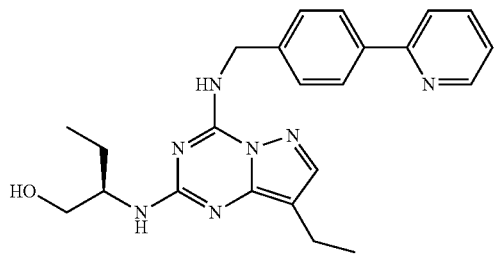 [SMILES: CCc1cnn2c(NCc3ccc(-c4ccccn4)cc3)nc(N[C@H](CC)CO)nc12]

¹H NMR (400 MHz, CDCl₃): δ 8.70 (d, 1H); 8.00 (d, 2H); 7.75 (m, 2H); 7.64 (s, 1H); 7.48 (m, 2H); 7.25 (m, 1H); 4.80 (m, 2H); 3.95 (m, 1H); 3.80 (m, 1H); 3.63 (m, 1H); 1.60 (m, 1H); 1.22 (m, 5H).

Example 38

2-(1,3-dihydroxyprop-2-ylamino)-8-ethyl-4-[4-(pyridin-2-yl)benzylamino]pyrazolo[1,5-a]-1,3,5-triazine (37)

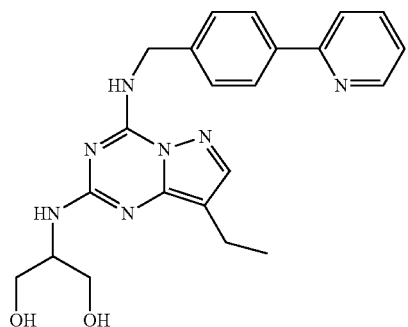 [SMILES: CCc1cnn2c(NCc3ccc(-c4ccccn4)cc3)nc(NC(CO)CO)nc12]

The product 37 is prepared by heating the intermediate VIII at 140° C., under the conditions of example 23, with serinol.

Example 39

2-[(2S)-1-[8-ethyl-4-[[4-(pyridin-2-yl)phenyl]methylamino]pyrazolo[1,5-a]-1,3,5-triazin-2-yl]piperidin-2-yl]ethanol (38)

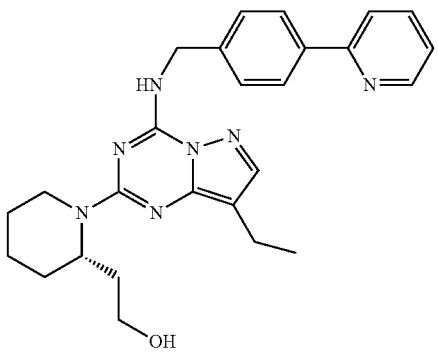 [SMILES: CCc1cnn2c(NCc3ccc(-c4ccccn4)cc3)nc(N3CCCC[C@H]3CCO)nc12]

The product 38 is prepared by heating the intermediate VIII at 140° C., under the conditions of example 23, with (S)-2-(piperidin-2-yl)ethanol. Yield=75%. ¹H NMR (400 MHz, CDCl₃): 8.64 (d, 1H, Haro), 7.92 (d, 2H, H$_{arom}$), 7.70 (m, 2H, H$_{arom}$), 7.54 (s, 1H, H$_{arom}$), 7.42 (d, 2H, H$_{arom}$), 4.95 (m, 1H), 4.79 (m, 1H), 4.75 (d, 2H), 3.55 (d, 1H), 3.28 (t, 1H), 2.74 (t, 1H), 2.47 (q, 2H), 2.03 (t, 1H); 1.40-1.80 (m, piperidine), 1.14 (t, 3H, CH₃).

Example 40

2-[[8-ethyl-4-[[4-(2-pyridyl)phenyl]methylamino]pyrazolo[1,5-a][1,3,5]triazin-2-yl](2-hydroxyethyl)amino]ethanol (39)

The product 39 is prepared by heating the intermediate VIII at 140° C., under the conditions of example 23, with diethanolamine.

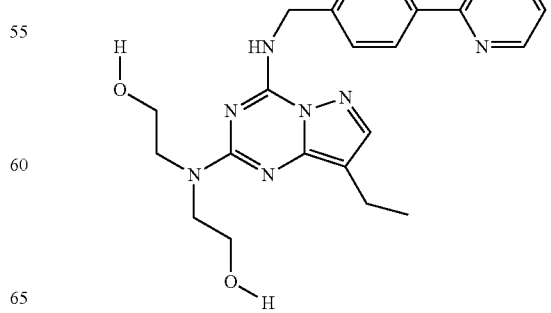

Yield=78%. $^1$H NMR (400 MHz, CDCl$_3$): δ 8.68 (d, 1H, H$_{arom}$) 7.96 (d, 2H, H$_{arom}$), 7.74 (m, 2H, H$_{arom}$) 7.65 (s, 1H, 7-H), 7.43 (d, 2H, H$_{arom}$), 7.26 (m, 1H, H$_{arom}$), 6.97 (t, 1H, NH), 4.74 (d, 2H, CH$_2$N), 3.77 (m, 4H, 2 CH$_2$OH), 2.56 (q, 2H, CH$_2$CH$_3$), 1.22 (t, 3H, CH$_3$).

Example 41

(2B,3B)-2-[[8-ethyl-4-[[4-(2-pyridyl)phenyl]methylamino]pyrazolo[1,5-a][1,3,5]triazin-2-yl]amino]butane-1,3-diol (40)

The product 40 is prepared by heating the intermediate VIII at 140° C., under the conditions of example 23, with L-threoninol (2R,3R-threoninol).

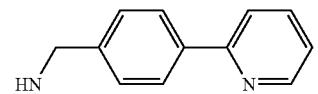

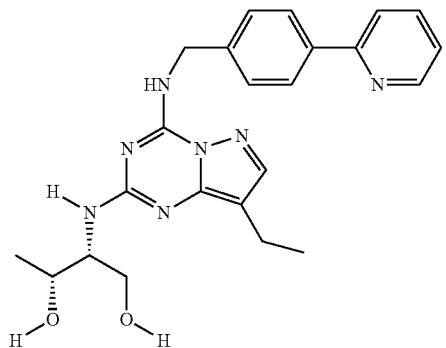 [SMILES: CCc1cnn2c(NCc3ccc(-c4ccccn4)cc3)nc(N[C@H](CO)[C@@H](C)O)nc12]

Yield=78%. $^1$H NMR (400 MHz, CDCl$_3$): δ 8.68 (d, 1H, H$_{arom}$), 7.96 (d, 2H, H$_{arom}$), 7.74 (m, 2H, H$_{arom}$), 7.65 (s, 1H, 7-H), 7.43 (d, 2H, H$_{arom}$), 7.26 (m, 1H, H$_{arom}$), 6.97 (t, 1H, NH), 4.74 (d, 2H, CH$_2$N), 3.77 (m, 4H, 2 CH$_2$OH), 2.56 (q, 2H, CH$_2$CH$_3$), 1.22 (t, 3H, CH$_3$).

Example 42

(2S,3S)-2-[[8-ethyl-4-[[4-(2-pyridyl)phenyl]methylamino]pyrazolo[1,5-a][1,3,5]triazin-2-yl]amino]butane-1,3-diol (41)

The product 41 is prepared by heating the intermediate VIII at 140° C., under the conditions of example 23, with D-threoninol (2S,3S-threoninol).

Yield=75%. $^1$H NMR (400 MHz, CDCl$_3$): δ 8.68 (d, 1H, H$_{arom}$), 7.97 (d, 2H, H$_{arom}$), 7.75 (m, 2H, H$_{arom}$), 7.63 (s, 1H, 7-H), 7.45 (d, 2H, H$_{arom}$) 7.24 (m, 1H, H$_{arom}$), 6.75 (t, 1H, NH), 4.77 (d, 2H, CH$_2$N), 4.18 (m, 1H), 3.90 (m, 3H), 2.55 (q, 2H, CH$_2$CH$_3$), 1.30 (d, 3H, CHC$\underline{H}_3$); 1.42 (t, 3H, CH$_2$CH$_3$).

Table II hereinafter illustrates the chemical structures and the physical properties of some examples of compounds of formula (I) according to the invention. In this table:

Mp=melting point, in degrees Celsius (° C.),

"Yld" denotes the yield (%),

MH$^+$=mass spectrometry (m/z), isoPr is an isopropyl group,

Et is an ethyl group, in the "salt" column "-" represents a compound in free base form, whereas "fu" represents a compound in its fumarate form, (+) indicates that the compound is a dextrorotatory enantiomer, (–) a levorotatory enantiomer:

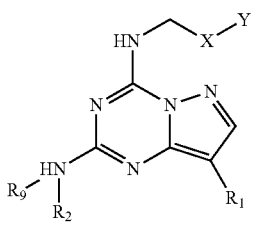

(I)

TABLE II

| Compound No. | R₁ | R₂ or NR₂R₉ | R₉ | X | Y | salt | Mp (°C.) and/or mass (m/z) |
|---|---|---|---|---|---|---|---|
| 1 | isoPr | H₃C, HO, (methyl-branched, CH₃) | H | p-phenylene | phenyl | — | MH⁺ = 431 |
| 2 | isoPr | H₃C, HO, (methyl-branched) | H | p-phenylene | 2-pyridyl | — | MH⁺ = 432 |
| 3 | isoPr | H₃C, HO, (methyl-branched, stereo) | H | p-phenylene | 2-pyridyl | fu | Mp = 175-177 |
| 4 | isoPr | H₃C, HO, (methyl-branched, stereo) | H | p-phenylene | 2-pyridyl | — | MH⁺ = 432 |
| 5 | isoPr | H₃C, HO, (methyl-branched, stereo) | H | p-phenylene | 2-pyridyl | fu | Mp = 175-177 |
| 6 | isoPr | H₃C, HO, (methyl-branched) | H | p-phenylene | 3-thienyl | — | MH⁺ = 437 |
| 7 | isoPr | H₃C, HO, (methyl-branched, stereo) | H | p-phenylene | 3-thienyl | — | MH⁺ = 437 |
| 8 | isoPr | OH, OH (diol) | H | p-phenylene | 2-pyridyl | — | MH⁺ = 434 |
| 9 | isoPr | OH, OH (diol, stereo) | H | p-phenylene | 2-pyridyl | fu | Mp = 168-170 |
| 10 | isoPr | OH, OH (diol) | H | p-phenylene | 2-pyridyl | — | MH⁺ = 434 |
| 11 | isoPr | OH, OH (diol, stereo) | H | p-phenylene | 2-pyridyl | fu | Mp = 168-170 |
| 12 | isoPr | HO, OH, CH₃ (triol/methyl) | H | p-phenylene | 2-pyridyl | — | MH⁺ = 448 |

TABLE II-continued

| Compound No. | R₁ | R₂ or NR₂R₉ | R₉ | X | Y | salt | Mp (° C.) and/or mass (m/z) |
|---|---|---|---|---|---|---|---|
| 13 | isoPr | HO—CH(CH₃)—CH(OH)— (stereo) | H | p-phenylene | 2-pyridyl | fu | Mp = 187-189 |
| 14 | isoPr | HO—CH(CH₃)—CH(OH)— (stereo) | H | p-phenylene | 2-pyridyl | — | MH⁺ = 448 |
| 15 | isoPr | HO—CH(CH₃)—CH(OH)— (stereo) | H | p-phenylene | 2-pyridyl | fu | Mp = 187-189 |
| 16 | isoPr | HO—CH(CH₃)—CH(OH)— (stereo) | H | p-phenylene | 3-thienyl | — | MH⁺ = 453 |
| 17 | isoPr | 2-methyl-1,3-propanediol | H | p-phenylene | 2-pyridyl | — | MH⁺ = 434 |
| 18 | isoPr | 2-methyl-1,3-propanediol | H | p-phenylene | 2-pyridyl | fu | Mp = 179-181 |
| 19 | isoPr | 2-methyl-1,3-propanediol | H | p-phenylene | 3-pyridyl | — | MH⁺ = 434 |
| 20 | isoPr | H₃C—CH₂—CH(CH₃)—CH₂OH | H | p-phenylene | 3-pyridyl | — | MH⁺ = 432 |
| 21 | isoPr | H₃C—CH(OH)—CH(CH₃)—CH₂OH | H | 2,5-pyridyl | phenyl | — | MH⁺ = 448 |
| 22 | isoPr | H₃C—CH₂—CH(CH₃)—CH₂OH | H | 2,5-pyridyl | phenyl | — | MH⁺ = 432 |
| 23 | isoPr | H₃C—CH(OH)—CH(CH₃)—CH₂OH (stereo) | H | 2,5-pyridyl | phenyl | — | MH⁺ = 448 |

TABLE II-continued

| Compound No. | R₁ | R₂ or NR₂R₉ | R₉ | X | Y | salt | Mp (° C.) and/or mass (m/z) |
|---|---|---|---|---|---|---|---|
| 24 | isoPr | (S)-2-methylpropane-1,3-diol (HO-CH₂-C*H(CH₃)-CH₂-OH) | H | 2,5-pyridyl | phenyl | — | MH⁺ = 448 |
| 25 | isoPr | (CH₃)₂CH-CH₂-CH(CH₃)-CH₂-OH | H | 2,5-pyridyl | phenyl | — | MH⁺ = 460 |
| 26 | isoPr | (CH₃)₂CH-CH₂-C*H(CH₃)-CH₂-OH | H | 2,5-pyridyl | phenyl | — | MH⁺ = 460 |
| 27 | isoPr | (CH₃)₃C-CH(CH₃)-CH₂-OH | H | 1,4-phenyl | 2-pyridyl | — | MH⁺ = 460 |
| 28 | isoPr | (CH₃)₂CH-CH(CH₃)-CH₂-OH | H | 1,4-phenyl | 2-pyridyl | — | MH⁺ = 446 |
| 29 | isoPr | 1'-(2-hydroxyethyl)-4,4'-bipiperidine | | 1,4-phenyl | 2-pyridyl | — | — |
| 30 | isoPr | 4-methyl-1-(2-hydroxyethyl)piperazine | | 1,4-phenyl | 2-pyridyl | — | — |
| 31 | Et | (R)-2-ethylpropane-1,3-diol | H | 1,4-phenyl | 2-pyridyl | — | MH⁺ = 420 |

TABLE II-continued

| Compound No. | R₁ | R₂ or NR₂R₉ | R₉ | X | Y | salt | Mp (° C.) and/or mass (m/z) |
|---|---|---|---|---|---|---|---|
| 32 | Et | *(2-hydroxybutyl ester of N-Boc-valine)* | H | *p-phenylene* | *2-pyridyl* | — | MH⁺ = 618 |
| 33 | Et | *(2-hydroxybutyl ester of valine, protonated amine)* | H | *p-phenylene* | *2-pyridyl* | H | — |
| 34 | Et | *(R)-butane-1,2-diol* | H | *p-phenylene* | *2-pyridyl* | — | MH⁺ = 420 |
| 35 | Et | *(S)-2-methylbutan-1-ol* | H | *p-phenylene* | *2-pyridyl* | — | MH⁺ = 418 |
| 36 | Et | *(R)-2-methylbutan-1-ol* | H | *p-phenylene* | *2-pyridyl* | — | MH⁺ = 418 |
| 37 | Et | *2-methylpropane-1,3-diol* | H | *p-phenylene* | *2-pyridyl* | — | MH⁺ = 420 |
| 38 | Et | *2-(1-methylpiperidin-2-yl)ethanol* | H | *p-phenylene* | *2-pyridyl* | — | MH⁺ = 458 |
| 39 | Et | *N-methyldiethanolamine* | H | *p-phenylene* | *2-pyridyl* | — | MH⁺ = 434 |
| 40 | Et | *(2R,3R)-3-methylbutane-1,2-diol* | H | *p-phenylene* | *2-pyridyl* | — | MH⁺ = 434 |

TABLE II-continued

| Compound No. | $R_1$ | $R_2$ or $NR_2R_9$ | $R_9$ | X | Y | salt | Mp (°C.) and/or mass (m/z) |
|---|---|---|---|---|---|---|---|
| 41 | Et | H₃C-CH(OH)-CH(OH)-CH₂OH (stereochem shown) | H | p-tolyl | 2-pyridyl | | MH⁺ = 434 |

The compounds according to the invention were the subject of pharmacological assays for determining their inhibitory effect on protein kinase activity.

According to a first series of pharmacological assays, the compounds were tested on seven protein kinases according to the methodology described hereinafter.

It is in particular noted that the inhibitory activity of the compounds according to the invention on CDK1, CDK2, CDK5 and CDK9 generally exhibits an $IC_{50}$ around 0.050 μm (CDK1: 0.015-0.070 μM; CDK2: 0.012-0.060 μM; CDK5: 0.018-0.064 μM; CDK9: 0.030-0.091 μM). On CK1, the compounds of the invention show an $IC_{50}$ of between 0.06 and 0.2 μM, whereas on DYRK1A and GSK-3, the $IC_{50}$ values are around 0.5-2.0 μM and >2.8 μM, respectively.

Table III collates the results on the $IC_{50}$ values reported in μM.

Materials and Methods

Buffers

Homogenization buffers: 60 mM β-glycerophosphate, 15 mM p-nitrophenyl phosphate, 25 mM Mops (pH 7.2), 15 mM EGTA, 15 mM MgCl₂, 1 mM DTT, 1 mM sodium vanadate, 1 mM NaF, 1 mM phenyl phosphate, 10 μg leupeptin/ml, 10 μg aprotinin/ml, 10 μg soybean trypsin inhibitor/ml and 100 μM benzamidine.

Buffer A: 10 mM MgCl₂, 1 mM EGTA, 1 mM DTT, 25 mM Tris-HCl pH 7.5, 50 μg heparin/ml.

Buffer C: 60 mM β-glycerophosphate, 15 mM p-nitrophenyl phosphate, 25 mM Mops (pH 7.2), 5 mM EGTA, 15 mM MgCl₂, 1 mM DTT, 1 mM sodium vanadate, 1 mM phenyl phosphate, 10 μg leupeptin/ml, 10 μg aprotinin/ml and 100 μM benzamidine.

Preparation and Assaying of Kinases

The kinases were assayed in buffer A or buffer C, at 30° C., at a final ATP concentration of 15 μM. The blank values were subtracted and the activities calculated as μmoles of phosphate incorporated per 10 minutes of incubation. The activities are usually expressed as % (percentage) of maximum activity, i.e. in the absence of inhibitors. Controls were performed with appropriate dilutions of dimethyl sulfoxide.

CDK1/cyclin B: was extracted in a homogenization buffer from M phase starfish (*Marthasterias glacialis*) oocytes, and purified by affinity chromatography on sepharose beads labeled with p9$^{CKShs1}$, from which it was eluted with free p9$^{CKShs1}$ as previously described in Meijer et al., (1997) "Biochemical and cellular effects of roscovitine, a potent and selective inhibitor of the cyclin-dependent kinases cdc2, cdk2 and cdk5", *Eur. J. Biochem.* 1997, 243, 527-536. The kinase activity was assayed in buffer C, with 1 mg of histone H1/ml, in the presence of 15 μM of [γ-³³P] ATP (3000 Ci/mmol; 10 mCi/ml) in a final volume of 30 μl. After incubation for 30 minutes at 30° C., aliquotes of 25 μl of the supernatant were spotted onto Whatman P81 phosphocellulose paper filters and, 20 seconds later, the filters were washed five times (for at least five minutes each time) in a solution of 10 ml of phosphoric acid/liter of water. The wet filters were subjected to counting in the presence of an ACS scintillation fluid from Amersham.

CDK2/cyclin A (human, recombinant, expressed in insect cells) was assayed as described for CDK1/cyclin B.

CDK5/p25 was reconstituted by mixing equal amounts of recombinant mammalian CDK5 and p25 expressed in *E. coli* as a GST (glutathione-S-transferase) fusion protein and purified by affinity chromatography on glutathione-agarose (p25 is a truncated version of p35, the 35 kDa CDK5 activator). Its activity was assayed with histone H1 in buffer C as described for CDK1/cyclin B.

CDK9/cyclin T (human, recombinant, expressed in insect cells) was assayed as described for CDK1/cyclin B, but using a pRB fragment (a.a. 773-928) (3.5 μg/assay) as substrate.

GSK-3α/β (pig brain, native, affinity purified) is assayed as described for CDK1 but in buffer A and with a substrate specific for GSK-3 (GS-1; YRRAAVPPSPSLSRHSSPHQS-pEDEEE) (Sp: serine phosphorylated) (Bach S. et al. *J Biol Chem* 2005; 280:31208-19).

CK1δ/ε (pig brain, native, affinity purified) is assayed as described for CDK1 with a substrate specific for CK1, RRKHAAIGSpAYSITA (Reinhardt J. et al. *Protein Expr & Purif* 2007; 54:101-9).

DYRK1A (human, recombinant, expressed in *E. coli* as a GST fusion protein) was purified on glutathione-agarose, assayed as described for CDK1/cyclin B with myelin basic protein (1 mg/ml) as substrate.

TABLE III

| Kinase | CDK1/ cyclin B | CDK2/ cyclin A | CDK5/ p25 | CDK9/ cyclin T | GSK-3α/β | CK1 | DYRK1A |
|---|---|---|---|---|---|---|---|
| Roscovitine | 0.33 | 0.21 | 0.28 | 0.23 | 60 | 4.0 | 3.0 |
| N-&-N1 | 0.09 | 0.04 | 0.07 | 0.043 | 11.0 | 1.2 | 1.3 |
| 1 | 0.18 | 0.22 | 0.18 | 0.093 | >10 | 0.21 | 2.2 |
| 2 | 0.023 | 0.028 | 0.040 | 0.073 | 4.0 | 0.21 | 1.8 |
| 3 | 0.016 | 0.021 | 0.018 | 0.031 | 3.1 | 0.13 | 2.2 |
| 5 | 0.023 | 0.016 | 0.031 | 0.030 | 3.5 | 0.21 | 0.5 |
| 17 | 0.070 | 0.062 | 0.053 | 0.068 | 4.4 | 0.092 | 0.92 |
| 12 | 0.029 | 0.022 | 0.029 | 0.060 | 3.0 | 0.20 | 0.47 |
| 9 | 0.019 | 0.012 | 0.014 | 0.038 | 1.8 | 0.061 | 0.26 |
| 13 | 0.031 | 0.020 | 0.021 | 0.049 | 2.3 | 0.18 | 0.30 |
| 16 | 0.059 | 0.034 | 0.050 | 0.091 | 4.2 | 0.19 | 1.80 |
| 14 | 0.042 | 0.042 | 0.044 | 0.053 | 2.5 | 0.12 | 0.58 |
| 15 | 0.042 | 0.031 | 0.045 | 0.060 | 2.2 | 0.12 | 0.53 |
| 18 | 0.051 | 0.049 | 0.064 | 0.061 | 2.8 | 0.12 | 0.61 |
| 25 | NT | NT | 0.11 | NT | >10 | 0.23 | 1.4 |
| 34 | NT | NT | 0.010 | NT | 0.53 | 0.10 | 0.42 |
| 35 | NT | NT | 0.034 | NT | 1.4 | 0.93 | 0.82 |
| 36 | NT | NT | 0.022 | NT | 1.6 | 0.58 | 1.6 |
| 31 | NT | NT | 0.025 | NT | 1.0 | 0.36 | 0.71 |
| 23 | NT | NT | <0.03 | NT | 1.2 | 0.13 | 1.3 |

TABLE III-continued

| Kinase | CDK1/ cyclin B | CDK2/ cyclin A | CDK5/ p25 | CDK9/ cyclin T | GSK-3α/β | CK1 | DYRK1A |
|---|---|---|---|---|---|---|---|
| 21 | NT | NT | 0.043 | NT | 1.2 | 0.11 | 1.2 |
| 28 | NT | NT | 0.12 | NT | 7.0 | 0.41 | 0.58 |
| 30 | NT | NT | 0.38 | NT | 2.1 | 0.56 | 1.4 |

"NT": Not tested

According to a second series of pharmacological assays, tests on cells were carried out, more particularly on the SH-SY5Y and CLL line, according to the methodology described hereinafter. Table IV collates examples of results in $IC_{50}$ values in µM.

Materials and Methods

A. SH-SY5Y Human Neuroblastoma Cells

Chemical Reagents

A Cell Titer 96® kit containing the MTS reagent was purchased from Promega (Madison, Wis., USA). The protease inhibitor cocktail came from Roche and the fetal calf serum (FCS) came from Invitrogen. The reagents not listed came from Sigma, unless otherwise indicated.

Cell Line And Culture Conditions

The SH-SY5Y human neuroblastoma cell line was grown in a DMEM medium with L-glutamine from Invitrogen (Cergy Pontoise, France), antibiotics and 10% by volume of FCS from Invitrogen. The general culture conditions were a 5% $CO_2$ atmosphere and a temperature of 37° C. The culture plates and other disposable plastic tools were supplied by Corning (Corning, N.Y., USA). The treatments with the compounds of the invention were carried out on cultures in exponential growth over time, and indicated concentrations. The control experiments were carried out also using suitable dilutions of DMSO.

Demonstration of Cell Viability

The cell viability was determined by measuring the reduction of 3-(4,5-dimethylthiazol-2-yl)-5-(3-carboxymethoxyphenyl)-2-(4-sulfophenyl)-2H-tetrazolium (MTS). The procedure was as described in detail in Ribas J. at al., 2004, "Cell differentiation, caspase inhibition, and macromolecular synthesis blockage, but not BCL-2 or BCL-XL proteins, protect SH-SYS5 cells from apoptosis triggered by two CDK inhibitory drugs", *Exp. Cell Res*, 2004, 195, 9-24.

B. Human Chronic Lymphoid Leukemia (B-CLL) Lymphocytes

Patients and Cell Purification

The CLL cells were isolated from heparinized blood of untreated patients after informed consent.

The mononuclear cells were isolated by centrifugation on a Lymphosep density gradient (Biowest). All the B-CLL samples had a Matutes score of 4 or 5. The percentage of B-CLL lymphocytes was evaluated by flow cytometry after labeling with CD19-PE (clone J4,119) and CD5-PC5 (clone BL1a) and the cells were analyzed by FACS (EPICS XL, Beckman Coulter, France). When the percentage of CD19+/CD5+ cells was less than 90%, the B lymphocytes were enriched using the kit II for B-cell enrichment by immunomagnetic depletion of the monocytes, NK cells, granulocytes and T lymphocytes (Miltenyi Biotech).

Apoptosis

The B-CLL cells were cultured (300 000 cells/well) at 37° C. in RPMI 1640 medium (Lonza) containing 10% of FCS (InVitrogen) with various concentrations of the compounds of the invention. After incubation, the B-CLL cells were harvested, washed in PBS and resuspended in 100 µl of 1× binding buffer containing FITC-conjugated annexin V and propidium iodide (Beckman Coulter Apoptosis Detection Kit). After incubation for 10 min on ice, the cells were analyzed by flow cytometry and the percentage of cells undergoing apoptosis was determined.

The compounds of the invention generally have an $IC_{50}$ of less than 1 µm for the two cell lines under consideration.

TABLE IV

| Cell line | (R)-roscovitine | N-&-N1 | 1 | 2 | 3 | 5 | 34 |
|---|---|---|---|---|---|---|---|
| SH-SY5Y | 17 | 2.6 | 0.43 | 0.044 | 0.059 | 0.080 | <0.03 |
| CLL | | 8.96 | 1.42 | 0.189 | 0.032 | 0.032 | NT | NT |
| Cell line | | | 25 | 35 | 36 | 31 | 30 |
| SH-SY5Y | | | 1.7 | 0.05 | 0.026 | <0.03 | 1.4 |
| CLL | | | NT | NT | NT | NT | NT |

"NT": Not tested

The compounds according to the invention can therefore be used for preparing medicaments, in particular medicaments which have an inhibitory activity on protein kinases and in particular on cyclin-dependent kinases (CDKs), on casein kinases 1 (CK1s) and on DYRKS.

Thus, a subject of the invention, according to another of its aspects, is medicaments which comprise a compound of formula (I), or an addition salt of said compound with a pharmaceutically acceptable acid, or else a hydrate or a solvate.

These medicaments find their use in therapy, in particular in the prevention and treatment of various pathological conditions such as cancers, chronic neurodegenerative diseases such as Alzheimer's disease or Parkinson's disease, acute neurodegenerative diseases such as cerebral trauma, stroke, epilepsy, pulmonary inflammations, arthritis, viral infections (AIDS, Herpes), pain treatment, diabetes, in particular type 2 diabetes, kidney diseases such as renal polycystosis or glomerulonephritis, leukemias such as chronic lymphoid leukemia, in particular of s-cell type, or parasites such as *Plasmodium* and *Leishmania*.

The compounds of the invention are most particularly useful for preventing and/or treating the following diseases: cancers, chronic lymphoid leukemia, Alzheimer's disease, Parkinson's disease, stroke, pulmonary inflammations, AIDS, renal polycystosis, glomerulonephritis.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or optional salt, solvate or hydrate thereof, can be administered in unit administration form, as a mixture with conventional pharmaceutical excipients, to human beings for the prophylaxis or treatment of the disorders or diseases mentioned above.

The suitable unit administration forms comprise forms for oral administration, such as tablets, soft or hard gel capsules, powders, granules and oral solutions or suspensions, sublingual, buccal, intratracheal, intraocular and intranasal administration forms, forms of administration by inhalation, topical, transdermal, subcutaneous, intramuscular or intravenous administration forms, rectal administration forms, and implants.

With oral administration, the dose of active ingredient administered per day can reach 1 to 500 mg/kg, in one or more intakes.

There may be particular cases where higher or lower dosages are appropriate; such dosages do not depart from the context of the invention. According to the usual practice, the dosage appropriate for each patient is determined by the physician according to the method of administration and the weight and response of said patient.

According to one of its aspects, the present invention relates to the use of a compound of formula (I), (Ia), (Ib), (Ie), (Id), (Ie), (If) or (1) to (38) or a pharmaceutically acceptable salt thereof, for preparing a medicament intended for treating at least one of the diseases mentioned above, and in particular cancer.

According to another of its aspects, the present invention relates to a compound of formula (I), (Ia), (Ib), (Ic), (Id), (Ie), (If) or (1) to (38) or a pharmaceutically acceptable salt thereof, for use thereof as a medicament intended for treating and preventing at least one of the diseases mentioned above, and in particular as an anticancer agent.

According to yet another of its aspects, the present invention also relates to a method for preventing and/or treating the pathological conditions indicated above, which comprises the administration, to a patient, of an effective dose of a compound according to the invention, or a pharmaceutically acceptable salt or hydrate or solvate thereof.

The pharmaceutical compositions according to the invention may also find a use in the veterinary field and also be administered to animals such as dogs and cats for the prophylaxis or treatment of the disorders or diseases mentioned above.

The invention claimed is:
1. A compound of formula (I) below, or a pharmaceutically acceptable salt thereof:

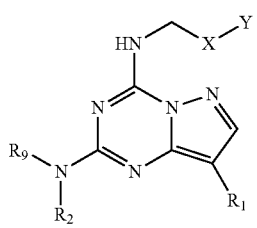

(I)

where:
$R_1$ is a $(C_1-C_6)$alkyl group or a $(C_3-C_6)$cycloalkyl group;
$R_2$ is:
a $(C_1-C_6)$alkyl group, a $(C_3-C_6)$cycloalkyl group, a $(C_1-C_6)$alkenyl group, a $(C_1-C_6)$fluoroalkyl group, a $(C_1-C_3)$fluoroalkoxy group, or a $(C_1-C_6)$alkoxy $(C_1-C_6)$alkyl group, substituted:
(i) with one to three hydroxyl groups, or
(ii) with an $NR_aR_b$ group, where $R_a$ and $R_b$ are independently a hydrogen atom or a $(C_1-C_3)$ alkyl group: or
a pyrrolidinylmethyl group substituted with one to three hydroxyl groups;

$R_9$ is:
hydrogen, a $(C_1-C_6)$alkyl group, a $(C_3-C_6)$cycloalkyl group, a $(C_1-C_6)$alkenyl group, a $(C_1-C_6)$fluoroalkyl group, a $(C_1-C_3)$fluoroalkoxy group, or a $(C_1-C_6)$alkoxy$(C_1-C_6)$alkyl group, substituted:
(i) with one to three hydroxyl groups, or
(ii) with an $NR_aR_b$ group; or
a pyrrolidinylmethyl group substituted with one to three hydroxyl groups;
said $R_2$ group and $R_9$ group independently being optionally substituted with an —$OCOR_3$ group, in which $R_3$ is a natural or unnatural amino acid group or a piperidyl group of formula (B):

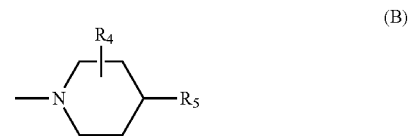

(B)

where:
$R_4$ is a hydrogen, a halogen atom, a $(C_1-C_3)$alkyl group, a hydroxy$(C_1-C_3)$alkyl group or an —$NR_aR_b$ group; and
$R_5$ is a hydrogen, a $(C_1-C_3)$alkyl group, an —$N(Me)_2$ group, a piperidyl group or a morpholinyl group;
alternatively, $R_2$ and $R_9$ together form, with the nitrogen atom which bears them, a heterocycle selected from the group consisting of a pyrrolidin group, a piperidinyl group, a piperazinyl group, and a piperidinylpiperidiny group, the heterocycles optionally being substituted with one to three groups selected from the group consisting of:
hydroxyl; and
$(C_1-C_6)$alkyl or $(C_1-C_6)$alkoxy$(C_1-C_6)$alkyl substituted with:
(i) one to three hydroxyl groups, or
(ii) an $NR_aR_b$ group;
X and Y are independently a phenyl group or a heteroaryl group, said heteroaryl and phenyl groups optionally being substituted with one or two groups independently selected from the group consisting of a $(C_1-C_2)$alkyl group, a $(C_1-C_2)$alkoxy group, a halogen atom, a $(C_1-C_2)$fluoroalkyl group, a $(C_1-C_2)$fluoroalkoxy group, a hydroxyl group, a —COOH group, a —$CONHR_6$ group, and an —$NR_aR_b$ group;
$R_6$ is a hydrogen or a $(C_1-C_3)$alkyl, group and
said heteroaryl group is selected from the group consisting of a thienyl group, a pyridyl group, a pyrimidinyl group, a thiazolyl group, a pyrrolyl group, and a furanyl group.

2. The compound as claimed in claim 1, wherein $R_3$ is one of the following formulae (a-1) to (a-5), or enantiomers thereof:

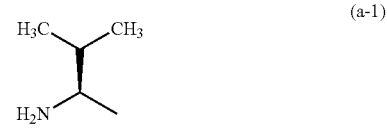

(a-1)

-continued

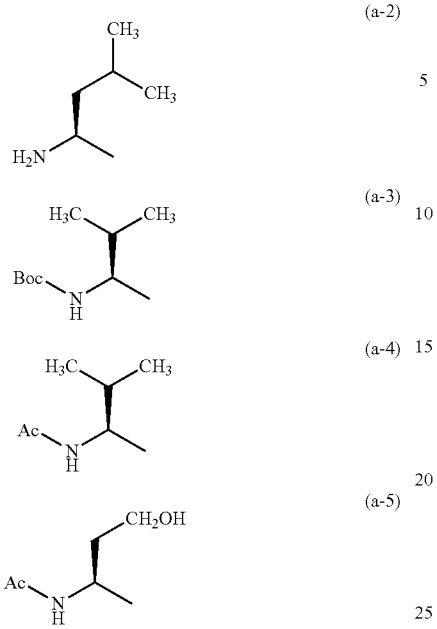

where Boc is a tert-butoxycarbonyl group and Ac is an acetyl group.

3. The compound as claimed in claim 1, wherein at least one of the X and Y groups is substituted with one or two substitution groups, said substitution group being selected from the group consisting, of a $(C_1-C_2)$alkyl group, a $(C_1-C_2)$ fluoroalkyl group, a $(C_1-C_2)$alkoxy group, a $(C_1-C_2)$fluoroalkoxy group, a halogen atom, a hydroxyl group, and a —COOH group.

4. The compound as claimed in claim 1, wherein $R_2$ is one of the following formulae:

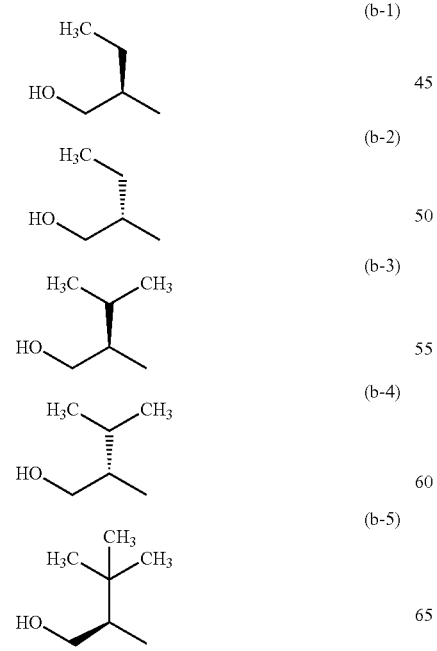

-continued

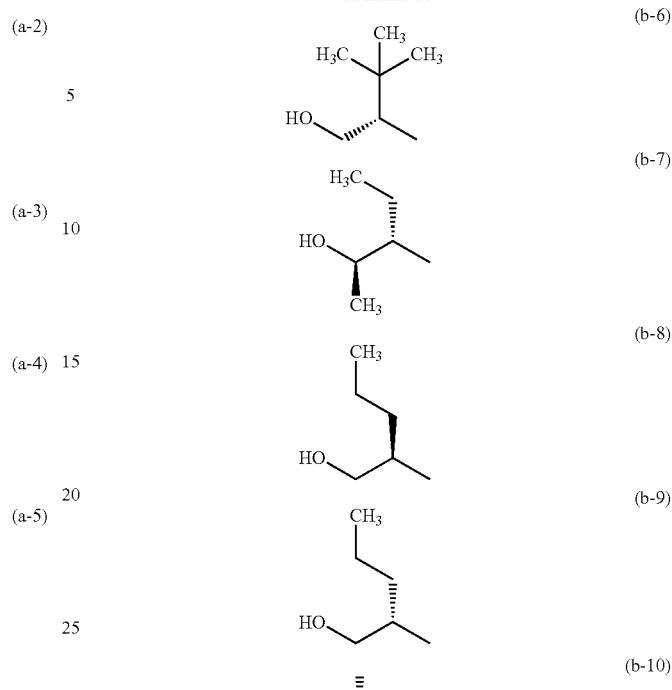

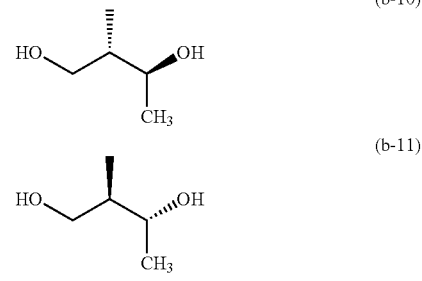

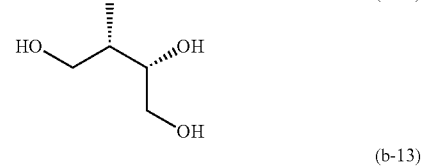

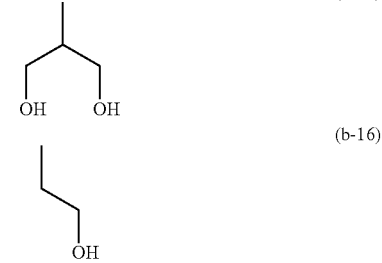

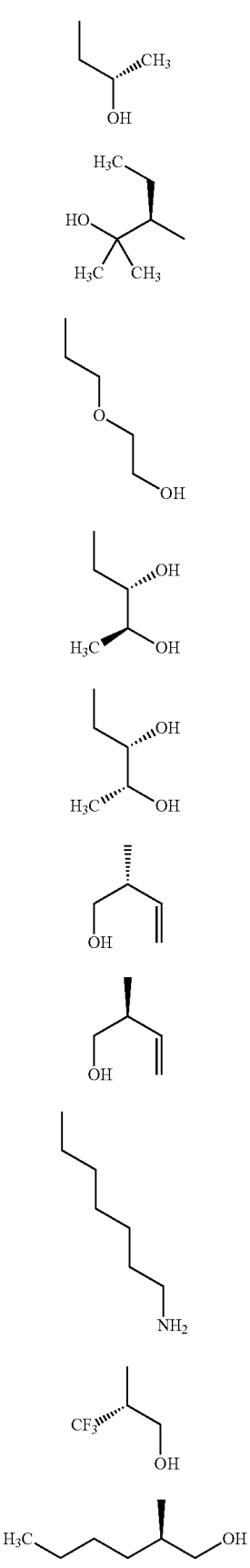
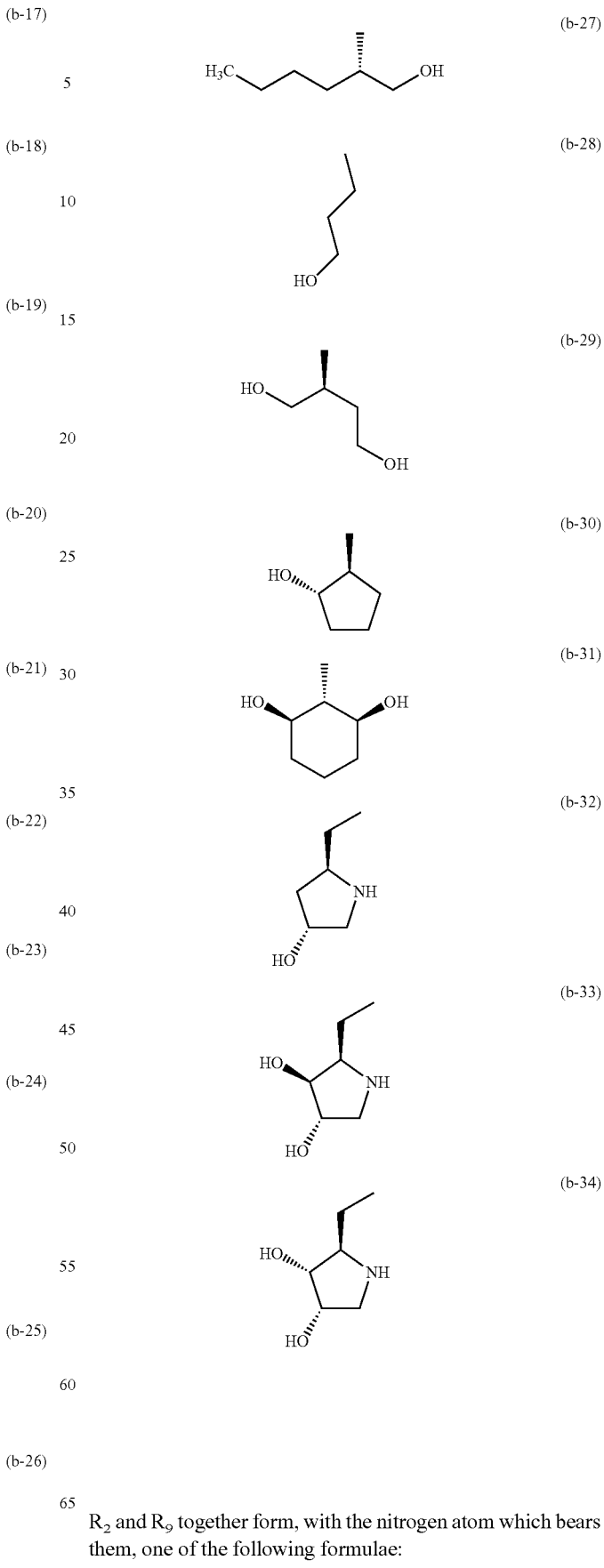
$R_2$ and $R_9$ together form, with the nitrogen atom which bears them, one of the following formulae:

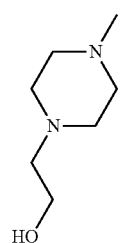 (b-35)

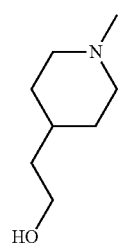 (b-36)

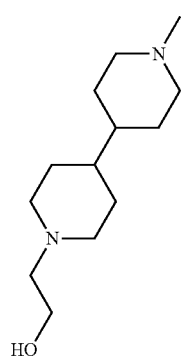 (b-37)

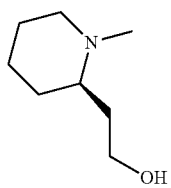 (b-38)

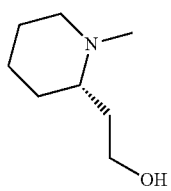 (b-39)

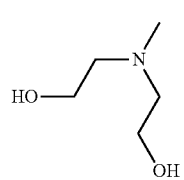 (b-40)

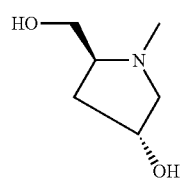 (b-41)

-continued

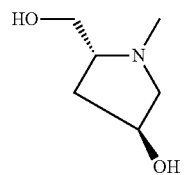 (b-42)

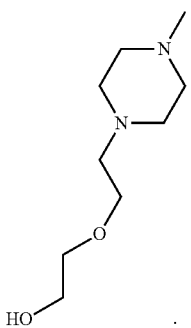 (b-43)

5. The compound as claimed in claim 1, wherein the compound is of a formula (Ia), or a pharmaceutically acceptable salt thereof:

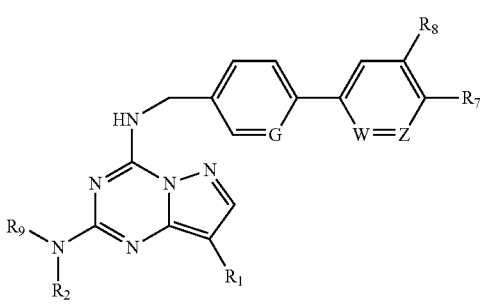 (Ia)

where:

R$_2$ and R$_9$ are independently a (C$_1$-C$_6$)alkyl group, a (C$_1$-C$_6$)fluoroalkyl group, a (C$_1$-C$_3$)fluoroalkoxy group, or a (C$_1$-C$_6$)alkoxy(C$_1$-C$_6$)alkyl group, said group being substituted with one to three hydroxyl groups, R$_9$ optionally being a hydrogen atom; or R$_2$ and R$_9$ together form, with the nitrogen atom which bears them, a piperidin-1-yl or piperidin-4-ylpiperidin-1-yl group, said group being substituted with one to three (C$_1$-C$_6$)alkyl groups substituted with a hydroxyl group;

R$_7$ and R$_8$ are independently a hydrogen atom, a (C$_1$-C$_2$) alkyl group, a (C$_1$-C$_2$)fluoroalkyl group, a (C$_1$-C$_2$) alkoxy group, a (C$_1$-C$_2$)fluoroalkoxy group, a halogen atom, a hydroxyl group, or a —COOH group;

G is —CH= or —N=; and when G is —CH=, W and Z are either simultaneously —CH=, or one is —N= and the other is —CH=, and when G is —N=, then W and Z are —CH.

6. The compound as claimed in claim 1, wherein the compound is of a formula (Ib), or a pharmaceutically acceptable salt thereof:

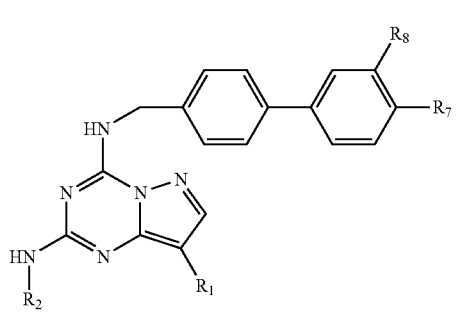

(Ib)

where:
- $R_2$ is a ($C_1$-$C_6$ alkyl group, a ($C_1$-$C_6$)fluoroalkyl group, a ($C_1$-$C_3$)fluoroalkoxy group, or a ($C_1$-$C_6$)alkoxy($C_1$-$C_6$)alkyl group, said group being substituted with one to three hydroxyl groups; and
- $R_7$ and $R_8$ are independently a hydrogen atom, a ($C_1$-$C_2$) alkyl group, a ($C_1$-$C_2$)fluoroalkyl group, a ($C_1$-$C_2$) alkoxy group, a ($C_1$-$C_2$)fluoroalkoxy group, a halogen atom, a hydroxyl group, or a —COOH group.

7. The compound as claimed in claim 1, wherein the compound is of a formula (Ic), or a pharmaceutically acceptable salt thereof:

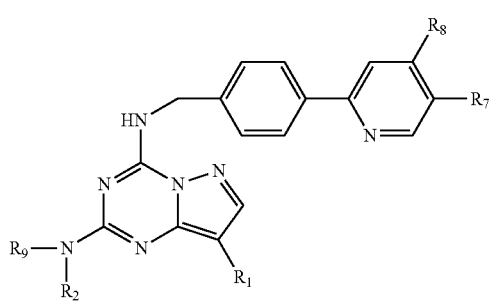

(Ic)

where:
- $R_9$ is a hydrogen atom and $R_2$ is a ($C_1$-$C_6$)alkyl group, a ($C_1$-$C_6$)fluoroalkyl group, a ($C_1$-$C_3$)fluoroalkoxy group, or a ($C_1$-$C_6$)alkoxy($C_1$-$C_6$)alkyl group, said group being substituted with one to three hydroxyl groups; or
- $R_2$ and $R_9$ together form, with the nitrogen atom which bears them, a piperidin-1-yl or piperidin-4-ylpiperidin-1-yl group, said group being substituted with one to three ($C_1$-$C_6$)alkyl groups substituted with a hydroxyl group; and
- $R_7$ and $R_8$ are independently a hydrogen atom, a ($C_1$-$C_2$) alkyl group, a ($C_1$-$C_2$)fluoroalkyl group, a ($C_1$-$C_2$) alkoxy group, a ($C_1$-$C_2$)fluoroalkoxy group, a halogen atom, a hydroxyl group, or a —COOH group.

8. The compound as claimed in claim 1, wherein the compound is of a formula (Id), or a pharmaceutically acceptable salt thereof:

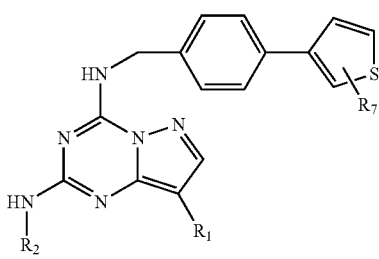

(Id)

where:
- $R_2$ is a ($C_1$-$C_6$)alkyl group, a ($C_1$-$C_6$)fluoroalkyl group, a ($C_1$-$C_3$)fluoroalkoxy group, or a ($C_1$-$C_6$)alkoxy($C_1$-$C_6$)alkyl group, said group being substituted with one to three hydroxyl groups, $R_9$ optionally being a hydrogen atom; and
- $R_7$ is a hydrogen atom, a ($C_1$-$C_2$)alkyl group, a ($C_1$-$C_2$) fluoroalkyl group, a ($C_1$-$C_2$)alkoxy group, a ($C_1$-$C_2$) fluoroalkoxy group, a halogen atom, a hydroxyl group, or a —COOH group.

9. The compound as claimed in claim 1, wherein:

the compound is of a formula (Ie):

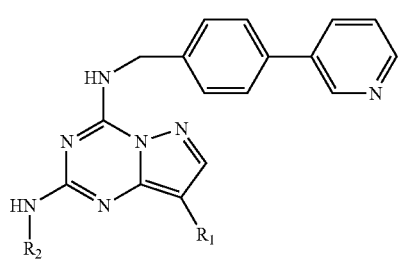

(Ie)

where:
- $R_2$ is a ($C_1$-$C_6$)alkyl group, a ($C_1$-$C_6$)fluoroalkyl group, a ($C_1$-$C_3$)fluoroalkoxy group, or a ($C_1$-$C_6$)alkoxy($C_1$-$C_6$)alkyl group, said group being substituted with one to three hydroxyl groups; or the compound is of a formula (If):

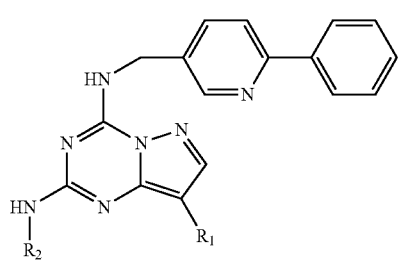

(If)

where:
- $R_2$ is a ($C_1$-$C_6$)alkyl group, a ($C_1$-$C_6$)fluoroalkyl group, a ($C_1$-$C_3$)fluoroalkoxy group, or a ($C_1$-$C_6$)alkoxy($C_1$-

C$_6$)alkyl group, said group being substituted with one to three hydroxyl groups.

10. The compound as claimed in claim 1, wherein the compound is chosen from one of the following compounds:

(R)-2-(1-hydroxybut-2-ylamino)-8-isopropyl-4-(4 phenylbenzylamino)pyrazolo[1,5-a]-1,3,5-triazine;

(R)-2-(1-hydroxybut-2-ylamino)-8-isopropyl-4-[4-(pyridin-2-yl)benzylamino]pyrazolo[1,5-a]-1,3,5-triazine;

Fumarate salt of (R)-2-(1-hydroxybut-2-ylamino)-8-isopropyl-4-[4-(pyridin-2-yl)benzylamino]pyrazolo[1,5-a]-1,3,5-triazine;

(S)-2-(1-hydroxybut-2-ylamino)-8-isopropyl-4-[4-(pyridin-2-yl)benzylamino]pyrazolo[1,5-a]-1,3,5-triazine;

Fumarate salt of (5)-2-(1-hydroxybut-2-ylamino)-8-isopropyl-4-[4-(pyridin-2-yl)benzylamino]pyrazolo[1,5-a]-1,3,5-triazine;

(R)-2-(1-hydroxybut-2-ylamino)-8-isopropyl-4-[4-(thiophen-3-yl)benzylamino]pyrazolo[1,5-a]-1,3,5-triazine;

(S)-2-(1-hydroxybut-2-ylamino)-8-isopropyl-4-[4-(thiophen-3-yl)benzylamino]pyrazolo[1,5-a]-1,3,5-triazine;

(S)-2-(1,2-dihydroxypropan-3-ylamino)-8-isopropyl-4-[4-(pyridin-2-yl)benzylamino]pyrazolo[1,5-a]-1,3,5-triazine;

Fumarate salt of (S)-2-(1,2-dihydroxypropan-3-ylamino)-8-isopropyl-4-[4-(pyridin-2-yl)benzylamino]pyrazolo[1,5-a]-1,3,5-triazine;

(R)-2-(1,2-dihydroxypropan-3-ylamino)-8-isopropyl-4-[4-(pyridin-2-yl)benzylamino]pyrazolo[1,5-a]-1,3,5-triazine;

Fumarate salt of (R)-2-(1,2-dihydroxypropan-3-ylamino)-8-isopropyl-4-[4-(pyridin-2-yl)benzylamino]pyrazolo[1,5-a]-1,3,5-triazine;

(2R,3R)-2-(1,3-dihydroxybut-2-ylamino)-8-isopropyl-4-[4-(pyridin-2-yl)benzylamino]pyrazolo[1,5-a]-1,3,5-triazine;

Fumarate salt of (2R,3R)-2-(1,3-dihydroxybut-2-ylamino)-8-isopropyl-4-[4-(pyridin-2-yl)benzylamino]pyrazolo[1,5-a]-1,3,5-triazine;

(2S,3S)-2-(1,3-dihydroxybut-2-ylamino)-8-isopropyl-4-[4-(pyridin-2-yl)benzylamino]pyrazolo[1,5-a]-1,3,5-triazine;

Fumarate salt of (2S,3S)-2-(1,3-dihydroxybut-2-ylamino)-8-isopropyl-4-[4-(pyridin-2-yl)benzylamino]pyrazolo[1,5-a]-1,3,5-triazine;

(2R,3R)-2-(1,3-dihydroxybut-2-ylamino)-8-isopropyl-4-[4-(thiophen-3-yl)benzylamino]pyrazolo[1,5-a]-1,3,5-triazine;

2-(1,3-dihydroxyprop-2-ylamino)-8-isopropyl-4-[4-(pyridin-2-yl)benzylamino]pyrazolo[1,5-a]-1,3,5-triazine;

Fumarate salt of 2-(1,3-dihydroxyprop-2-ylamino)-8-isopropyl-4-[4-(pyridin-2-yl)benzylamino]pyrazolo[1,5-a]-1,3,5-triazine;

2-(1,3-dihydroxyprop-2-ylamino)-8-isopropyl-4-[4-(pyridin-3-yl)benzylamino]pyrazolo[1,5-a]-1,3,5-triazine;

(S)-2-(1-hydroxybut-2-ylamino)-8-isopropyl-4-[4-(pyridin-3-yl)benzylamino]pyrazolo[1,5-a]-1,3,5-triazine;

(2S,3S)-2-(1,3-dihydroxybut-2-ylamino)-8-isopropyl-4-[4-phenyl(pyridin-3-yl)methylamino]pyrazolo[1,5-a]-1,3,5-triazine;

(S)-2-(1-hydroxybut-2-ylamino)-8-isopropyl-4-[4-phenyl(pyridin-3-yl)methylamino]pyrazolo[1,5-a]-1,3,5-triazine;

(2R,3R)-2-(1,3-dihydroxybut-2-ylamino)-8-isopropyl-4-[4-phenyl(pyridin-3-yl)methylamino]pyrazolo[1,5-a]-1,3,5-triazine;

2-(1,3-dihydroxyprop-2-ylamino)-8-isopropyl-4-[4-phenyl(pyridin-3-yl)methylamino]pyrazolo[1,5-a]-1,3,5-triazine;

(R)-2-(1-hydroxy-4-methylpent-2-ylamino)-8-isopropyl-4-[4-phenyl(pyridin-3-yl)methylamino]pyrazolo[1,5-a]-1,3,5-triazine;

(S)-2-(1-hydroxy-4-methylpent-2-ylamino)-8-isopropyl-4-[4-phenyl(pyridin-3-yl)methylamino]pyrazolo[1,5-a]-1,3,5-triazine;

(S)-2-(1-hydroxy-3,3-dimethylbut-2-ylamino)-8-isopropyl-4-[4-(pyridin-2-yl)benzylamino]pyrazolo[1,5-a]-1,3,5-triazine;

(S)-2-(1-hydroxy-3-methylbut-2-ylamino)-8-isopropyl-4-[4-(pyridin-2-yl)benzylamino]pyrazolo[1,5-a]-1,3,5-triazine;

2-[4-[1-[8-isopropyl-4-[[4-(pyridin-2-yl)phenyl]methylamino]pyrazolo[1,5-a]-1,3,5-triazin-2-yl]piperidin-4-yl]piperidin-1-yl]ethanol);

2-[4-[8-isopropyl-4-[[4-(pyridin-2-yl)phenyl]methylamino]pyrazolo[1,5-a]-1,3,5-triazin-2-yl]piperazin-1-yl]ethanol;

(R)-2-(1,2-dihydroxypropan-3-ylamino)-8-ethyl-4-[4-(pyridin-2-yl)benzylamino]pyrazolo[1,5-a]-1,3,5-triazine;

[(2R)-3-[[8-ethyl-4-[[4-(2-pyridyl)phenyl]methylamino]pyrazolo[1,5-a][1,3,5]triazin-2-yl]amino]-2-hydroxypropyl] (2R)-2-Bocamino-3-methylbutanoate;

[(2R)-3-[[8-ethyl-4-[[4-(2-pyridyl)phenyl]methylamino]pyrazolo[1,5-a][1,3,5]triazin-2-yl]amino]-2-hydroxypropyl] (2R)-2-amino-3-methylbutanoate in the form of a base or of a salt;

(S)-2-(1,2-dihydroxypropan-3-ylamino)-8-ethyl-4-[4-(pyridin-2-yl)benzylamino]pyrazolo[1,5-a]-1,3,5-triazine;

(S)-8-ethyl-2-(1-hydroxybut-2-ylamino)-4[4-(pyridin-2-yl)benzylamino]pyrazolo[1,5-a]-1,3,5-triazine;

(R)-8-ethyl-2-(1-hydroxybut-2-ylamino)-4-[4-(pyridin-2-yl)benzylamino]pyrazolo[1,5-a]-1,3,5-triazine;

2-(1,3-dihydroxyprop-2-ylamino)-8-ethyl-4[4-(pyridin-2-yl)benzylamino]pyrazolo[1,5-a]-1,3,5-triazine;

2-[(2S)-1-[8-ethyl-4-[[4-(2-pyridyl)phenyl]methylamino]pyrazolo[1,5-a][1,3,5]triazin-2-yl]-2-piperidyl]ethanol;

2-[[8-ethyl-4-[[4-(2-pyridyl)phenyl]methylamino]pyrazolo[1,5-a][1,3,5]triazin-2-yl]-(2-hydroxyethyl)amino]ethanol;

(2R,3R)-2-[[8-ethyl-4-[[4-(2-pyridyl)phenyl]methylamino]pyrazolo[1,5-a][1,3,5]triazin-2-yl]amino]butane-1,3-diol;

(2S,3S)-2-[[8-ethyl-4-[[4-(2-pyridyl)phenyl]methylamino]pyrazolo[1,5-a][1,3,5]triazin-2-yl]amino]butane-1,3-diol; and their optional salts of pharmaceutically acceptable acids.

11. A process for preparing a compound of formula (I) as claimed in claim 1, comprising:

reacting a compound of formula (IIa) with meta-chloroperbenzoic acid in an oxidation reaction to obtain a sulfone:

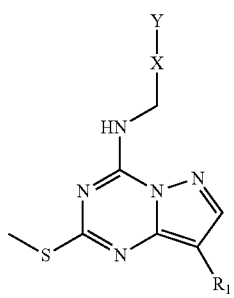

(IIa)

and
directly using the sulfone obtainedy in a nucleophilic substitution reaction in the presence of a primary amine of formula NH—R$_2$R$_9$ at a temperature of from 100 to 180° C., to produce a compound of formula (I); or reacting a compound of formula (IIb) with a metal, to give a compound of formula (IIa):

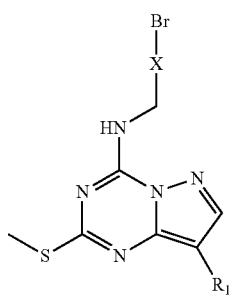

(IIb)

reacting the compound of formula (IIb) with meta-chloroperbenzoic acid in an oxidation reaction,
directly using the sulfone obtained in a nucleophilic substitution reaction in the presence of a primary amine of formula NH—R$_2$R$_9$, so as to give a compound of formula (III):

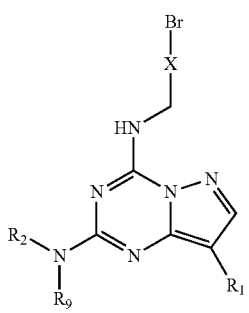

(III)

and
subjecting the compound to a coupling reaction catalyzed by a metal, to produce a compound of formula (I).

12. A pharmaceutical composition comprising a compound of formula (I) as claimed in claim 1, and at least one pharmaceutically acceptable excipient.

* * * * *